United States Patent
Sholev et al.

(10) Patent No.: US 9,763,659 B2
(45) Date of Patent: Sep. 19, 2017

(54) ARTHROSCOPIC SURGICAL DEVICE

(75) Inventors: Mordehai Sholev, D.N. Menashe (IL); Ronen Raz, Magal (IL); Raphael Meloul, Shilo (IL)

(73) Assignee: MININVASIVE LTD., Tel Aviv (IL)

( * ) Notice: Subject to any disclaimer, the term of this patent is extended or adjusted under 35 U.S.C. 154(b) by 600 days.

(21) Appl. No.: 14/240,227

(22) PCT Filed: Aug. 23, 2012

(86) PCT No.: PCT/IL2012/000318
§ 371 (c)(1),
(2), (4) Date: Apr. 9, 2014

(87) PCT Pub. No.: WO2013/027209
PCT Pub. Date: Feb. 28, 2013

(65) Prior Publication Data
US 2014/0303625 A1    Oct. 9, 2014

Related U.S. Application Data

(60) Provisional application No. 61/636,751, filed on Apr. 23, 2012, provisional application No. 61/584,267, (Continued)

(51) Int. Cl.
*A61B 17/16*  (2006.01)
*A61B 17/04*  (2006.01)
(Continued)

(52) U.S. Cl.
CPC ...... *A61B 17/0642* (2013.01); *A61B 17/0482* (2013.01); *A61B 17/0483* (2013.01); (Continued)

(58) Field of Classification Search
CPC ....... A61B 17/04; A61B 17/16; A61B 17/064; A61B 17/1642; A61B 17/0483; A61B 17/0642
See application file for complete search history.

(56) References Cited

U.S. PATENT DOCUMENTS 2,579,192 A    12/1951    Kohl
5,250,055 A    10/1993    Moore et al.
(Continued)

FOREIGN PATENT DOCUMENTS

CN    101193600    9/2010
EP    1898812    3/2008
(Continued)

OTHER PUBLICATIONS

European Search Report dated Jan. 27, 2016 which issued during the prosecution of Applicant's European App No. 13733888.
(Continued)

*Primary Examiner* — Christopher Beccia
(74) *Attorney, Agent, or Firm* — Sughrue Mion, PLLC

(57) ABSTRACT

An arthroscopic surgical device for tunneling through hard tissue including an arcuate tunneling needle driver and a bone engagement element, the arcuate needle driver and the bone engagement element being joined together to provide a joined needle driver and bone engagement element having at least two different operative orientations including an arthroscopic operative orientation wherein the joined arcuate needle driver and bone engagement element has a trans-incision insertion cross-sectional footprint and a tunneling operative orientation suitable for tunneling, wherein the joined arcuate needle driver and bone engagement element has a tunneling cross-sectional footprint which is substantially greater than the insertion cross-sectional footprint.

9 Claims, 50 Drawing Sheets

Related U.S. Application Data filed on Jan. 8, 2012, provisional application No. 61/526,717, filed on Aug. 24, 2011.

(51) Int. Cl.
*A61B 17/064* (2006.01)
*A61B 17/88* (2006.01)
*A61B 17/06* (2006.01)
*A61B 17/29* (2006.01)

(52) U.S. Cl.
CPC ...... *A61B 17/1604* (2013.01); *A61B 17/1642* (2013.01); *A61B 17/8861* (2013.01); *A61B 17/06061* (2013.01); *A61B 2017/06042* (2013.01); *A61B 2017/2923* (2013.01)

(56) References Cited

U.S. PATENT DOCUMENTS

| | | | |
|---|---|---|---|
| 5,387,221 A | 2/1995 | Bisgaard | |
| 5,499,991 A | 3/1996 | Garman et al. | |
| 5,665,096 A * | 9/1997 | Yoon | A61B 17/0469 606/139 |
| 5,681,333 A | 10/1997 | Burkhart et al. | |
| 5,961,530 A | 10/1999 | Moore | |
| 6,328,744 B1 * | 12/2001 | Harari | A61B 17/0625 408/241 R |
| 6,443,963 B1 | 9/2002 | Baldwin | |
| 6,523,417 B1 | 2/2003 | Donahue | |
| 7,029,479 B2 * | 4/2006 | Tallarida | A61B 17/8615 606/102 |
| 7,097,648 B1 | 8/2006 | Globerman et al. | |
| 7,166,116 B2 | 1/2007 | Lizardi et al. | |
| 7,662,171 B2 * | 2/2010 | West, Jr. | A61B 17/0401 606/232 |
| 8,282,657 B2 | 10/2012 | McClurg et al. | |
| 2002/0040227 A1 | 4/2002 | Harari | |
| 2003/0078599 A1 | 4/2003 | O'Quinn | |
| 2006/0195121 A1 | 8/2006 | Chu | |
| 2006/0271060 A1 * | 11/2006 | Gordon | A61B 17/0401 606/103 |
| 2007/0005067 A1 * | 1/2007 | Dross | A61B 17/0483 606/232 |
| 2007/0179509 A1 | 8/2007 | Nagata et al. | |
| 2008/0109015 A1 | 5/2008 | Chu et al. | |
| 2008/0228224 A1 | 9/2008 | Sauer | |
| 2009/0012538 A1 | 1/2009 | Saliman et al. | |
| 2009/0062819 A1 | 3/2009 | Burkhart | |
| 2009/0069823 A1 | 3/2009 | Foerster | |
| 2009/0105729 A1 | 4/2009 | Zentgraf | |
| 2009/0105743 A1 | 4/2009 | Chu | |
| 2009/0131956 A1 | 5/2009 | Dewey | |
| 2009/0138029 A1 | 5/2009 | Saliman et al. | |
| 2009/0312782 A1 | 12/2009 | Park | |
| 2010/0076436 A1 * | 3/2010 | Hajianpour | A61B 17/6491 606/59 |
| 2010/0106194 A1 | 4/2010 | Bonutti et al. | |
| 2010/0152751 A1 | 6/2010 | Meade et al. | |
| 2010/0191248 A1 | 7/2010 | Mehta et al. | |
| 2010/0198258 A1 | 8/2010 | Heaven et al. | |
| 2010/0318139 A1 | 12/2010 | Beauchamp | |
| 2011/0022063 A1 * | 1/2011 | McClurg | A61B 17/0469 606/145 |
| 2011/0106124 A1 | 5/2011 | Beauchamp | |
| 2012/0239085 A1 | 9/2012 | Schlotterback et al. | |
| 2012/0323248 A1 | 12/2012 | Dross | |
| 2013/0123810 A1 | 5/2013 | Brown et al. | |
| 2013/0178854 A1 | 7/2013 | Sholev et al. | |
| 2014/0214038 A1 | 7/2014 | Sholev | |
| 2014/0303625 A1 | 10/2014 | Sholev et al. | |

FOREIGN PATENT DOCUMENTS

| | | |
|---|---|---|
| EP | 1970016 | 9/2008 |
| EP | 2698128 | 2/2014 |
| JP | 1996-033635 | 2/1996 |
| JP | 1996-509918 | 10/1996 |
| JP | 2003-501132 A | 1/2003 |
| JP | 2008-510526 A | 4/2008 |
| JP | 2008-546489 | 12/2008 |
| WO | 96/27331 | 9/1996 |
| WO | 97/47246 | 12/1997 |
| WO | 00/74578 | 12/2000 |
| WO | 02/07609 | 1/2002 |
| WO | 2009/107121 | 9/2009 |
| WO | 2010/056785 | 5/2010 |
| WO | 2010/056786 | 5/2010 |
| WO | 2010/056787 | 5/2010 |
| WO | 2011/160166 | 12/2011 |
| WO | 2012/007941 | 1/2012 |
| WO | 2013/027209 | 2/2013 |
| WO | 2013/027210 | 2/2013 |
| WO | 2013/071234 A1 | 5/2013 |
| WO | 2013/102909 | 7/2013 |
| WO | 2014/147619 | 9/2014 |

OTHER PUBLICATIONS

An Invitation to pay additional fees dated Dec. 23, 2015, which issued during the prosecution of Applicant's PCT/IL2015/050923.
An Office Action dated Jan. 5, 2016, which issued during the prosecution of Japanese Patent Application No. 2013-519213.
An Office Action dated Feb. 25, 2016, which issued during the prosecution of U.S. Appl. No. 13/809,562.
An Office Action dated Feb. 18, 2016 which issued during the prosecution of Australian Patent Application No. 2012298197.
An International Search Report and a Written Opinion both dated Mar. 10, 2016, which issued during the prosecution of Applicant's PCT/IL2015/050923.
An Office Action dated Jul. 11, 2016 which issued during the prosecution of Australian Patent Application No. 2012298197.
An International Search Report and a Written Opinion both dated Jun. 9, 2016, which issued during the prosecution of Applicant's PCT/IL2015/050978.
An Office Action dated Jun. 27, 2016 which issued during the prosecution of Australian Patent Application No. 2015202032.
An Office Action dated May 24, 2016 which issued during the prosecution of Chinese Patent Application No. 2013800124154.
An English translation of an Office Action dated Mar. 24, 2015, which issued during the prosecution of Japanese Patent Application No. 519213/2013.
U.S. Appl. No. 61/636,751, filed Apr. 23, 2012.
U.S. Appl. No. 61/584,267, filed Jan. 8, 2012.
U.S. Appl. No. 61/526,717, filed Aug. 24, 2011.
U.S. Appl. No. 61/363,247, filed Jul. 11, 2010.
U.S. Appl. No. 61/714,813, filed Oct. 17, 2012.
An International Search Report and a Written Opinion both dated Jan. 23, 2013, which issued during the prosecution of Applicant's PCT/IL2012/000318.
An International Search Report and a Written Opinion both dated Dec. 5, 2011, which issued during the prosecution of Applicant's PCT/IL2011/000549.
An International Search Report and a Written Opinion both dated May 10, 2013 which issued during the prosecution of Applicant's PCT/IL2013/050030.
An International Search Report dated Jan. 8, 2013 which issued during the prosecution of Applicant's PCT/IL2012/000319.
An English translation of an Office Action dated Jul. 3, 2014 which issued during the prosecution of Chinese Patent Application 2011800437287.
An International Search Report and Written Opinion both dated Jul. 11, 2014, which issued during the prosecution of Applicant's PCT/IL 14/50299.
An International Preliminary Search Report dated Aug. 26, 2014, which issued during the prosecution of Applicant's PCT/IL2013/050030.
An International Preliminary Report dated Feb. 25, 2014 which issued during the prosecution of Applicant's PCT/IL2012/000319.

(56) References Cited

OTHER PUBLICATIONS

Written Opinion dated Jan. 8, 2013 which issued during the prosecution of Applicant's PCT/IL2012/000319.
An International Preliminary Report dated Feb. 25, 2014 which issued during the prosecution of Applicant's PCT/IL2012/000318.
An Office Action dated Apr. 5, 2014 which issued during the prosecution of Australian Patent Application No. 2011277949.
European Search Report dated Jun. 11, 2015 which issued during the prosecution of Applicant's European App No. 12826407.4.
An Office Action dated Oct. 13, 2016, which issued during the prosecution of U.S. Appl. No. 14/240,082.
An Office Action dated Nov. 22, 2016 which issued during the prosecution of Japanese Patent Application No. 550801/2014.
English Translation of Notice of Reasons for Refusal, mailed Sep. 6, 2016, issued in corresponding JP Application No. 2014-526597, 5 pages in English.
European Search Report dated Jan. 17, 2017, which issued during the prosecution of Applicant's European App No. 14769413.7.
An Office Action dated Mar. 20, 2017, which issued during the prosecution of U.S. Appl. No. 14/240,082.
European Search Report dated May 11, 2017, which issued during the prosecution of Applicant's European App No. 11806391.6.

\* cited by examiner

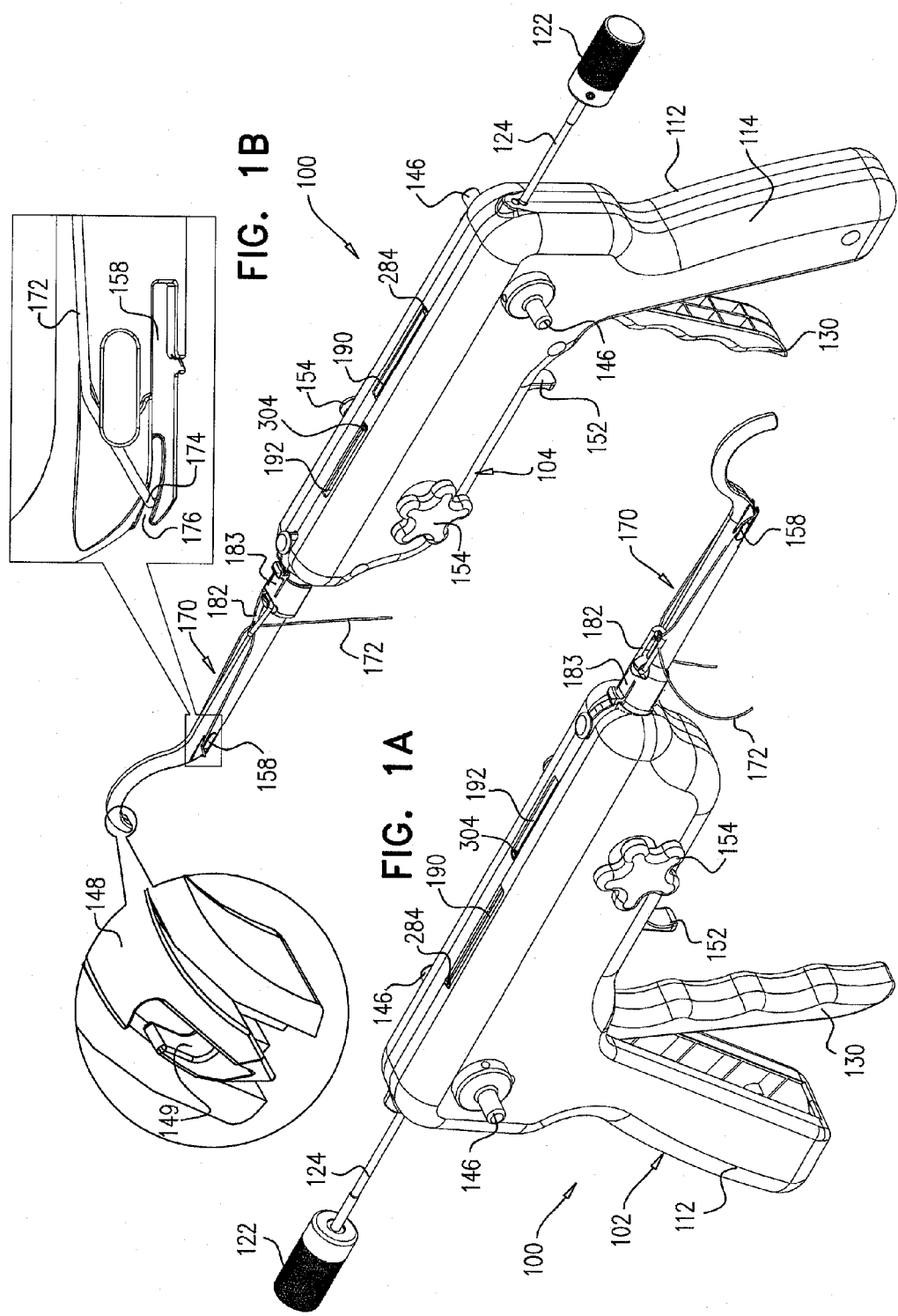

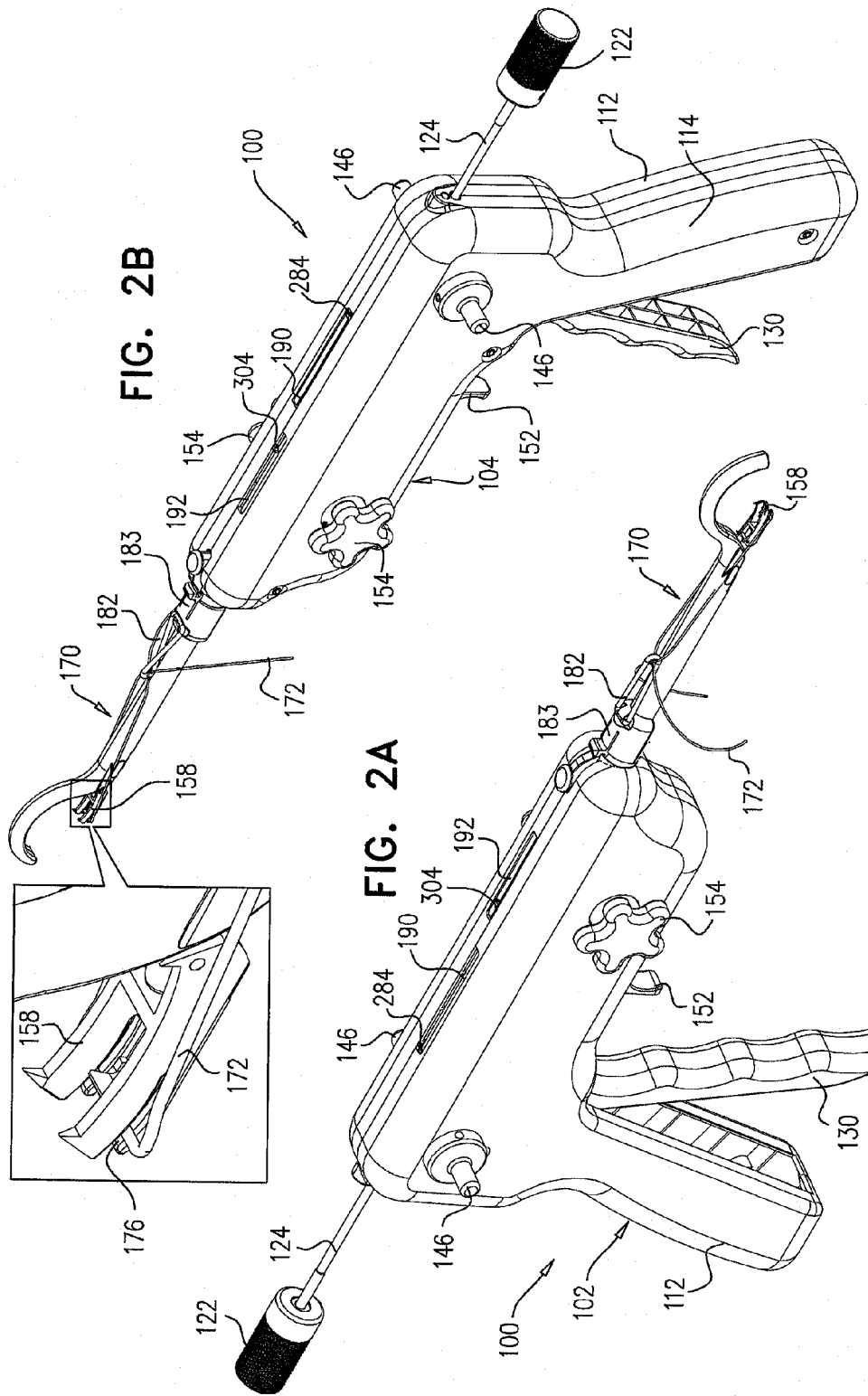

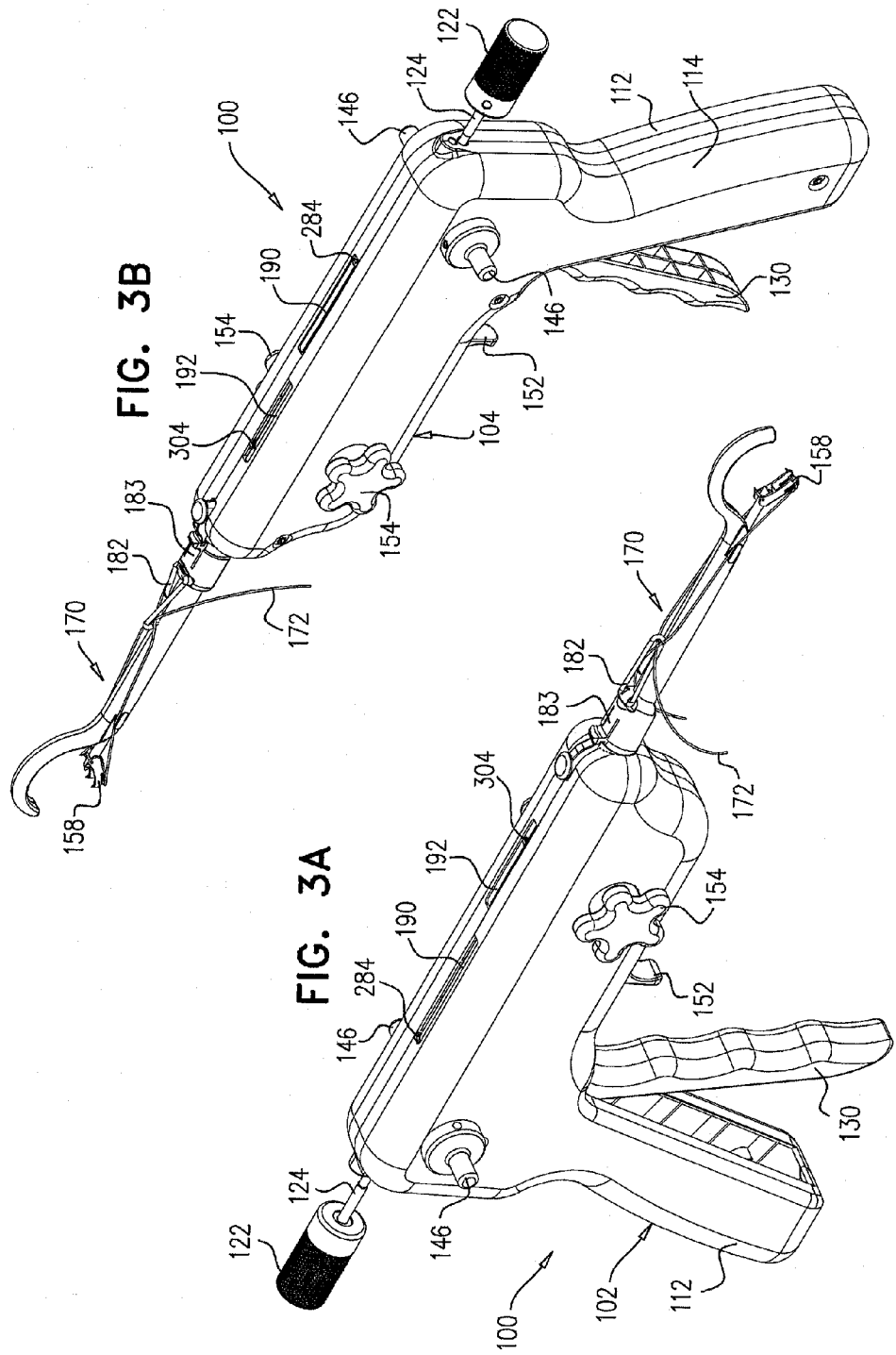

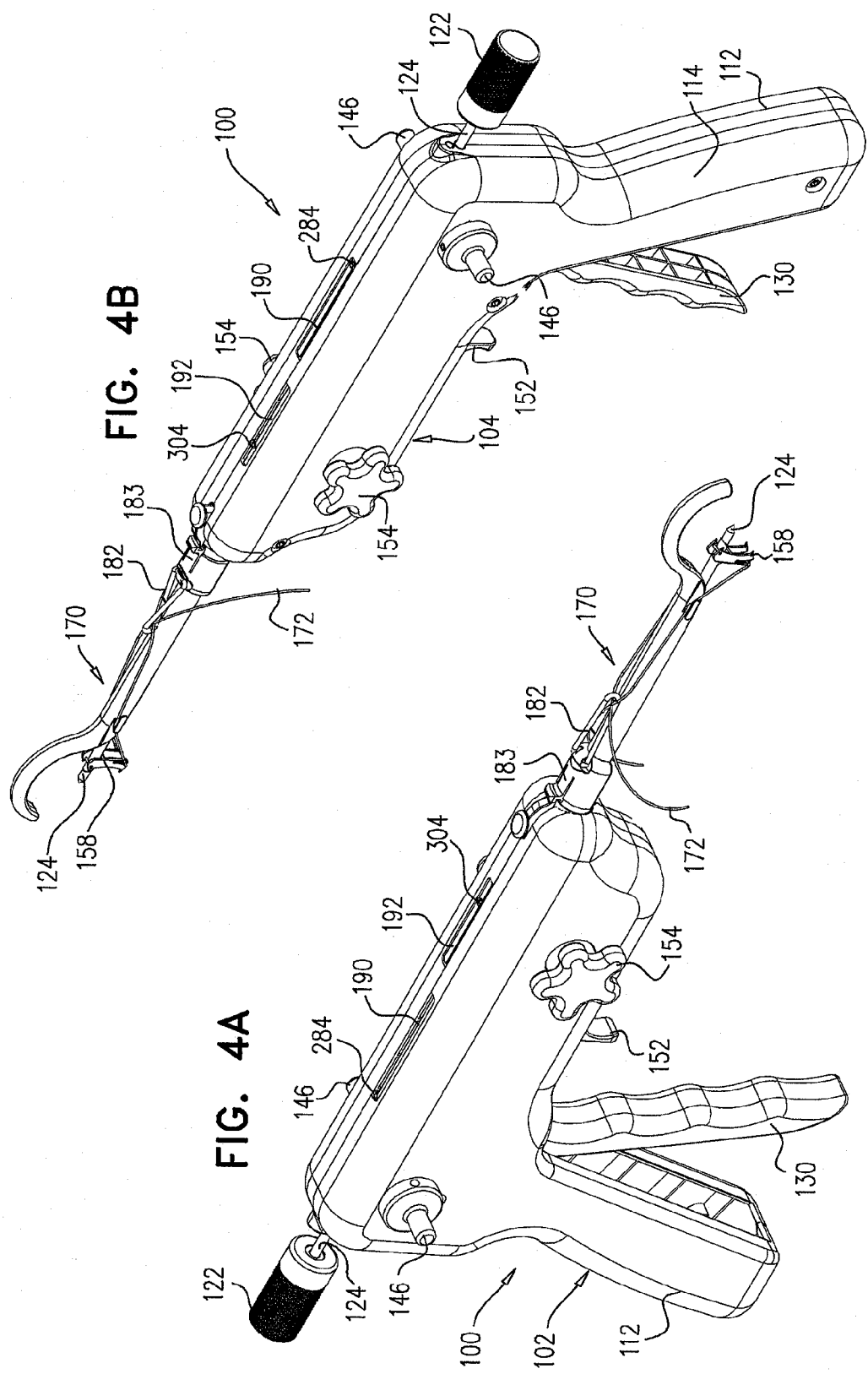

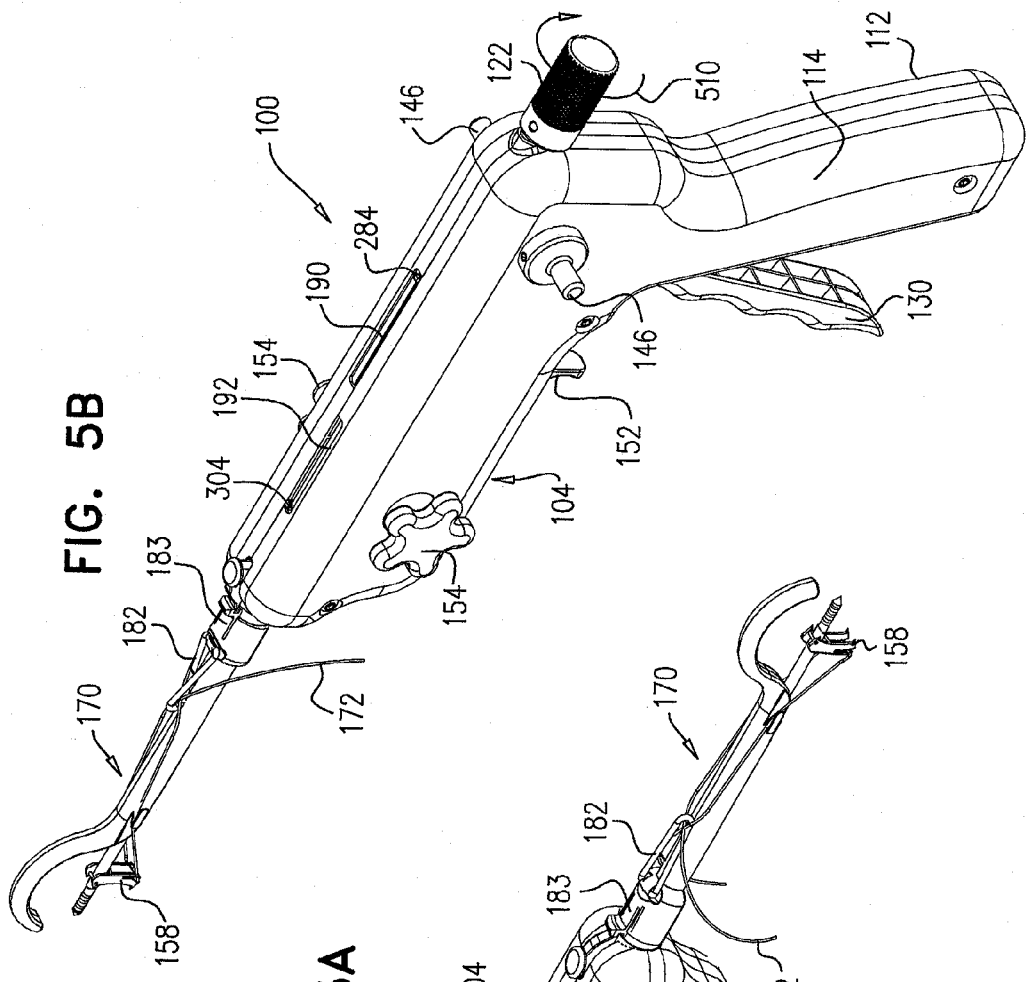
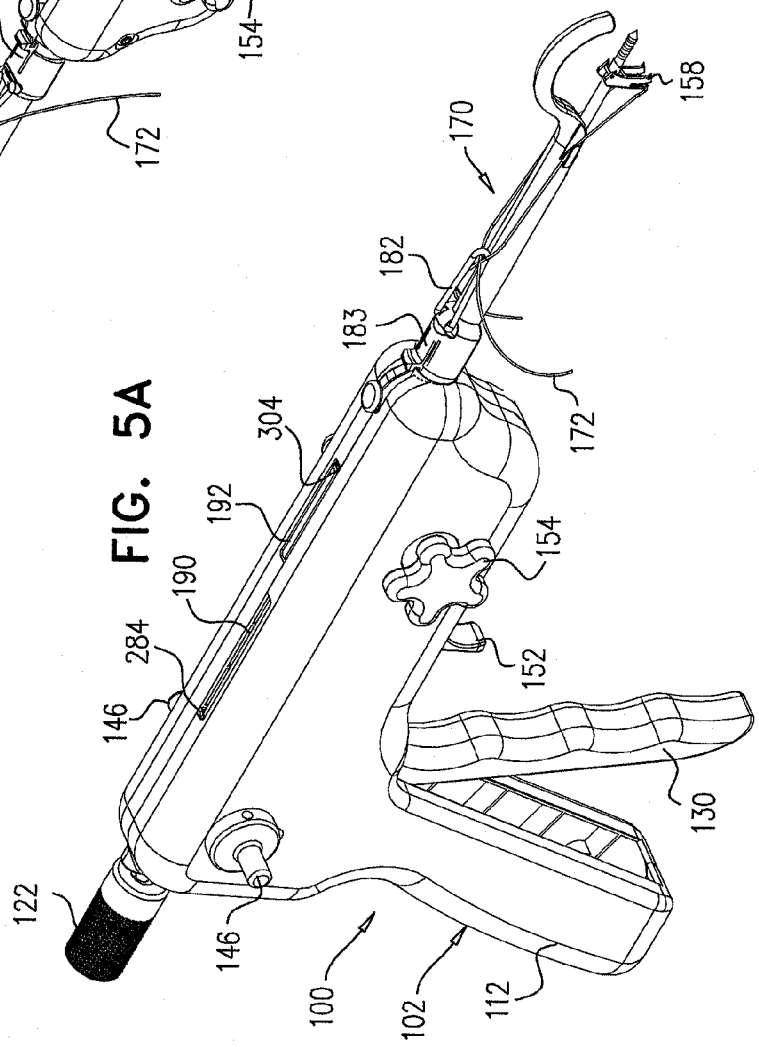

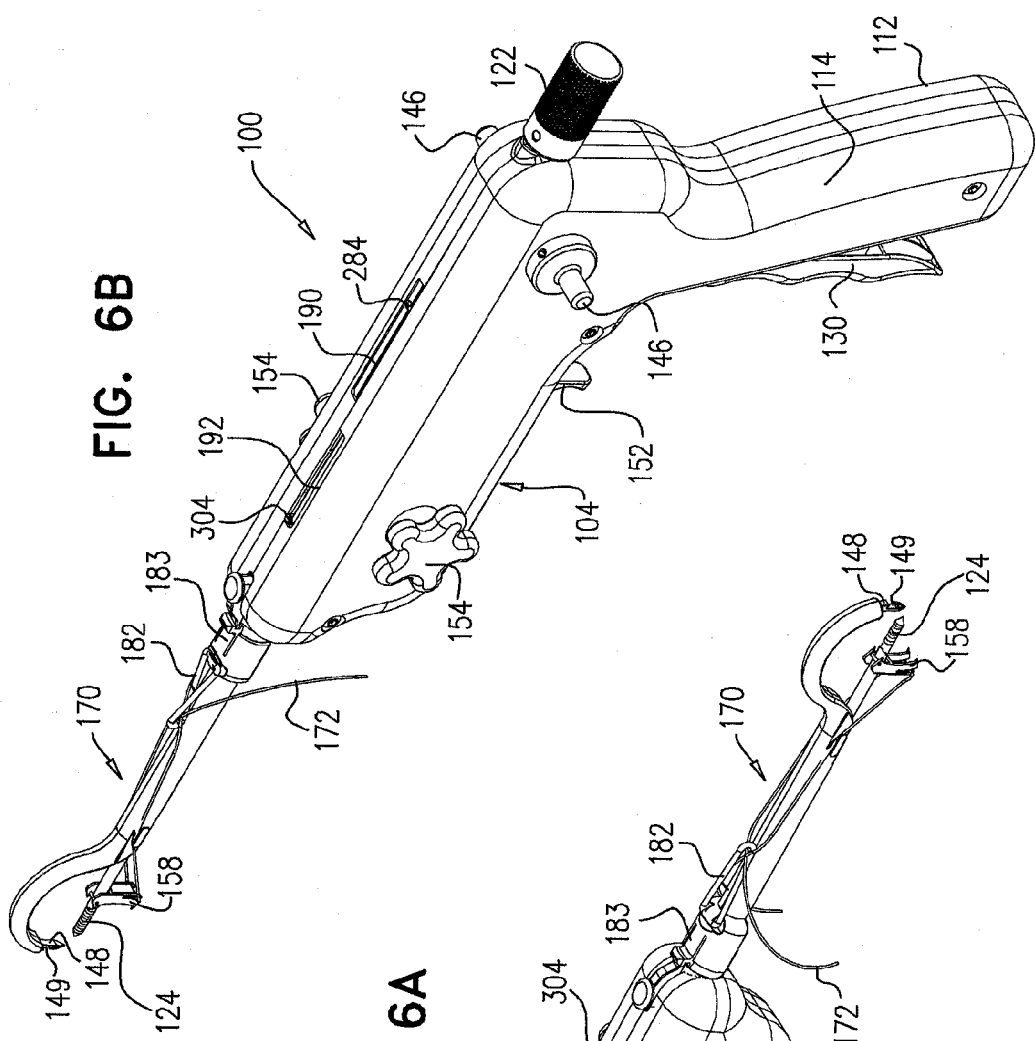
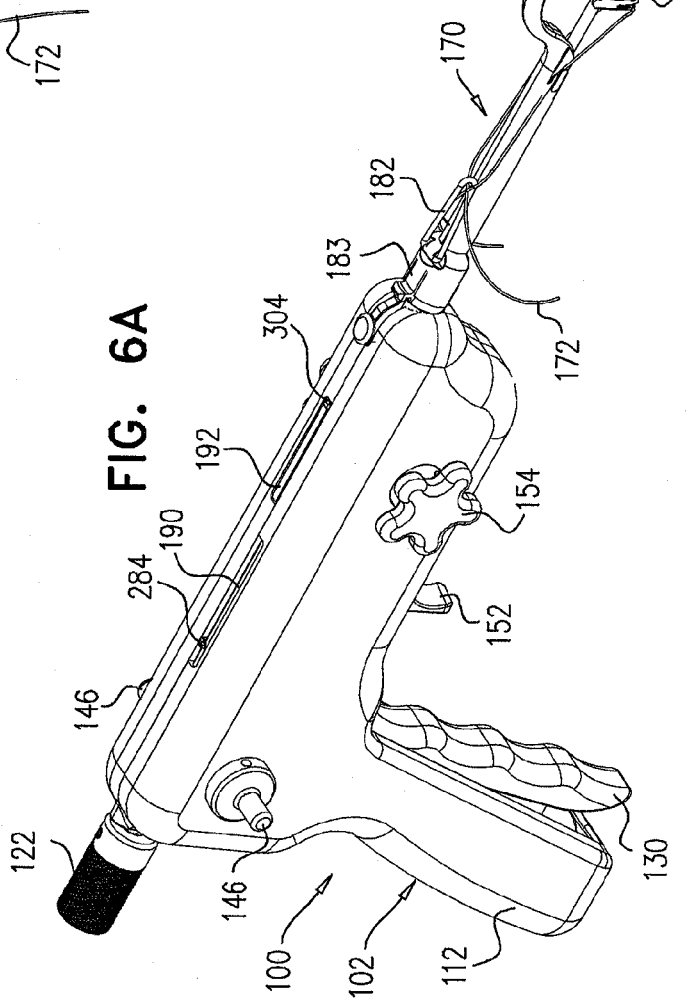

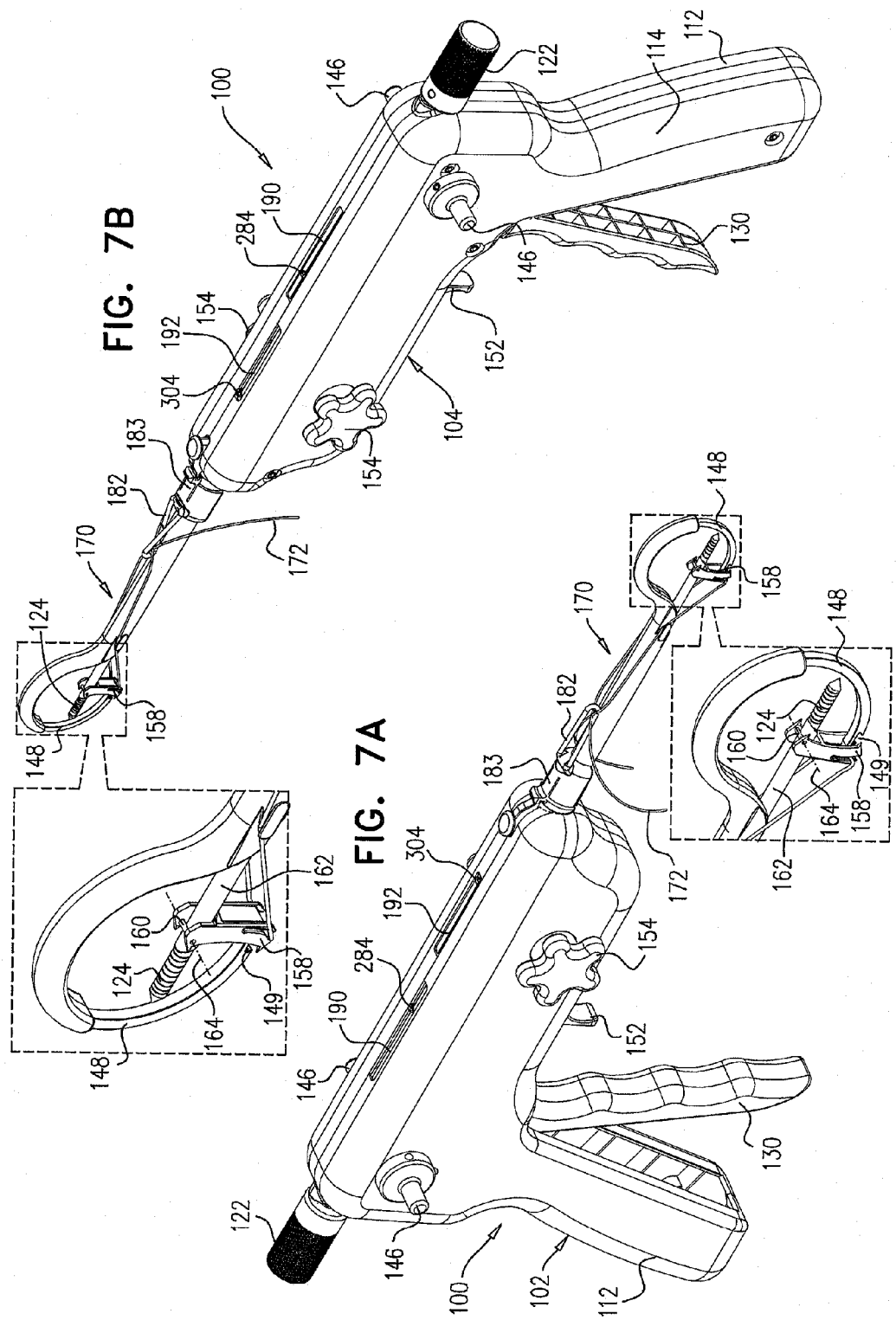

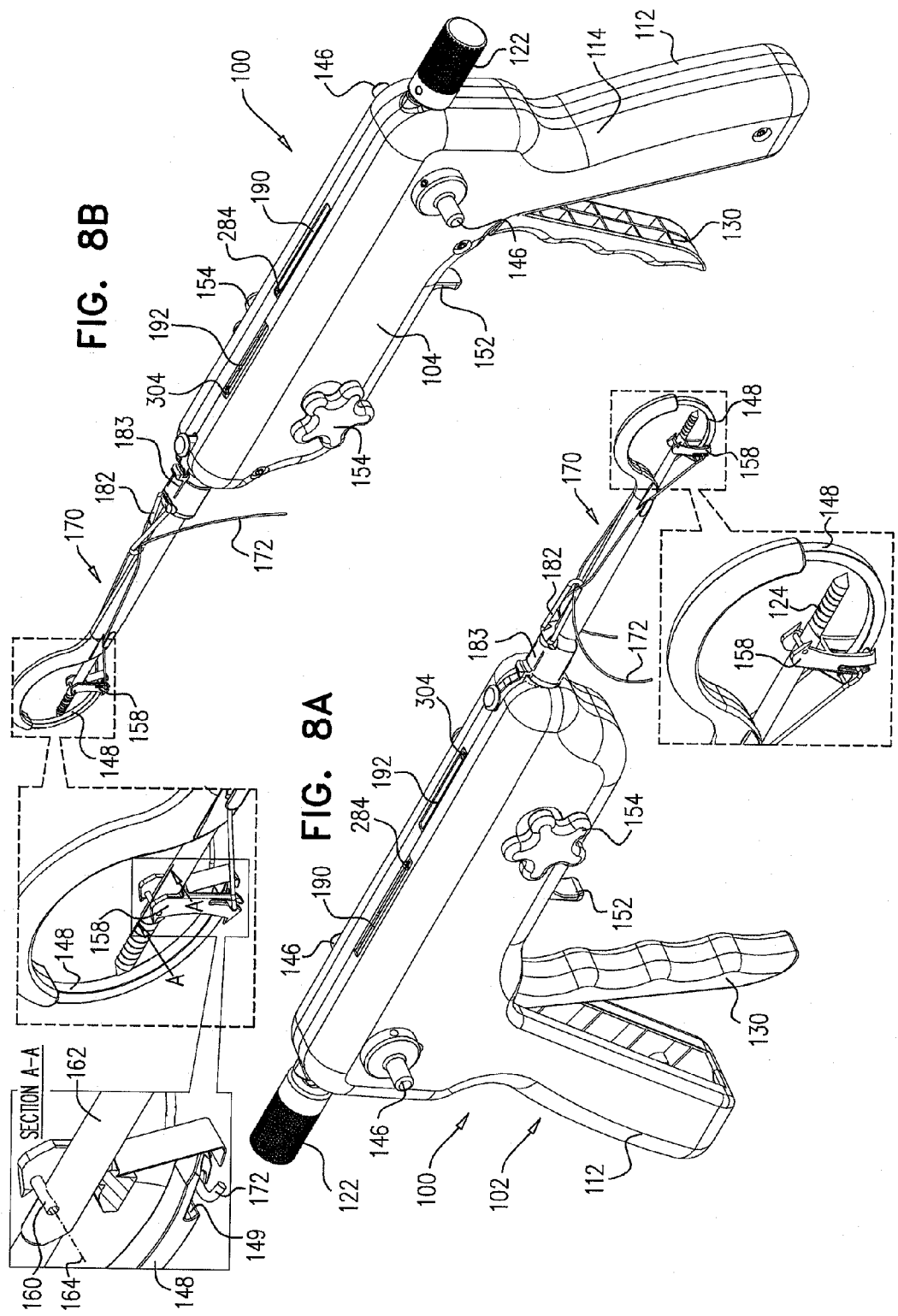

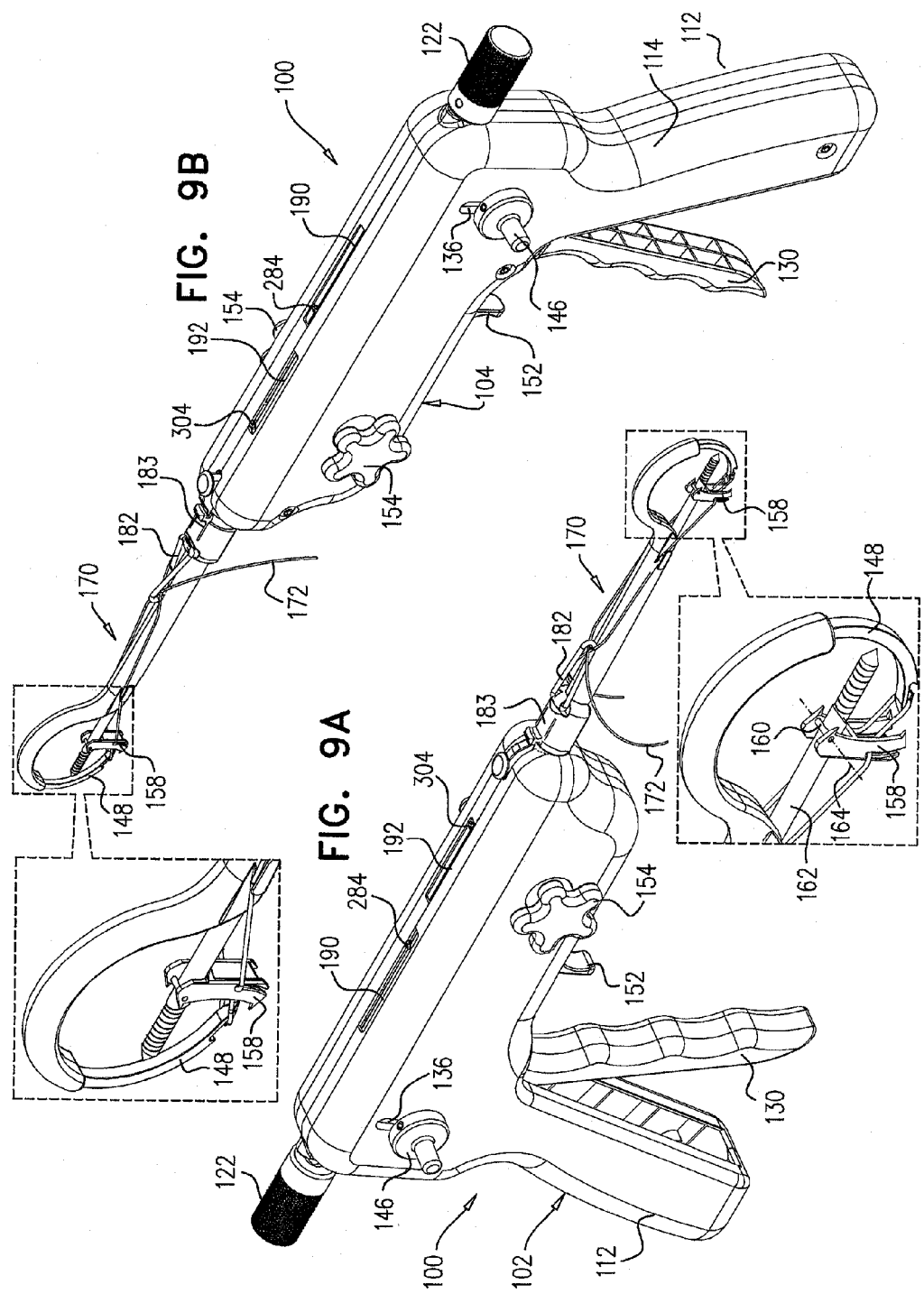

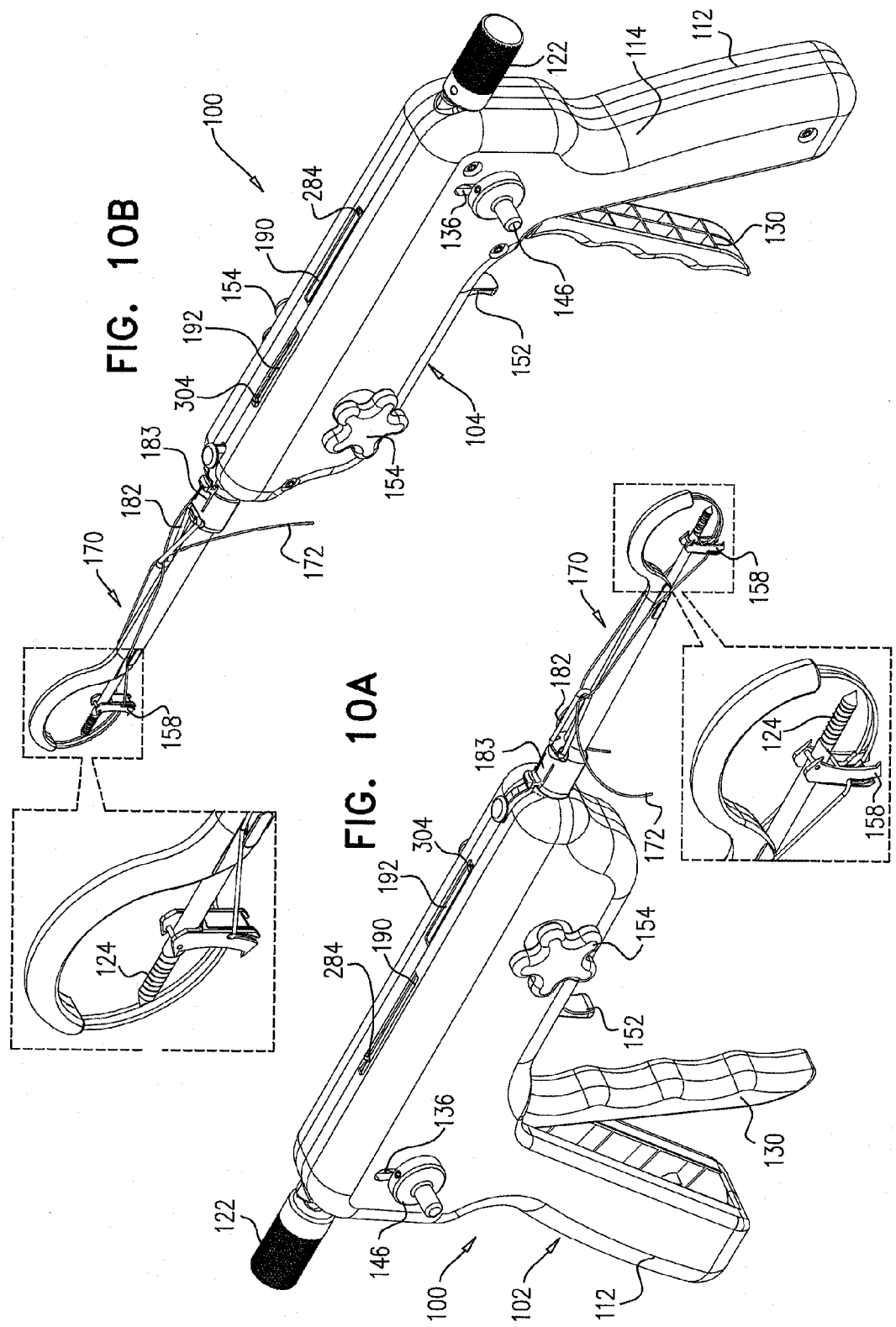

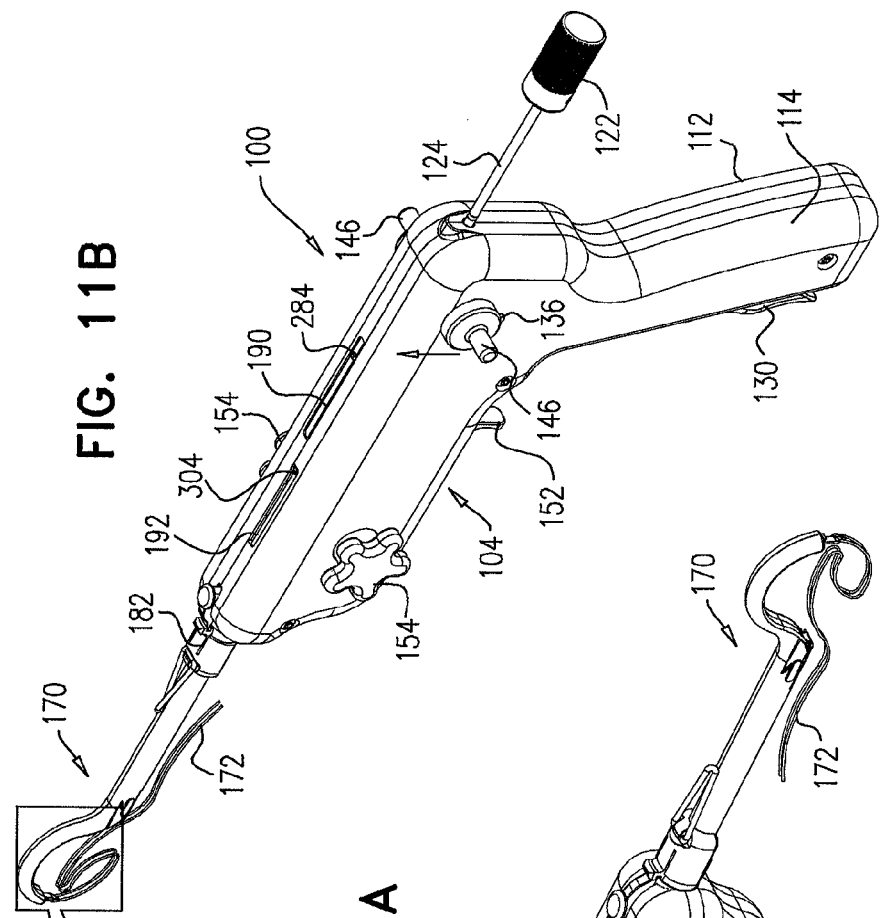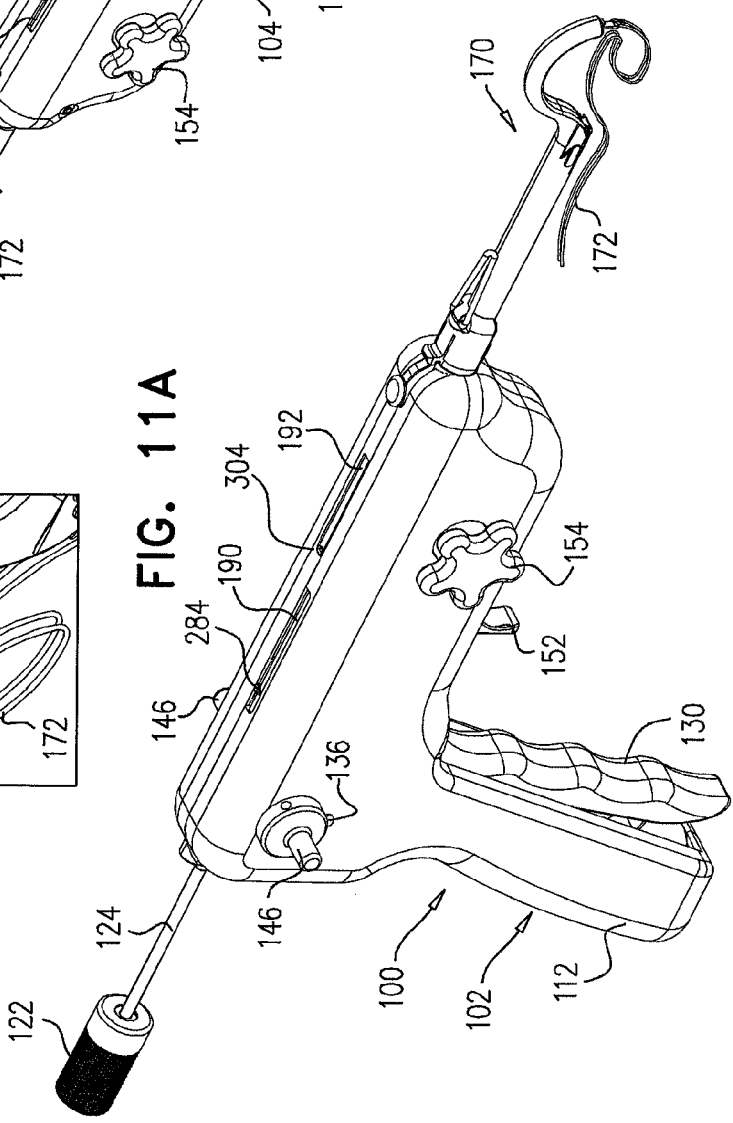

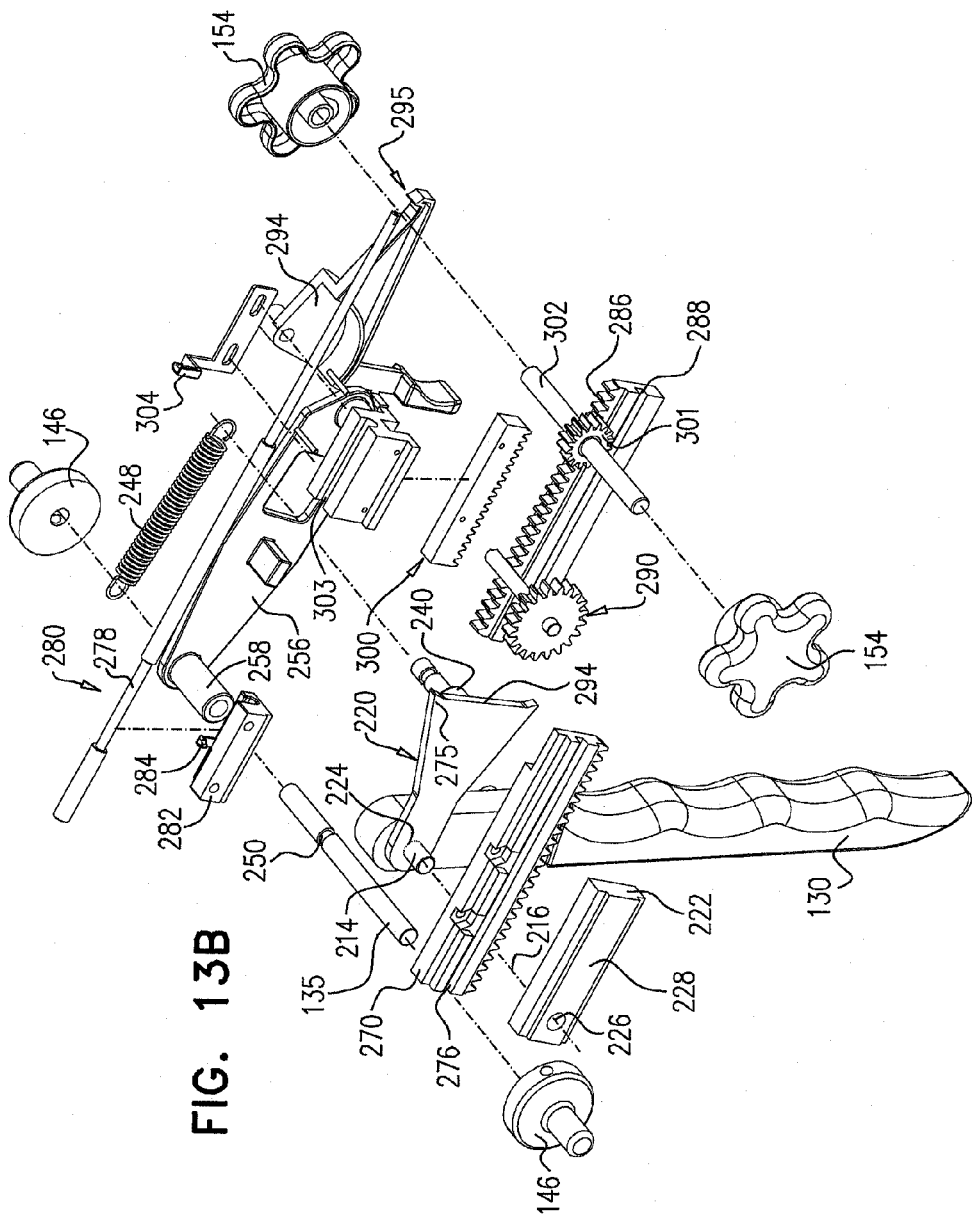

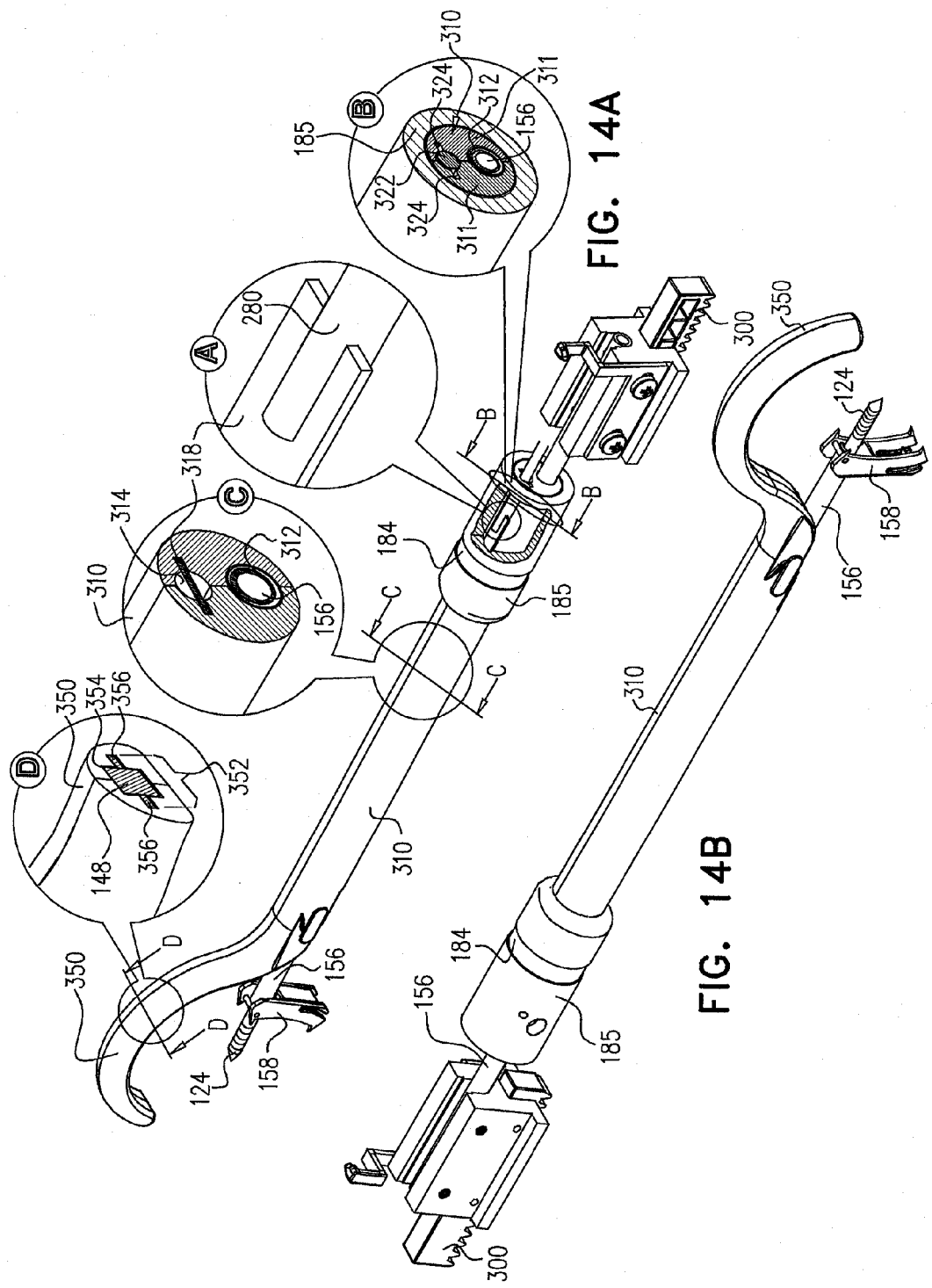

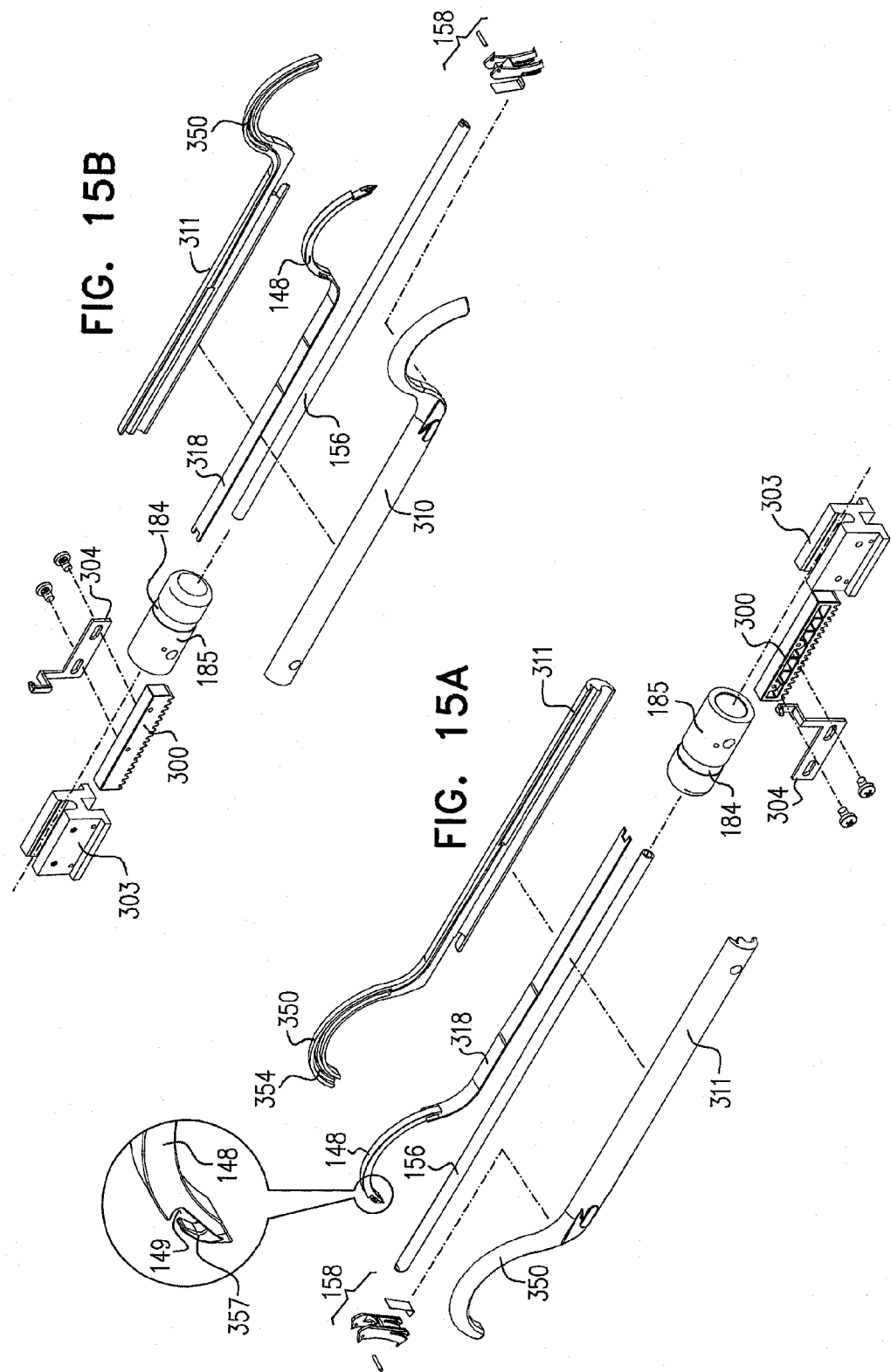

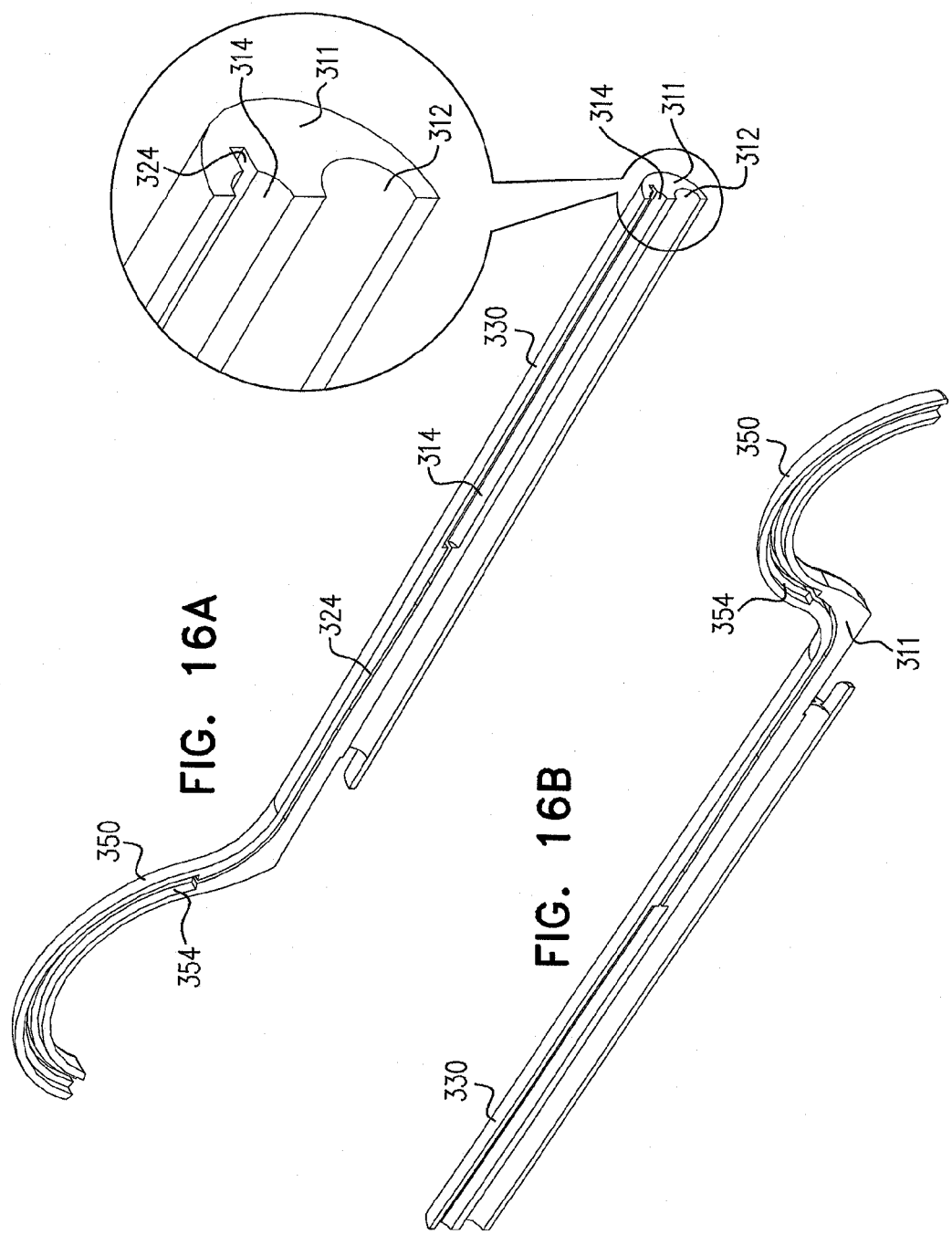

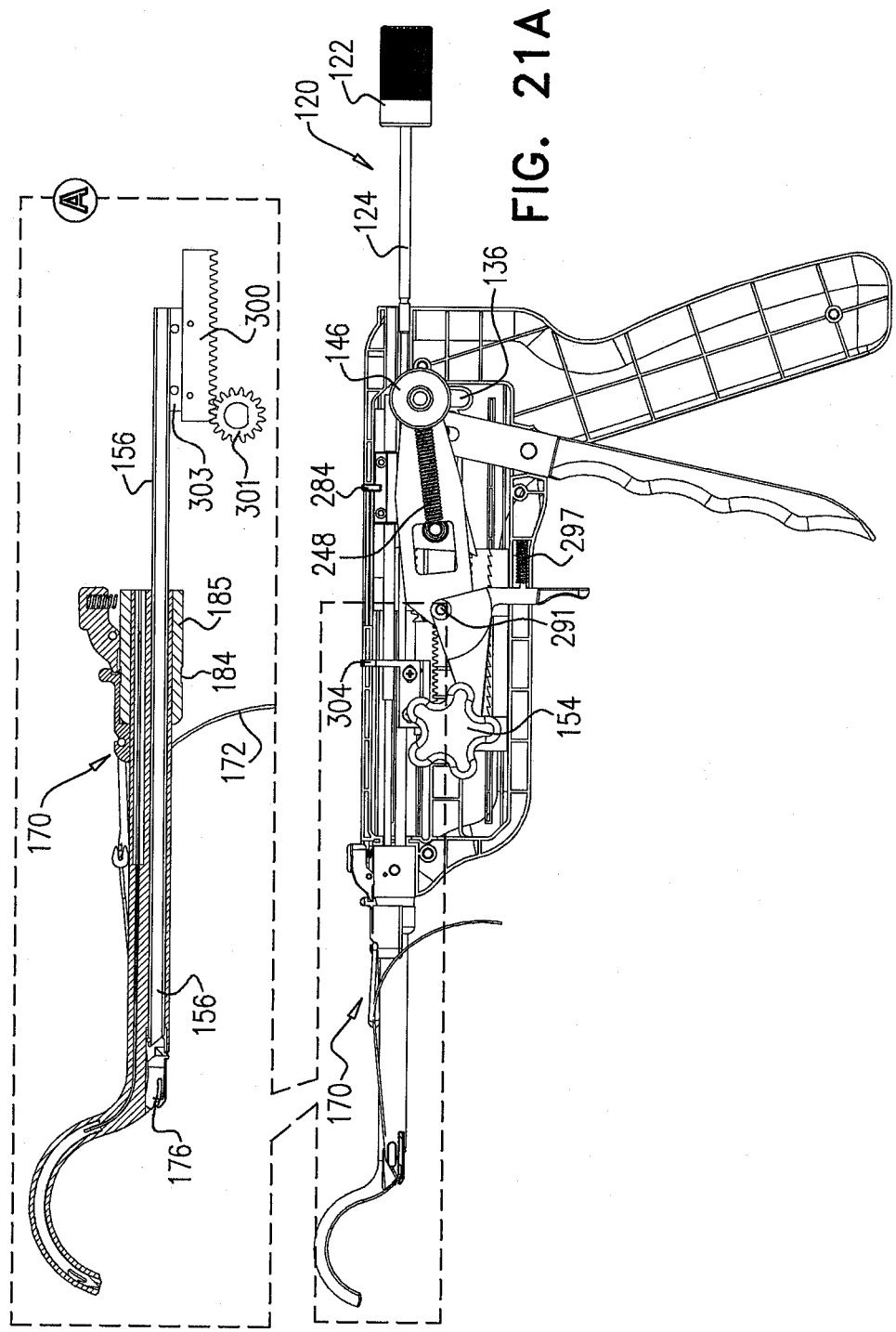

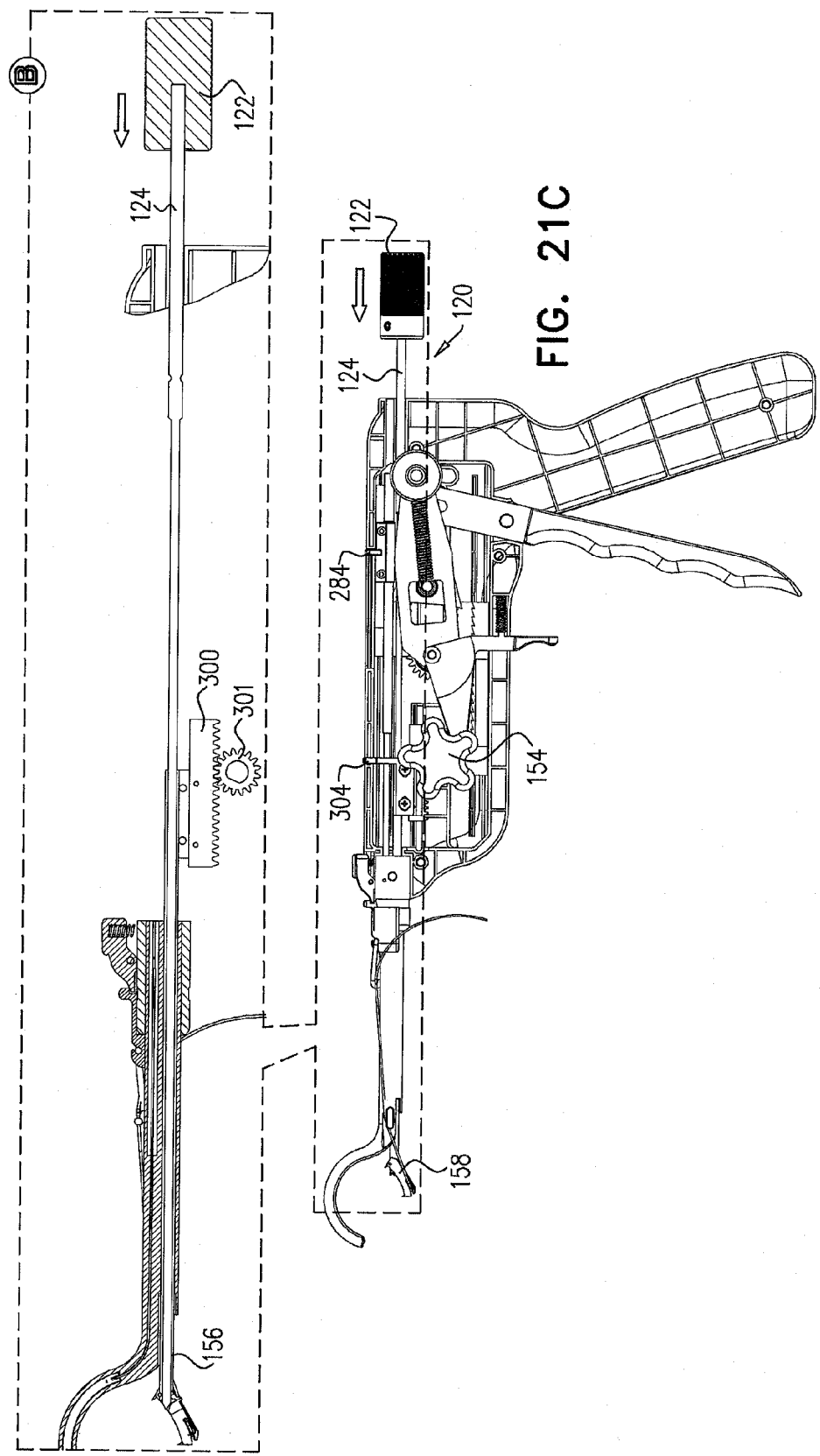

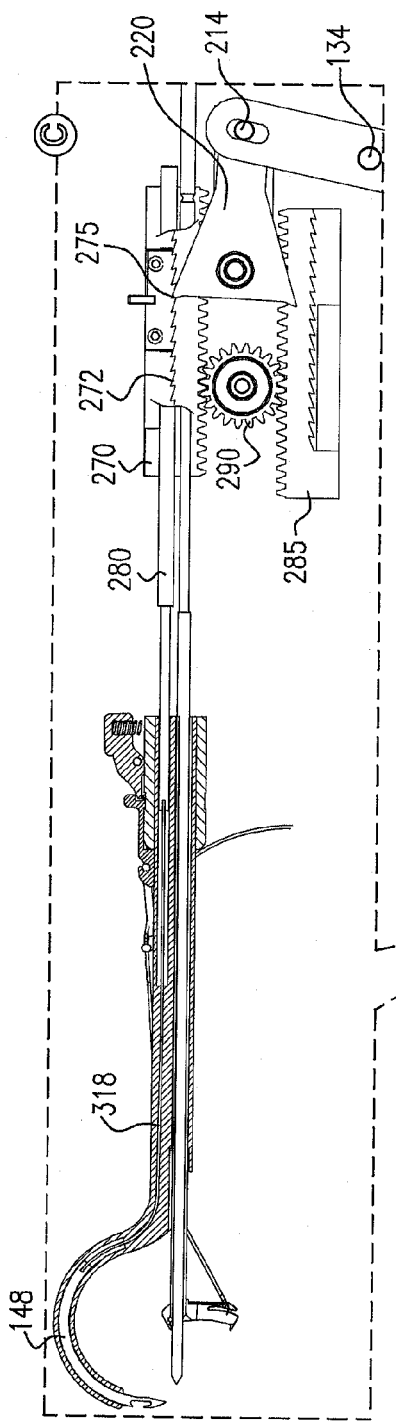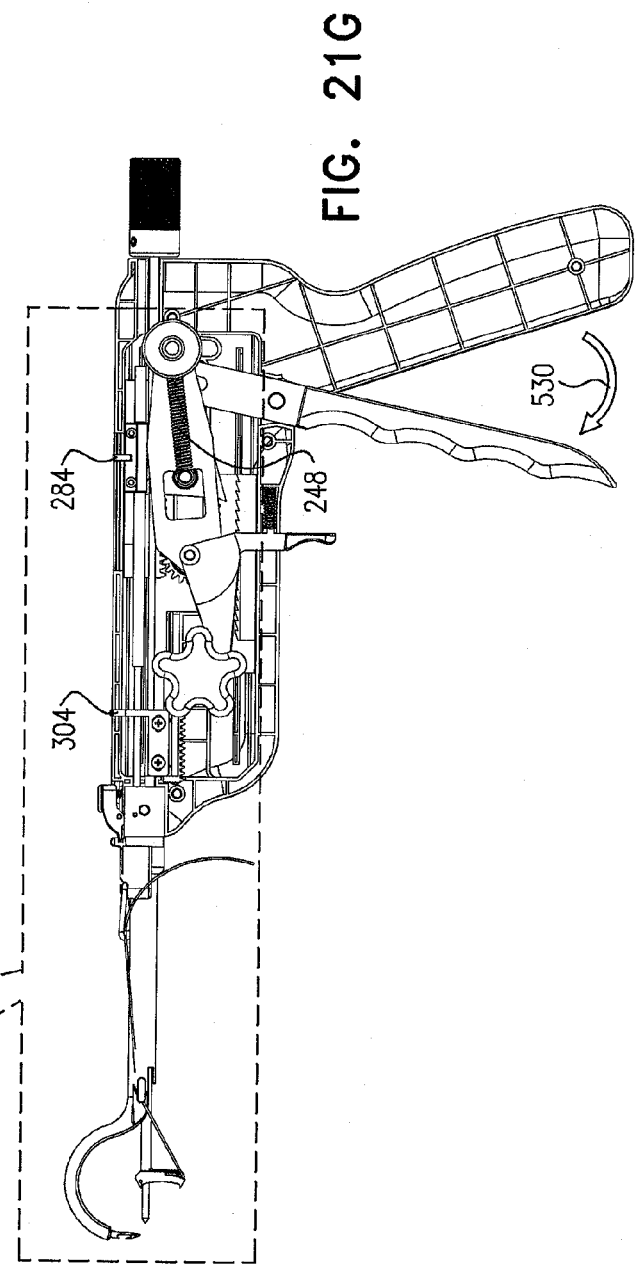
FIG. 21G

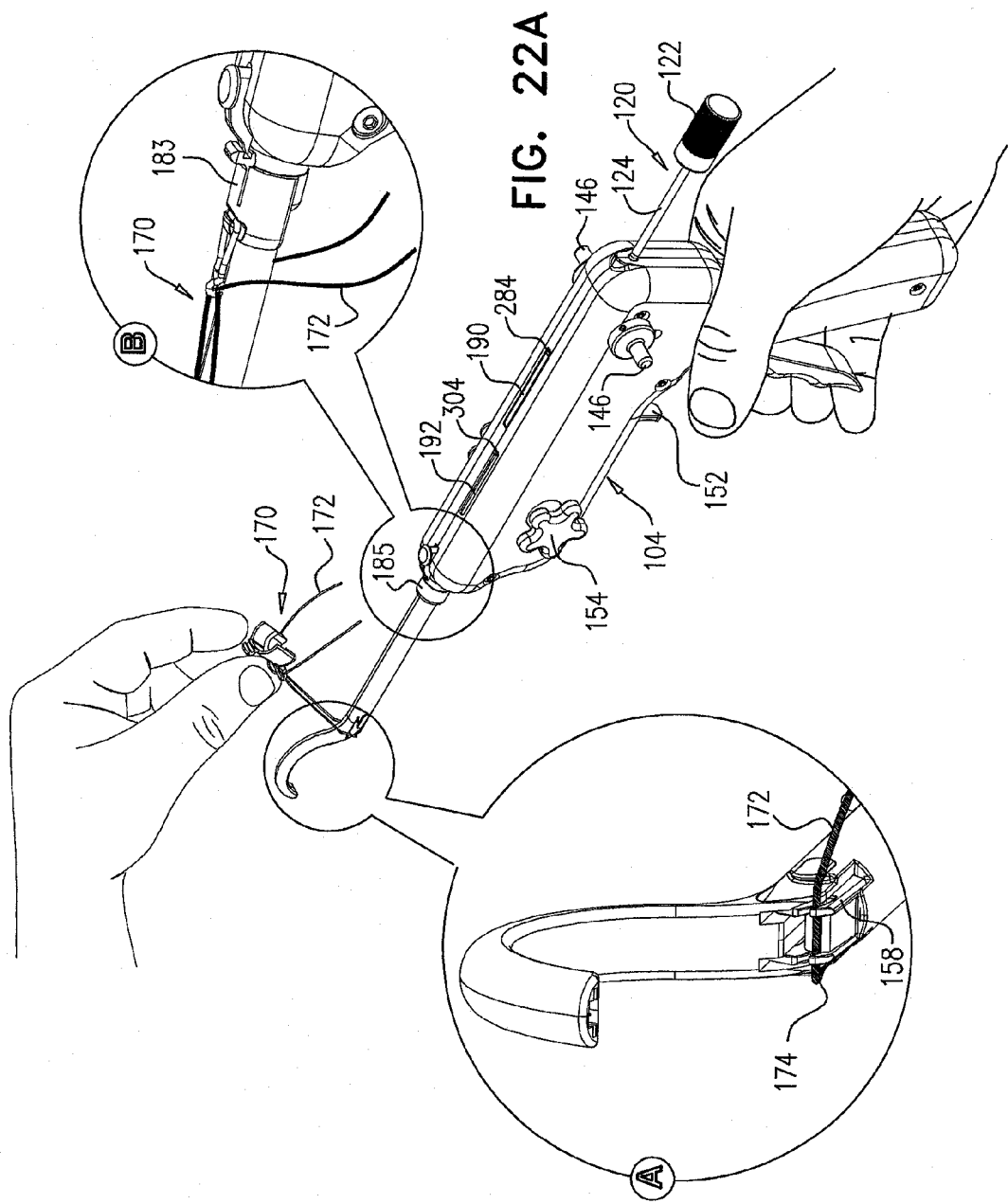

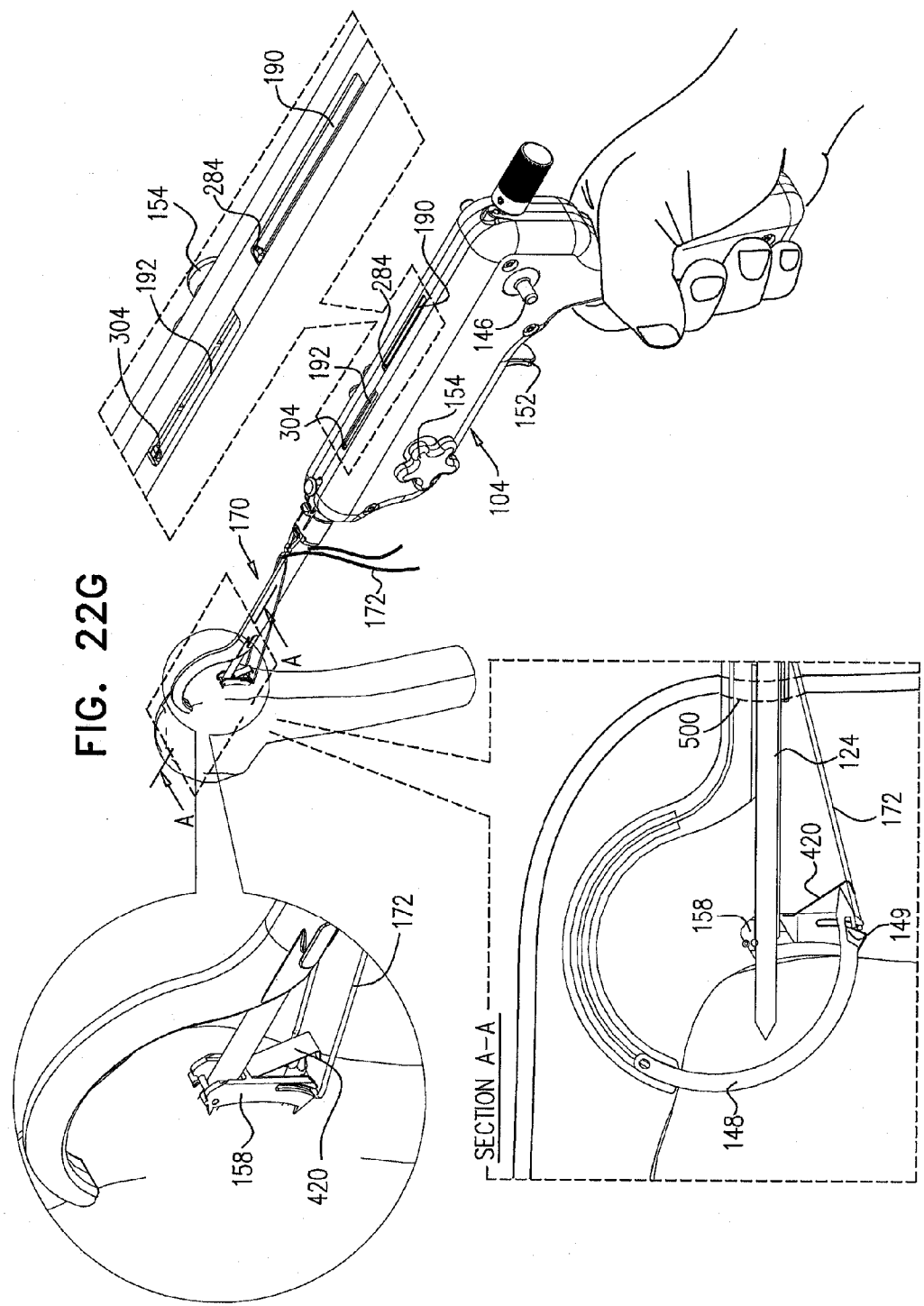

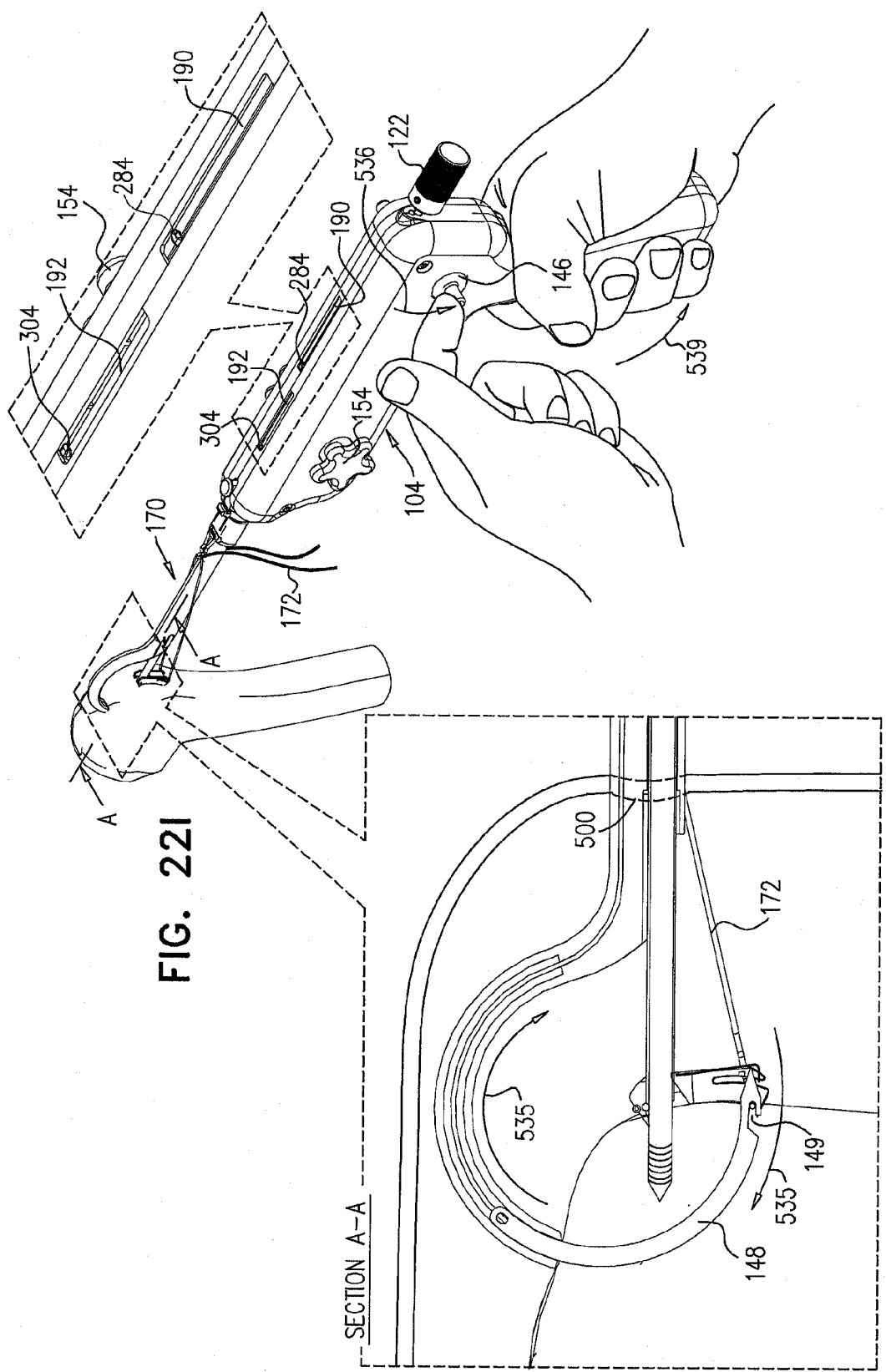

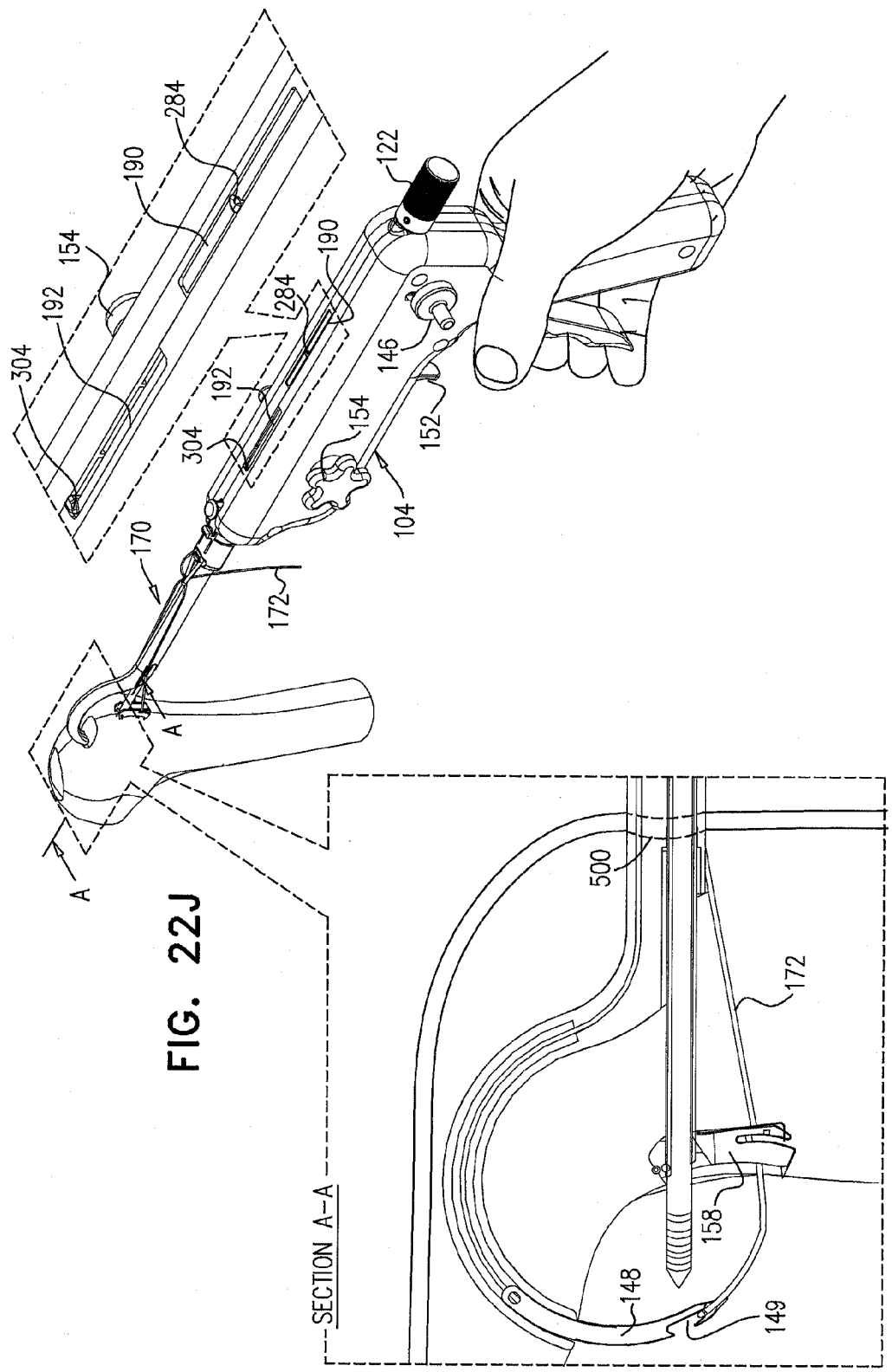

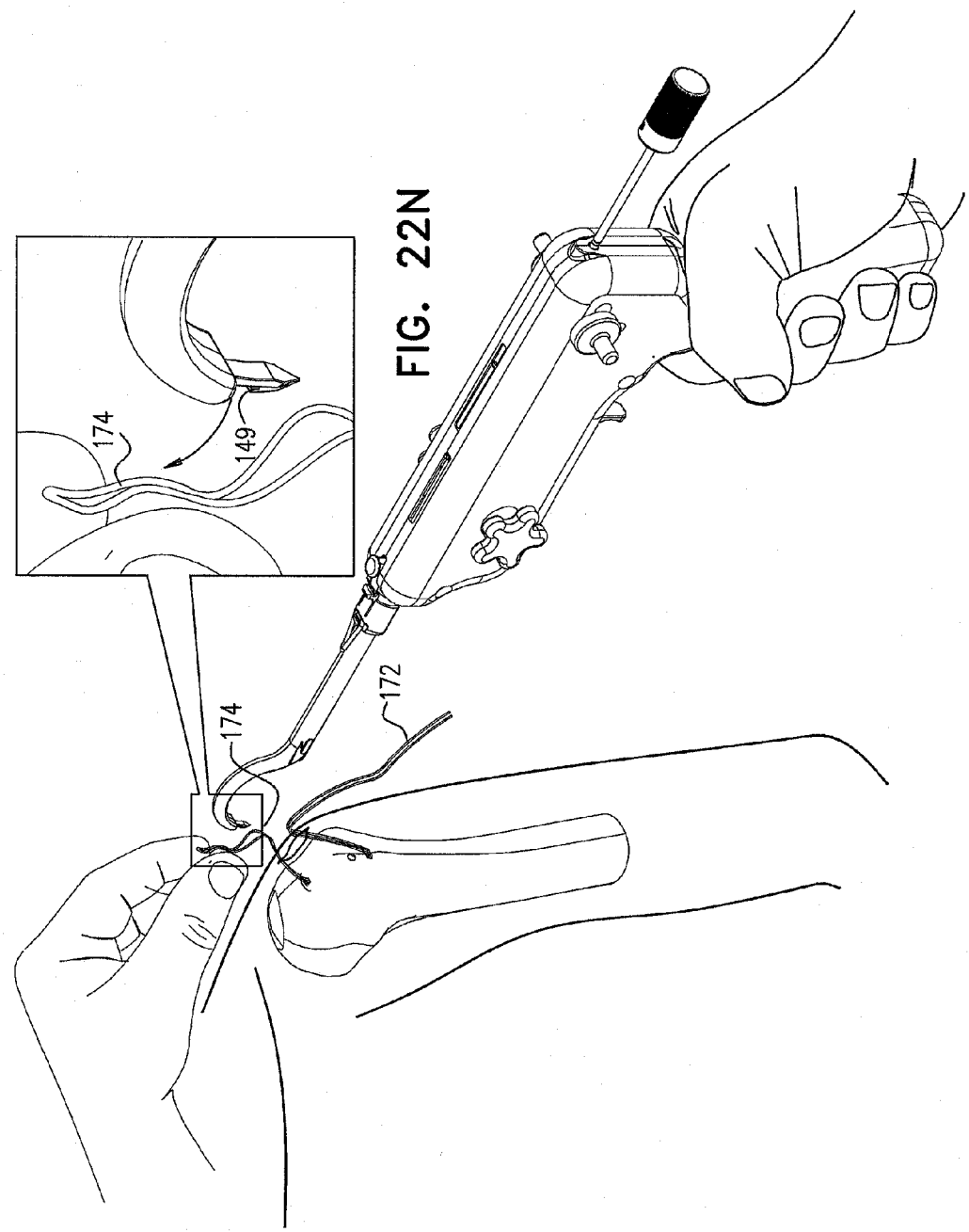

ARTHROSCOPIC SURGICAL DEVICE

REFERENCE TO RELATED APPLICATIONS

Reference is made to the following U.S. Provisional Patent Applications which are believed to be related to the present application, the contents of which are hereby incorporated by reference herein and priority of which is hereby claimed under 37 CFR 1.78(a)(4) and (5)(i):

U.S. Provisional Patent Application Ser. No. 61/636,751, entitled "Circular Bone Tunneling Device Employing a Stabilizing Element" and filed Apr. 23, 2012;

U.S. Provisional Patent Application Ser. No. 61/584,267, entitled "Circular Bone Tunneling Device" and filed Jan. 8, 2012; and U.S. Provisional Patent Application Ser. No. 61/526,717, entitled "Circular Bone Tunneling Device" and filed Aug. 24, 2011.

Reference is also made to Published PCT Patent Application No. WO 2012/007941, entitled "Circular Bone Tunneling Device" and filed Jul. 11, 2011, the contents of which are hereby incorporated by reference herein.

FIELD OF THE INVENTION

The present invention relates generally to arthroscopic surgical devices and more particularly to arthroscopic bone tunneling devices.

BACKGROUND OF THE INVENTION

Various types of arthroscopic surgical instruments are known for various applications including orthopedic surgery.

SUMMARY OF THE INVENTION

The present invention provides an arthroscopic surgical device for tunneling through hard tissue.

There is thus provided in accordance with a preferred embodiment of the present invention an arthroscopic surgical device for tunneling through hard tissue including an arcuate tunneling needle driver and a bone engagement element, the arcuate needle driver and the bone engagement element being joined together to provide a joined needle driver and bone engagement element having at least two different operative orientations including an arthroscopic operative orientation wherein the joined arcuate needle driver and bone engagement element has a trans-incision insertion cross-sectional footprint and a tunneling operative orientation suitable for tunneling, wherein the joined arcuate needle driver and bone engagement element has a tunneling cross-sectional footprint which is substantially greater than the insertion cross-sectional footprint.

There is also provided in accordance with another preferred embodiment of the present invention an arthroscopic surgical device for tunneling through hard tissue including an at least partially flexible arcuate tunneling needle driver and a bone engagement element, the at least partially flexible arcuate tunneling needle driver including a needle pushing element which is capable of assuming an arcuate orientation during needle driving operation thereof.

Preferably, the at least partially flexible arcuate needle driver and the bone engagement element are joined together to provide a joined arcuate needle driver and bone engagement element, the joined arcuate needle driver and bone engagement element having at least two different operative orientations including an arthroscopic operative orientation wherein the joined arcuate needle driver and bone engagement element has a trans-incision insertion cross-sectional footprint and a tunneling operative orientation suitable for tunneling, wherein the joined arcuate needle driver and bone engagement element has a tunneling cross-sectional footprint which is substantially greater than the insertion cross-sectional footprint.

Preferably, the trans-incision insertion cross-sectional footprint is suitable for arthroscopic insertion and the tunneling cross-sectional footprint is not suitable for arthroscopic insertion.

In accordance with a preferred embodiment of the present invention the bone engagement element is a rotatable bone engagement element.

In accordance with a preferred embodiment of the present invention the arthroscopic surgical device for tunneling through hard tissue also includes a bone engaging pin driving assembly including an elongate bone engaging pin. Additionally, the bone engaging pin includes a tapered screw threading.

Preferably, the arcuate tunneling needle driver includes a hand-engageable ratchet handle arranged for reciprocal motion about an axis and a selectable direction ratchet gear shaft.

In accordance with a preferred embodiment of the present invention the arthroscopic surgical device for tunneling through hard tissue also includes an arcuate tunneling needle.

Preferably, the arcuate tunneling needle driver includes a flexible needle driving strip and a generally rigid flexible needle driving strip driving shaft, mounted at a rear end of flexible needle driving strip.

In accordance with a preferred embodiment of the present invention the arthroscopic surgical device for tunneling through hard tissue also includes an arcuate needle storage and guiding portion, formed with an arcuate bore. Additionally or alternatively, the arthroscopic surgical device for tunneling through hard tissue also includes a bone engagement element positioning assembly including a finger-engageable release trigger, finger engageable bone engagement element advancement knobs and a hollow bone engagement element driving shaft.

Preferably, the arthroscopic surgical device for tunneling through hard tissue also includes a needle and suture mounting assembly.

In accordance with a preferred embodiment of the present invention the arthroscopic surgical device for tunneling through hard tissue also includes a bone suture insertion assembly including a looped suture and a tensionable resilient elongate element connected to the looped suture for selectable tensioning of the looped suture.

There is further provided in accordance with yet another preferred embodiment of the present invention a bone suture insertion assembly for use with an arthroscopic surgical device for tunneling through hard tissue, the assembly including a looped suture and a tensionable resilient elongate element connected to the looped suture for selectable tensioning of the looped suture.

There is even further provided in accordance with still another embodiment of the present invention an arthroscopic surgical method for tunneling through hard tissue including providing an arthroscopic surgical device including an arcuate tunneling needle, an arcuate tunneling needle driver and a rotatable bone engagement element, joining the arcuate tunneling needle driver and the rotatable bone engagement element to provide a joined needle driver and bone engagement element having multiple different operative orientations, mounting a suture mounting assembly, including a suture, onto the arthroscopic surgical device, inserting a forward portion of the arthroscopic surgical device through an incision such that the forward portion engages the hard tissue, extending the arcuate tunneling needle through the hard tissue, engaging a forward end of the suture with the arcuate tunneling needle and retracting the arcuate tunneling needle through the hard tissue, thereby pulling the suture through the hard tissue.

Preferably, the multiple different operative orientations include at least an arthroscopic operative orientation wherein the joined arcuate needle driver and bone engagement element has a trans-incision insertion cross-sectional footprint and a tunneling operative orientation suitable for tunneling, wherein the joined arcuate needle driver and bone engagement element has a tunneling cross-sectional footprint which is substantially greater than the insertion cross-sectional footprint.

BRIEF DESCRIPTION OF THE DRAWINGS

The present invention will be understood and appreciated from the following detailed description, taken in conjunction with the drawings in which:

FIGS. 1A & 1B are simplified pictorial illustrations of an arthroscopic surgical device constructed and operative in accordance with a preferred embodiment of the present invention, showing opposite views in a first operative orientation;

FIGS. 2A & 2B are simplified pictorial illustrations of an arthroscopic surgical device constructed and operative in accordance with a preferred embodiment of the present invention, showing opposite views in a second operative orientation;

FIGS. 3A & 3B are simplified pictorial illustrations of an arthroscopic surgical device constructed and operative in accordance with a preferred embodiment of the present invention, showing opposite views in a third operative orientation;

FIGS. 4A & 4B are simplified pictorial illustrations of an arthroscopic surgical device constructed and operative in accordance with a preferred embodiment of the present invention, showing opposite views in a fourth operative orientation;

FIGS. 5A & 5B are simplified pictorial illustrations of an arthroscopic surgical device constructed and operative in accordance with a preferred embodiment of the present invention, showing opposite views in a fifth operative orientation;

FIGS. 6A & 6B are simplified pictorial illustrations of an arthroscopic surgical device constructed and operative in accordance with a preferred embodiment of the present invention, showing opposite views in a sixth operative orientation;

FIGS. 7A & 7B are simplified pictorial illustrations of an arthroscopic surgical device constructed and operative in accordance with a preferred embodiment of the present invention, showing opposite views in a seventh operative orientation;

FIGS. 8A & 8B are simplified pictorial illustrations of an arthroscopic surgical device constructed and operative in accordance with a preferred embodiment of the present invention, showing opposite views in an eighth operative orientation;

FIGS. 9A & 9B are simplified pictorial illustrations of an arthroscopic surgical device constructed and operative in accordance with a preferred embodiment of the present invention, showing opposite views in a ninth operative orientation;

FIGS. 10A & 10B are simplified pictorial illustrations of an arthroscopic surgical device constructed and operative in accordance with a preferred embodiment of the present invention, showing opposite views in a tenth operative orientation;

FIGS. 11A & 11B are simplified pictorial illustrations of an arthroscopic surgical device constructed and operative in accordance with a preferred embodiment of the present invention, showing opposite views in an eleventh operative orientation;

FIGS. 13A and 13B are simplified exploded view illustrations of a portion of the arthroscopic surgical device of FIGS. 1A-12, showing opposite views;

FIGS. 14A and 14B are simplified illustrations of another portion of the arthroscopic surgical device of FIGS. 1A-12, showing opposite views;

FIGS. 15A and 15B are simplified exploded view illustrations of the portion of the arthroscopic surgical device of FIGS. 14A & 14B, showing opposite views;

FIGS. 16A and 16B are simplified illustrations of part of the portion of the arthroscopic surgical device of FIGS. 14A-15B, showing opposite views;

FIGS. 21A, 21B, 21C, 21D, 21E, 21F, 21G, 21H, 21I, 21J, 21K, 21L, 21M and 21N are respective simplified illustrations of displacement of various part of the arthroscopic surgical device of FIGS. 1A-20C during operation thereof; and FIGS. 22A, 22B, 22C, 22D, 22E, 22F, 22G, 22H, 22I, 22J, 22K, 22L, 22M and 22N are simplified illustrations of operation of the arthroscopic surgical device of FIGS. 1A-21N in a clinical context.

DETAILED DESCRIPTION OF PREFERRED EMBODIMENTS

Figure 12:
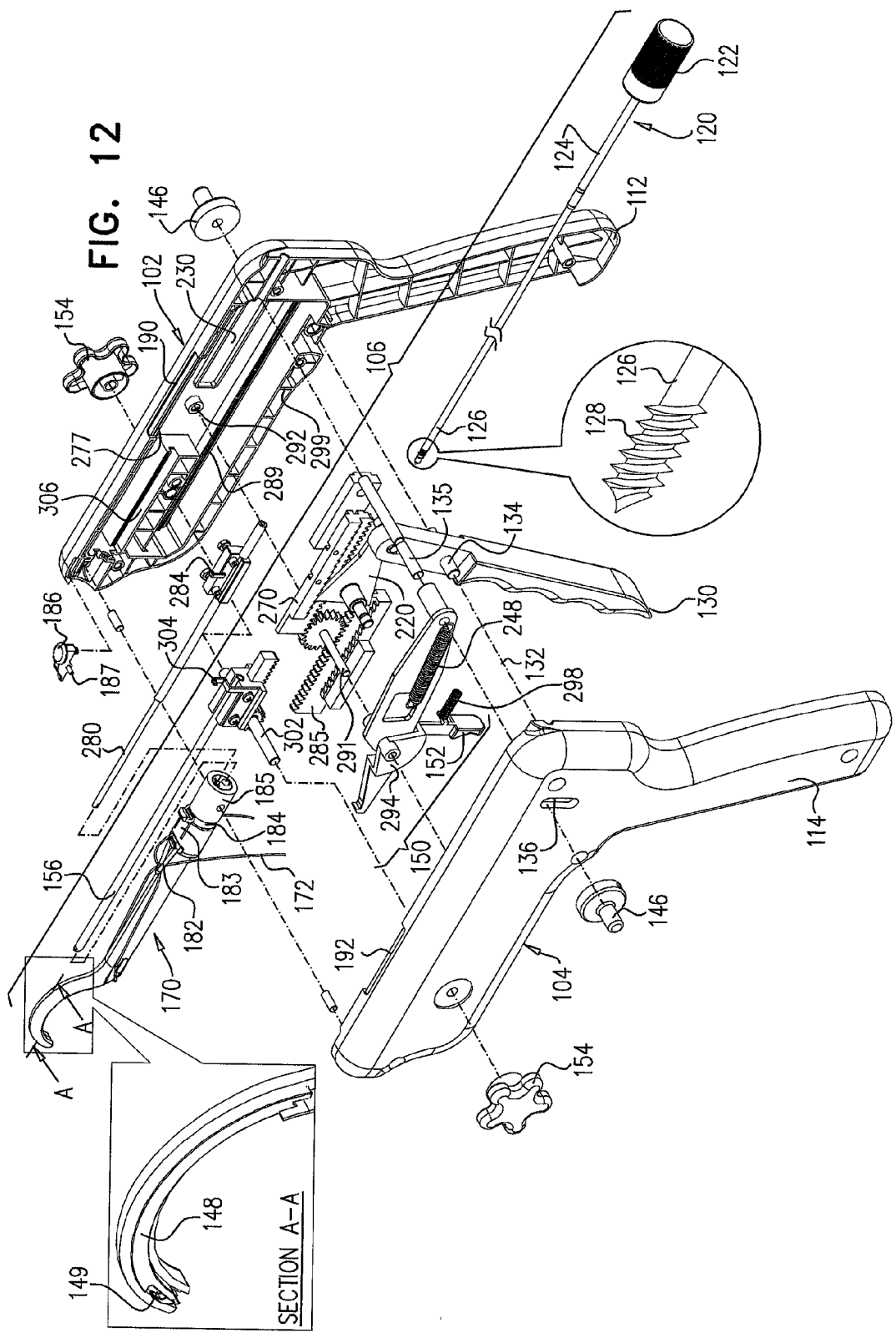
FIG. 12 is a simplified exploded view illustration of the arthroscopic surgical device of FIGS. 1A-11B in the first operative orientation.

Reference is now made to FIGS. 1A & 1B, which are simplified pictorial illustrations of an arthroscopic surgical device constructed and operative in accordance with a preferred embodiment of the present invention, showing opposite views in a first operative orientation, and to FIG. 12, which is a simplified exploded view illustration of the arthroscopic surgical device of FIGS. 1A-11B.

As seen in FIGS. 1A, 1B and 12, an arthroscopic surgical device 100 according to a preferred embodiment of the present invention includes a housing portion, preferably formed of right and left housing elements 102 and 104, and a multiple action driving assembly 106. The housing portion includes a handle portion, which is defined by respective right and left housing element handle portions 112 and 114, respectively.

The multiple action driving assembly 106 preferably includes a bone-engaging pin driving assembly 120 preferably including a knurled knob 122 and an elongate bone-engaging pin 124, extending forwardly therefrom, having a pointed forward end 126 which may be formed with a tapered screw threading 128.

The multiple action driving assembly 106 preferably includes a hand-engageable ratchet handle 130 which is arranged for reciprocal motion about an axis 132 defined by a shaft 134. A selectable direction ratchet gear shaft 135 extends through slots 136 in respective right and left housing element handle portions 112 and 114, and terminates in knobs 146, whose positions in slots 136 govern the direction of motion of an arthroscopic arcuate tunneling needle 148 having a suture engagement groove 149, which is fully described hereinbelow with reference to FIGS. 15A and 15B.

The multiple action driving assembly 106 also preferably includes a bone engagement element positioning assembly 150, including a finger-engageable release trigger 152, finger engageable bone engagement element advancement knobs 154, a hollow bone engagement element driving shaft 156 and a rotatable bone engagement element 158, pivotably mounted onto a transverse pin 160 (FIG. 17A) mounted onto a forward end 162 (FIG. 22C) of driving shaft 156 for pivotable displacement about an axis 164 (FIG. 17A) defined by pin 160. Hollow bone engagement element driving shaft 156 and rotatable bone engagement element 158 are shown in their respective fully retracted orientations in FIGS. 1A, 1B and 12.

Disposed forwardly of housing elements 102 and 104 is a needle and suture mounting assembly 170 including a suture 172, which removably engages, at a forward end 174 thereof, a groove 176 in rotatable bone engagement element 158 and is mounted, at a rearward end thereof, via a resilient suture mounting element 182 and a suture mounting adaptor 183 onto a groove 184 in a mounting base 185, which is fixedly mounted onto housing portions 102 and 104.

A finger-engageable suture mounting adaptor release lever 186 is mounted onto housing portions 102 and 104 via a pin 187 and is operative when depressed to cause suture mounting adaptor 183 to disengage from groove 184 and thus from engagement with mounting base 185.

First and second visible mechanical indictors 190 and 192 are preferably arranged on the top of respective housing portions 102 and 104. Indicator 190 preferably provides a visible indication of the extent that arcuate tunneling needle 148 is displaced from its fully retracted position shown in FIGS. 1A & 1B. Indicator 192 preferably provides a visible indication of the extent that hollow bone engagement element driving shaft 156 and rotatable bone engagement element 158 are displaced forwardly with respect to their fully retracted positions shown in FIGS. 1A & 1B.

Reference is now made to FIGS. 2A & 2B, which are simplified pictorial illustrations of the arthroscopic surgical device of FIGS. 1A-1B and 12, showing opposite views in a second operative orientation. It is seen that in the second operative orientation, which preferably takes place following insertion of the device through an arthroscopic incision, as described hereinbelow in detail with reference to FIG. 22B, the hollow bone engagement element driving shaft 156 and the rotatable bone engagement element 158 are extended relative to their fully retracted positions shown in FIGS. 1A & 1B, as indicated by indicator 192.

Reference is now made to FIGS. 3A & 3B, which are simplified pictorial illustrations of the arthroscopic surgical device of FIGS. 1A-2B and 12 in a third operative orientation. It is seen that hollow bone engagement element driving shaft 156 and the rotatable bone engagement element 158 are further extended, as indicated by indicator 192, and that rotatable bone engagement element 158 is partially rotated relative to its position shown in FIGS. 2A & 2B. This rotation of the rotatable bone engagement element 158 is initially produced by forward linear displacement of bone-engaging pin driving assembly 120, preferably including knurled knob 122 and elongate bone-engaging pin 124, through hollow bone engagement element driving shaft 156, such that forward end 126 engages rotatable bone engagement element 158 and causes it to pivot about axis 164.

Reference is now made to FIGS. 4A & 4B, which are simplified pictorial illustrations of the arthroscopic surgical device of FIGS. 1A-3B and 12 in a fourth operative orientation. It is seen that the rotatable bone engagement element 158 is now further extended and fully rotated by approximately 90 degrees relative to its position shown in FIGS. 2A & 2B. It is seen that bone engagement pin 124 is further extended by the further forward linear displacement of knob 122 relative to housing portions 102 and 104. This rotation of the rotatable bone engagement element 158 is produced by further forward linear displacement of bone-engaging pin driving assembly 120 and by the tension applied by resilient suture mounting element 182 to suture 172, which engages rotatable bone engagement element 158.

Reference is now made to FIGS. 5A & 5B, which are simplified pictorial illustrations of the arthroscopic surgical device of FIGS. 1A-4B and 12 in a fifth operative orientation. It is seen that the hollow bone engagement element driving shaft 156 and the rotatable bone engagement element 158 are both yet further extended. It is also seen that bone engagement pin 124 is further extended to its maximum extent as indicated by the position of knob 122 relative to housing portions 102 and 104.

Reference is now made to FIGS. 6A & 6B, which are simplified pictorial illustrations of the arthroscopic surgical device of FIGS. 1A-5B and 12 in a sixth operative orientation. It is seen that the rotatable bone engagement element 158 and the bone engagement pin 124 remain in their maximum extended positions, as shown in FIGS. 5A & 5B, and that arcuate tunneling needle 148 is partially extended, as indicated by indicator 190.

Reference is now made to FIGS. 7A & 7B, which are simplified pictorial illustrations of the arthroscopic surgical device of FIGS. 1A-6B and 12 in a seventh operative orientation. It is seen that the rotatable bone engagement element 158 and the bone engagement pin 124 remain in their maximum extended positions, as shown in FIGS. 5A & 5B, and that arcuate tunneling needle 148 is nearly fully extended, as indicated by indicator 190.

Reference is now made to FIGS. 8A & 8B, which are simplified pictorial illustrations of the arthroscopic surgical device of FIGS. 1A-7B and 12 in an eighth operative orientation. It is seen that the rotatable bone engagement element 158 and the bone engagement pin 124 remain in their maximum extended positions, as shown in FIGS. 5A & 5B, and that arcuate tunneling needle 148 is fully extended, as indicated by indicator 190. It is seen that the forward end 174 of suture 172 is now engaged in suture engagement groove 149 of needle 148.

Reference is now made to FIGS. 9A & 9B, which are simplified pictorial illustrations of the arthroscopic surgical device of FIGS. 1A-8B and 12 in a ninth operative orientation. It is seen that the positions of knobs 146 in slots 136 are shifted downwardly, in order to provide retraction of needle 148 in response to ratchet operation. The rotatable bone engagement element 158 and the bone engagement pin 124 remain in their maximum extended positions, as shown in FIGS. 5A & 5B, and arcuate tunneling needle 148 is partially retracted, as indicated by indicator 190, in engagement with the forward end of suture 172, thus drawing the suture 172 backwards along with retraction of the needle 148 along an arcuate path earlier defined through the bone by the arcuate tunneling operation of needle 148.

Reference is now made to FIGS. 10A & 10B, which are simplified pictorial illustrations of the arthroscopic surgical device of FIGS. 1A-9B and 12 in a tenth operative orientation. The rotatable bone engagement element 158 and the bone engagement pin 124 remain in their maximum extended positions, as shown in FIGS. 5A & 5B, and arcuate tunneling needle 148 is fully retracted as indicated by indicator 190, in engagement with the forward end of suture 172, thus drawing the suture backwards along an arcuate path along with full retraction of the needle 148.

Reference is now made to FIGS. 11A & 11B, which are simplified pictorial illustrations of the arthroscopic surgical device of FIGS. 1A-10B and 12 in an eleventh operative orientation. The rotatable bone engagement element 158 and the bone engagement pin 124 have been fully retracted and arcuate tunneling needle 148 is now partially extended in order to permit manual disengagement of the forward end 174 of suture 172 from groove 149 of needle 148. It is noted that the positions of knobs 146 in slots 136 are shifted upwardly, in order to provide extension of needle 148 in response to ratchet operation. The orientations of the various elements are shown by indicators 190 and 192.

Figure 13A:
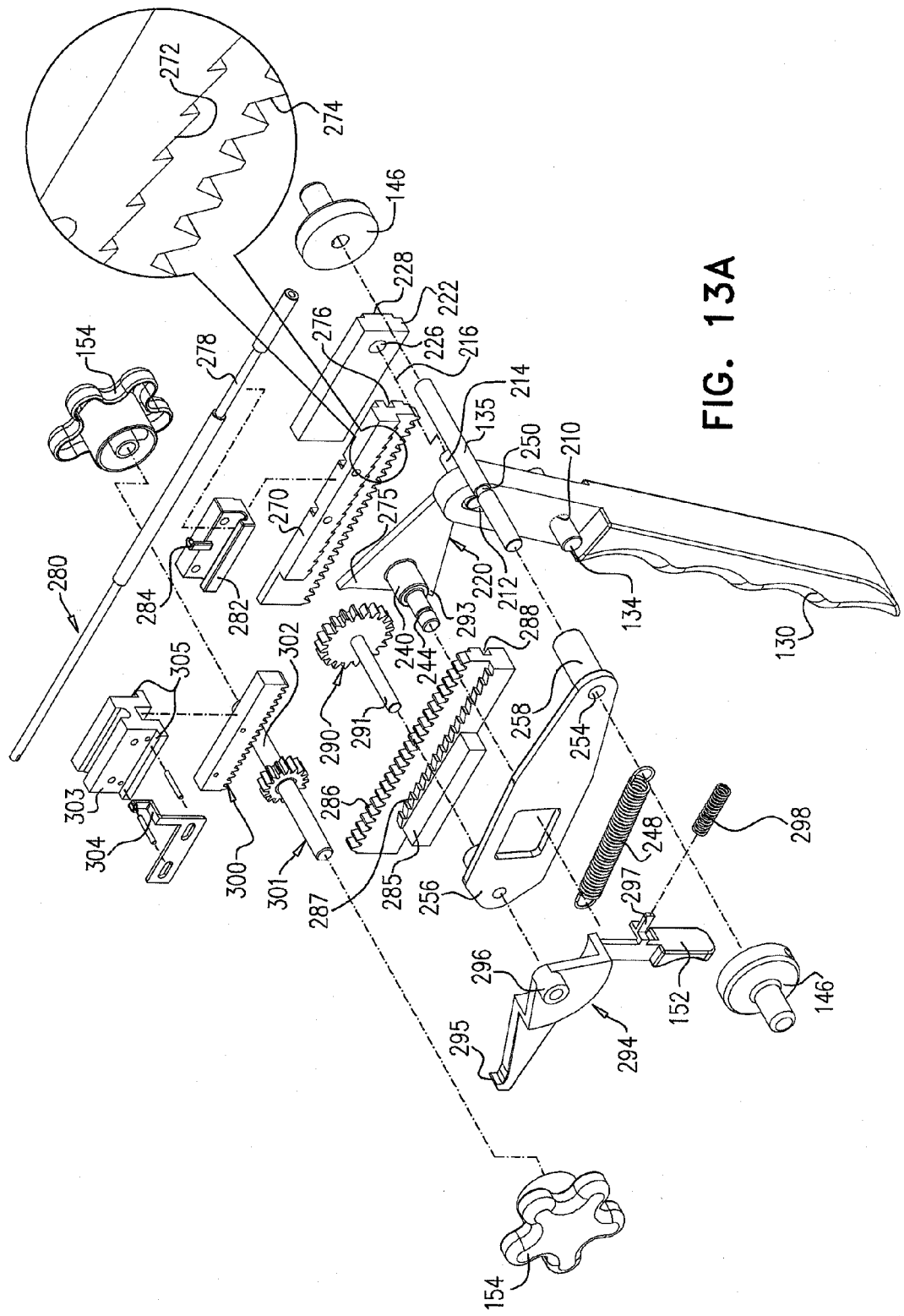
Figure 13C:
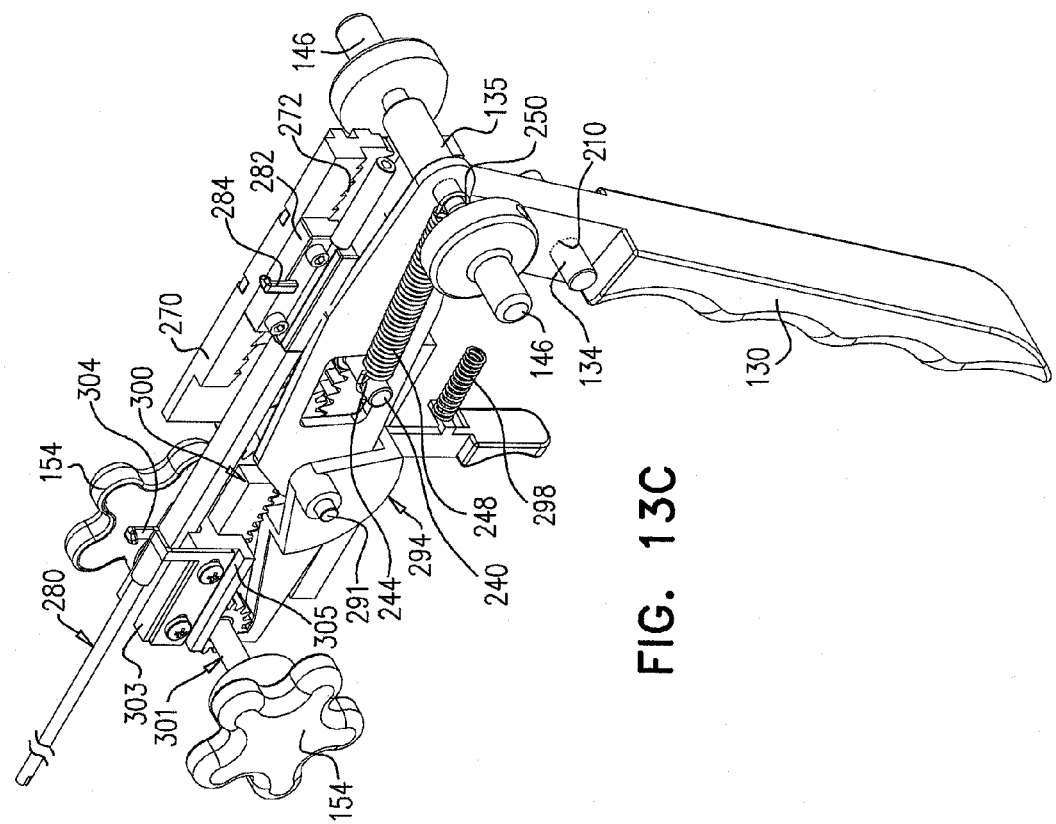
FIG. 13C is a simplified partially assembled view of the portion of the arthroscopic surgical device of FIGS. 13A and 13B.

Reference is now further made to FIG. 12 and additionally made to FIGS. 13A and 13B, which are simplified exploded view illustrations of a portion of the arthroscopic surgical device of FIGS. 1A-12, showing opposite views, and to FIG. 13C, which is a simplified partially assembled view, all of which show details of some elements of multiple action driving assembly 106.

It is seen that ratchet handle 130 is typically formed with a lower aperture 210 which accommodates shaft 134 and is formed with a slot 212. A pin 214 is slidably movable in slot 212, such that reciprocal arcuate motion of slot 212 is translated into reciprocal planar forward and rearward motion perpendicular to a longitudinal axis 216 of pin 214. First and second reciprocal motion connection elements 220 and 222 are fixed to pin 214 at respective apertures 224 and 226 and move together therewith in reciprocal forward and rearward linear motion in response to rotational motion of ratchet handle 130.

Connection element 222 includes an elongate protrusion 228, which moves reciprocally in a slot 230 formed in housing portion 102.

Connection element 220 includes a side extending shaft 240 which includes a circumferential groove 244 onto which is mounted one end of a tension spring 248. An opposite end of tension spring 248 is mounted in a circumferential groove 250 formed in shaft 135. Shaft 135 extends through an aperture 254 formed in a toggle element 256, which communicates with a hollow shaft portion 258 of toggle element 256. Shaft 135 extends through slots 136 formed on respective housing portions 102 and 104.

A double rack linear toothed element 270 is provided with an upper linear toothed ratchet rack 272 and a lower linear toothed gear rack 274. A pointed corner 275 of connection element 220 selectably engages upper linear toothed rack 272. Double rack linear toothed element 270 is preferably formed with a slot 276 which engages an elongate axial protrusion 277 formed in housing element 102.

An inward recessed portion 278 adjacent an inner end of a generally rigid flexible needle driving strip driving shaft 280 is fixedly mounted onto double rack linear toothed element 270 by means of a mounting element 282 which is typically bolted onto element 270. An indicator finger 284 is formed on mounting element 282 and forms part of indicator 190.

A second double rack linear toothed element 285 is provided with an upper linear toothed gear rack 286 and a lower linear toothed ratchet rack 287. Double rack linear toothed element 285 is preferably formed with a slot 288 which engages an elongate axial protrusion 289 formed in housing element 102.

A gear 290, having a gear shaft 291, engages lower linear toothed gear rack 274 of element 270 and also simultaneously engages upper linear toothed gear rack 286 of element 285. Gear shaft 291 preferably is mounted at its opposite ends in apertures 292 in respective housing elements 102 and 104.

A pointed corner 293 of connection element 220 selectably engages lower linear toothed ratchet rack 287 of element 285.

It is seen that trigger 152 forms part of a selectable release element 294, which forms part of assembly 150 and includes a engagement protrusion 295 and collar 296 through which extends gear shaft 291. Selectable release element 294 is pivotable about the axis of gear shaft 291 and includes a protrusion 297 which serves as a seat for one end of a compression spring 298, whose other end is seated in a spring seat 299 formed in housing portion 102.

A linear gear rack element 300 is preferably driven along an linear travel path by a gear 301, having a gear shaft 302, which extends through respective housing portions 102 and 104 into fixed engagement with knobs 154. Gear 301 is normally prevented from clockwise rotation by engagement therewith by engagement protrusion 295 of selectable release element 294. A mounting assembly 303 is fixed to linear gear rack element 300 and is operative to fixedly mount a rearward end of hollow bone engagement element driving shaft 156 onto element 300 for linear movement therewith. An indicator finger 304 is also preferably fixedly mounted onto mounting assembly 303 and forms part of indicator 192.

Preferably, mounting assembly 303 is formed with a pair of oppositely directed elongate protrusions 305 which engage corresponding grooves 306 formed in housing portions 102 and 104.

Reference is now made to FIGS. 14A-16B, which illustrate needle and suture mounting assembly 170. The needle and suture mounting assembly 170 includes linear gear rack element 300, which is preferably driven along an elongate travel path by gear 301 responsive to rotation of either of knobs 154.

Suture mounting adaptor 183 is seated on mounting base 185, a rearward end of which is, in turn, fixed to a forward end of the housing. Mounting base 185 surrounds a rearward end of an extension shaft 310 formed of two identical side by side pieces 311 which together define two mutually spaced axial mounting bores extending therethrough, which bores are designated by reference numerals 312 and 314. Bore 312 slidably accommodates hollow bone engagement element driving shaft 156 and has a generally round cross-section.

Bore 314 slidably accommodates parts of a flexible arcuate needle driving assembly, which preferably includes a flexible needle driving strip 318, preferably formed of spring steel, and generally rigid flexible needle driving strip driving shaft 280, which is mounted at the rear of flexible needle driving strip 318, preferably as shown in enlargement A in FIG. 14B. As seen in enlargement B in FIG. 14B, bore 314 has a generally circular cross sectional portion 322 to accommodate shaft 280 from which extend a pair of symmetrical side cut outs 324 to accommodate the side edges of strip 318.

Forward of extension shaft 310, there is preferably formed an arcuate needle storage and guiding portion 350, which is formed with an arcuate bore 352 including a rectangular portion 354, which slidably accommodates needle 148, from which extend a pair of symmetrical side cut outs 356 to accommodate the side edges of strip 318.

As seen particularly in FIG. 15A, it is seen that suture engagement groove 149 of arcuate needle 148 is partially defined by a partially overlying portion 357 of needle 148.

It is seen that bone engagement pin 124 slidably extends through bone engagement element driving shaft 156, which in turn slidably extends through bore 312.

Figure 17A:
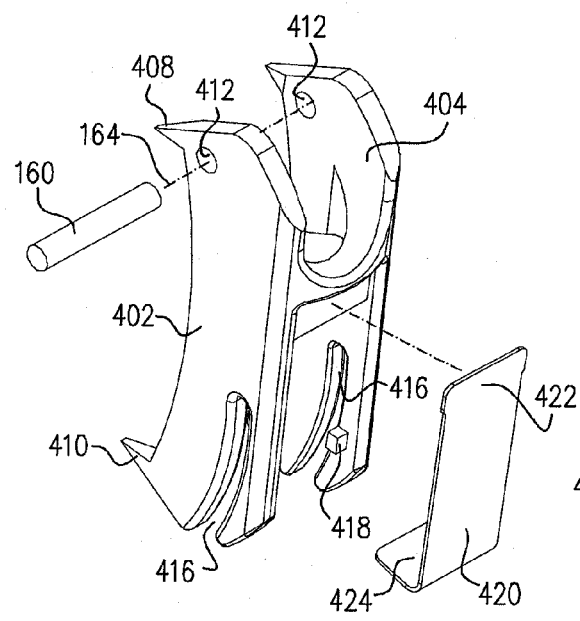
FIGS. 17A and 17B are respective exploded and assembled views of part of the portion of the arthroscopic surgical device of FIGS. 14A & 14B.
Figure 17B:
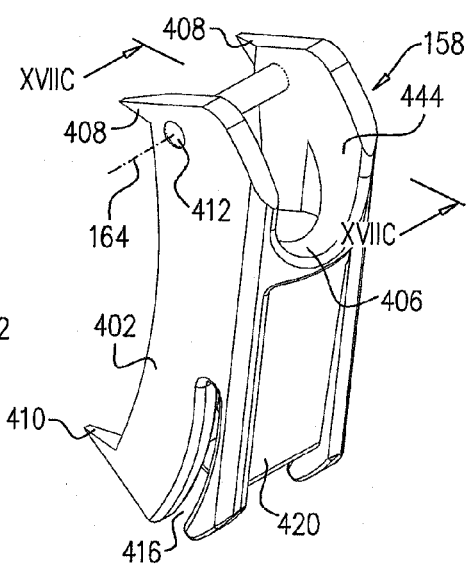
Figure 17C:
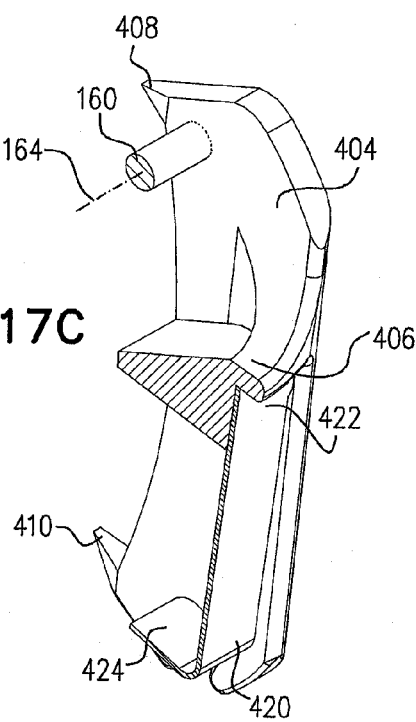
FIG. 17C is a sectional illustration of the part of the portion of the arthroscopic surgical device of FIGS. 17A & 17B, taken along line XVIIC-XVIIC in FIG. 17B.

Reference is now made to FIGS. 17A and 17B, which are respective exploded and assembled views of the rotatable bone engagement element 158, which forms part of the portion of the arthroscopic surgical device of FIGS. 14A & 14B, and to FIG. 17C, which is a sectional illustration of the rotatable bone engagement element 158, taken along line XVIIC-XVIIC in FIG. 17B.

As seen in FIGS. 17A-17C, the rotatable bone engagement element 158 is a side-to-side symmetric element including side wall portions 402 and 404 joined by a bridging portion 406. Each of the side wall portions 402 and 404 includes a protruding top pointed bone engaging portion 408, a protruding bottom pointed bone engaging portion 410 and an aperture 412 for rotatably accommodating pin 160. An arcuate slot 416 is formed in each side wall. Slots 416 together define groove 176 (FIGS. 1A & 1B) which is partially engaged by the forward end 174 of suture 172. An inwardly directed protrusion 418 is formed on an inner wall surface of each of side wall portions 402 and 404.

A flexible bent plate 420 is preferably attached at a top portion 422 to a rear facing surface of bridging portion 406 and is arranged to have a forwardly directed bottom portion 424 normally seated between side wall portions 402 and 404 so as to partially block access to arcuate slots 416 by the forward end 174 of suture 172.

Figure 18A:
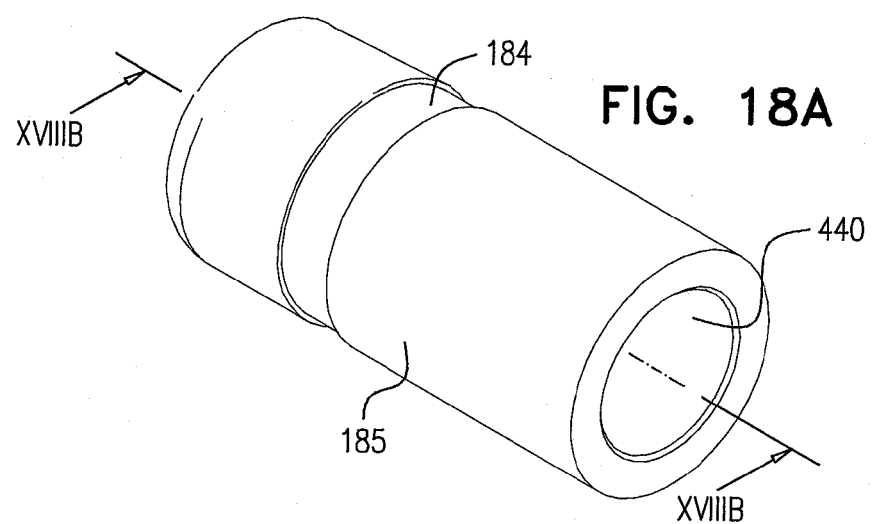
FIG. 18A is a pictorial illustration of another part of the portion of the arthroscopic surgical device of FIGS. 14A & 14B.
Figure 18B:
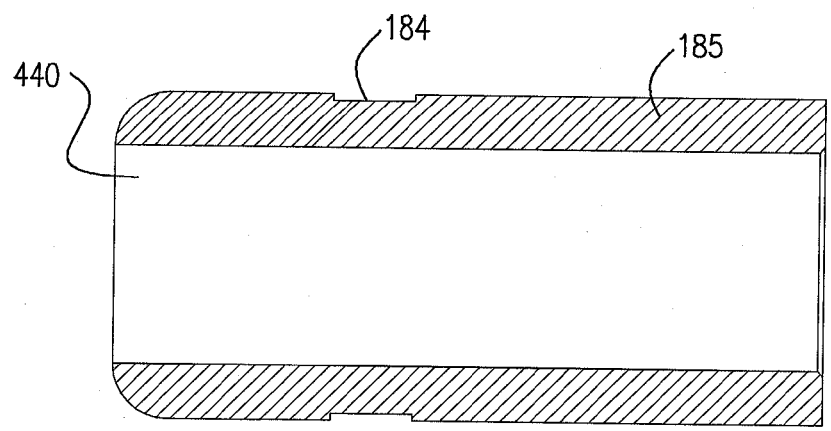
FIG. 18B is a sectional illustration of the part of the portion of the arthroscopic surgical device shown in FIG. 18A, taken along line XVIIIB-XVIIIB in FIG. 18A.

Reference is now made to FIG. 18A, which is a pictorial illustration of mounting base 185, another part of the portion of the arthroscopic surgical device of FIGS. 14A & 14B, and to FIG. 18B, which is a sectional illustration taken along line XVIIIB-XVIIIB in FIG. 18A. As seen in FIGS. 18A & 18B, the mounting base 185 is a generally cylindrical element having a longitudinal bore 440 extending therethrough, which accommodates the rearward end of extension shaft 310.

Figure 19A:
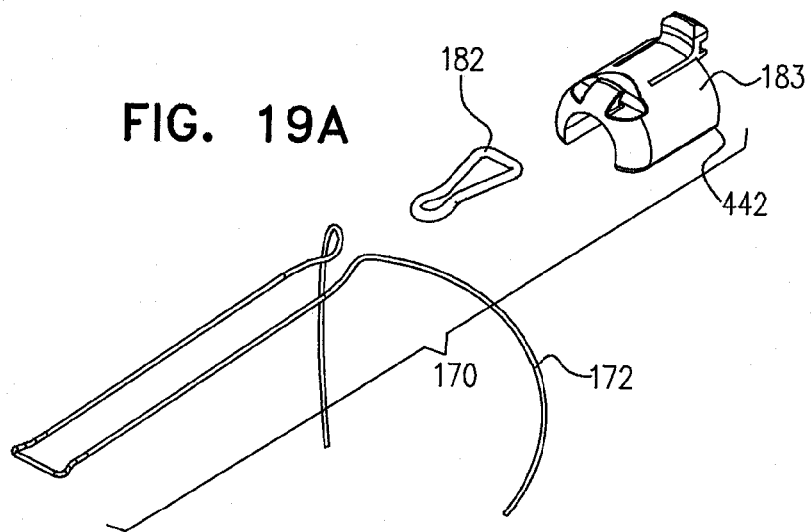
FIGS. 19A, 19B and 19C are simplified illustrations of one alternative functionality for mounting of a suture on a resilient loop which is in turn mounted on a forward portion of the arthroscopic surgical device of FIGS. 1A-12.
Figure 19B:
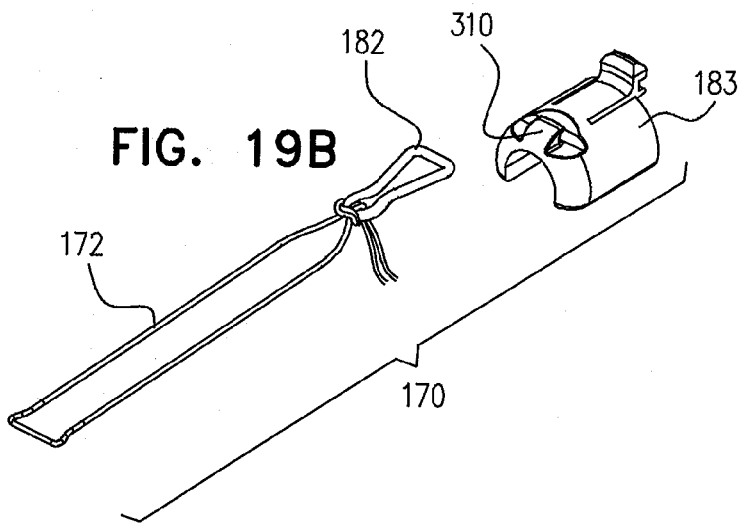
Figure 19C:
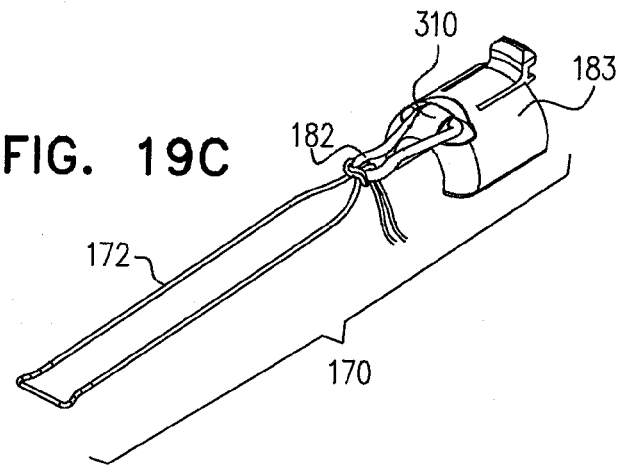

Reference is now made to FIGS. 19A, 19B and 19C, which are simplified illustrations of one alternative structure and functionality for mounting of a suture on a resilient loop which is in turn mounted on a forward portion of the arthroscopic surgical device of FIGS. 1A-12.

As seen in FIGS. 19A-19C, there is preferably provided a suture mounting assembly including suture 172, resilient suture mounting element 182 and suture mounting adapter 183, which is adapted for removable mounting onto mounting base 185 (FIGS. 18A-18B). Suture mounting element adapter 183 preferably is configured generally as a cap which is removably seated onto mounting base 185. Suture mounting element adapter 183 preferably includes a rearward facing resilient engagement element 442 which is snap engageable with circumferential groove 184 of mounting base 185.

FIG. 19A shows the various elements prior to assembly thereof and FIG. 19B shows the suture 172 knotted onto the resilient suture mounting element 182. FIG. 19C shows the resilient suture mount element 182, having the suture 172 knotted thereon, retained onto hook 310 of suture mounting element adapter 183.

Figure 20A:
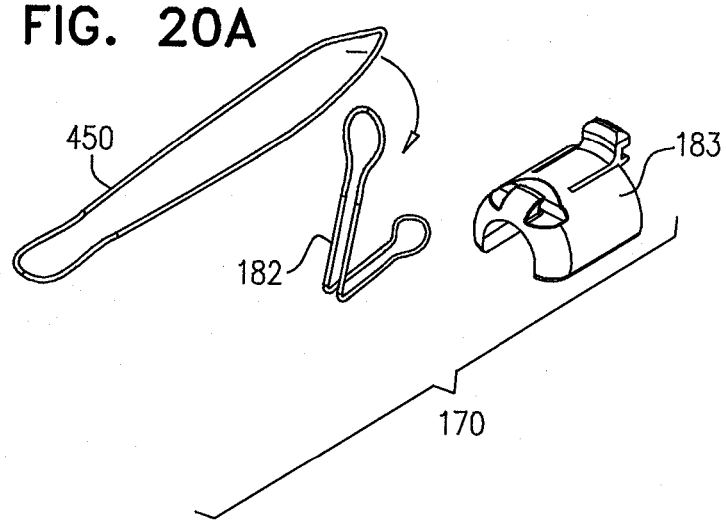
FIGS. 20A, 20B and 20C are simplified illustrations of another alternative functionality for mounting of a suture on a resilient loop which is in turn mounted on a forward portion of the arthroscopic surgical device of FIGS. 1A-12.
Figure 20B:
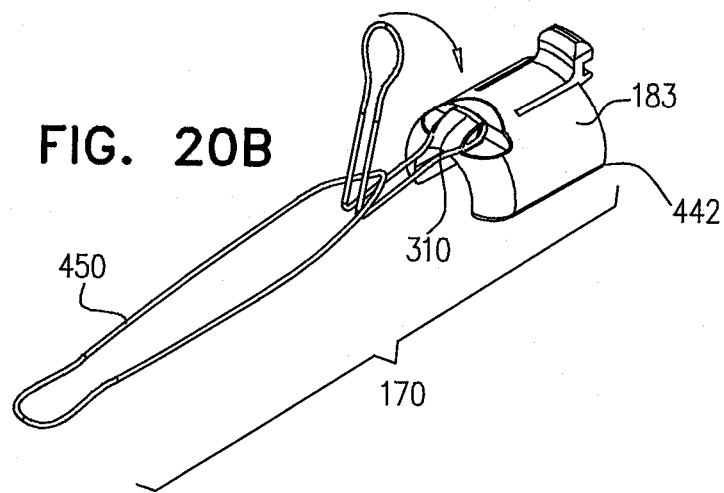
Figure 20C:
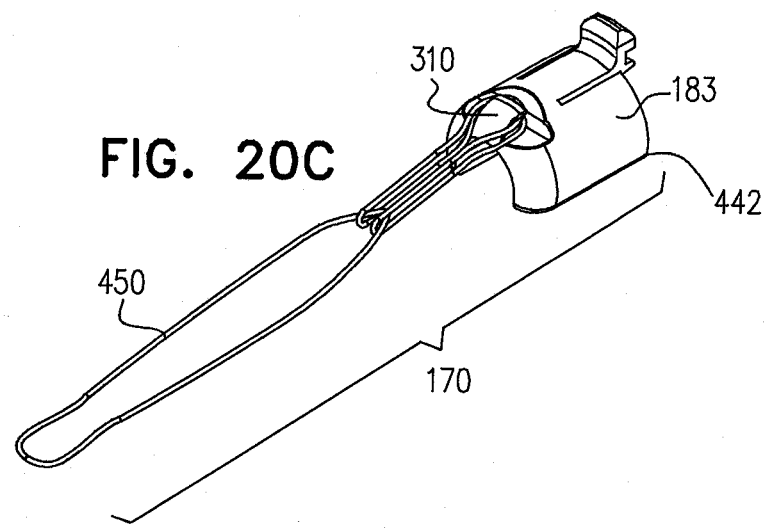

Reference is now made to FIGS. 20A, 20B and 20C, which are simplified illustrations of another alternative structure and functionality for mounting of a suture on a resilient loop which is in turn mounted on a forward portion of the arthroscopic surgical device of FIGS. 1A-12.

As seen in FIGS. 20A-20C, there is preferably provided a suture mounting assembly including a endless looped suture 450, resilient suture mounting element 182 and suture mounting adapter 183, which is adapted for removable mounting onto mounting base 185 (FIGS. 18A-18B). As in the embodiment of FIGS. 19A-19C, suture mounting element adapter 183 preferably is configured generally as a cap which is removably seated onto mounting base 185 and preferably includes a rearward facing resilient engagement element 442 which is snap engageable with circumferential groove 184 of mounting base 185.

FIG. 20A shows the various elements prior to assembly thereof and FIG. 20B shows the suture 450 looped over the resilient suture mounting element 182. FIG. 20C shows the resilient suture mount element 182, having the suture 450 knotted thereon, retained onto hook 310 of suture mounting element adapter 183.

Reference is now made to FIGS. 21A, 21B, 21C, 21D, 21E, 21F, 21G, 21H, 21I, 21J, 21K, 21L, 21M and 21N, which illustrate details of the operation of the arthroscopic surgical device of FIGS. 1A-20C, and to FIGS. 22A, 22B, 22C, 22D, 22E, 22F, 22G, 22H, 22I, 22J, 22K, 22L, 22M and 22N, which are simplified illustrations of operation of the arthroscopic surgical device of FIGS. 1A-21N in a clinical context.

As seen in FIGS. 21A and 22A, which correspond generally to FIGS. 1A & 1B, prior to insertion of the arthroscopic surgical device 100 through an arthroscopic incision 500 in a patient, a suture mounting assembly 170, such as that described hereinabove with reference to FIGS. 19A-19C, is mounted onto the arthroscopic surgical device 100, with a forward end 174 of the suture 172 being retained in slots 416 (FIGS. 17A-17C) defining groove 176 (FIGS. 1A & 1B) of bone engagement element 158.

Figure 22B:
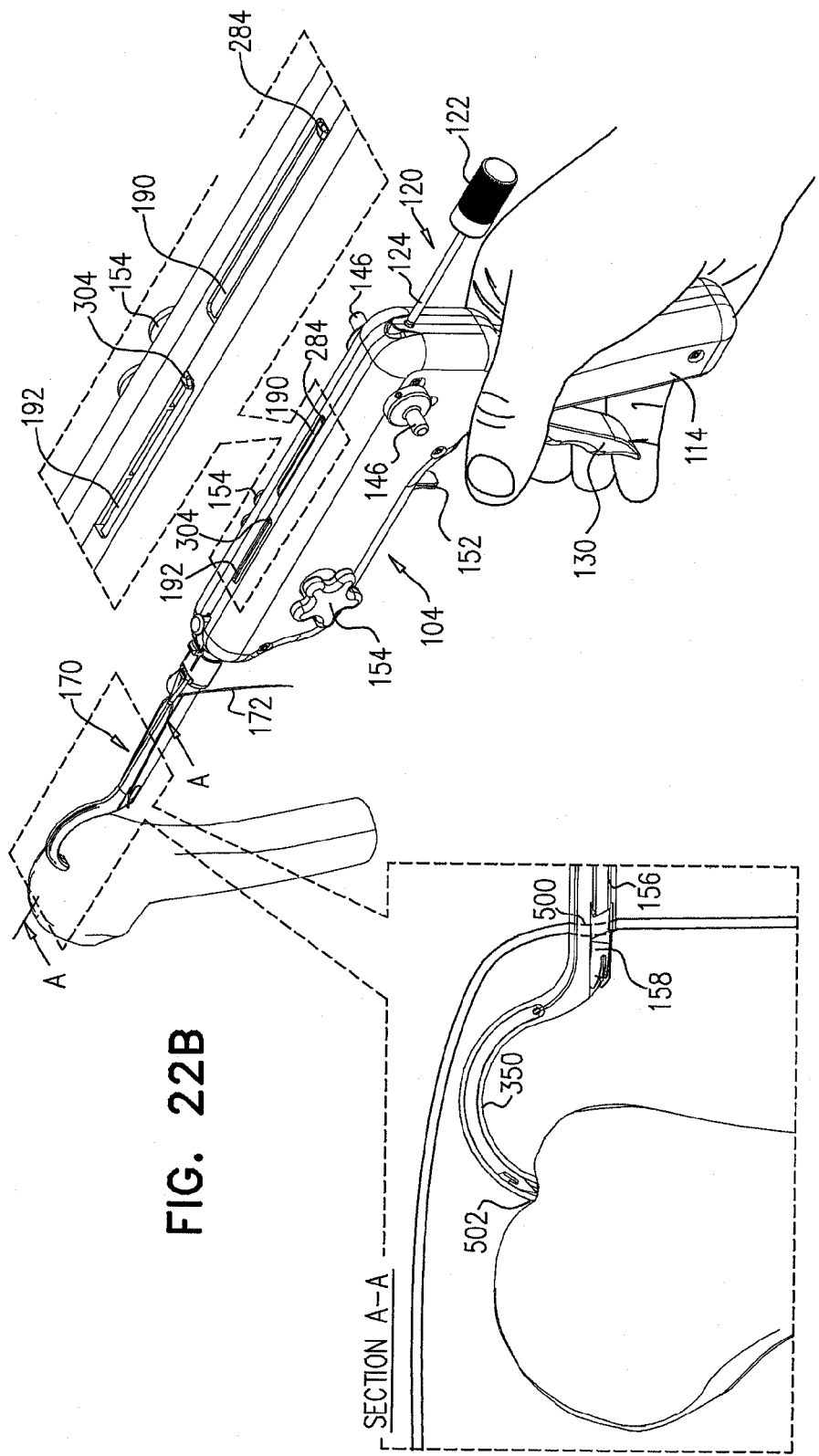

FIG. 22B shows insertion of a forward portion of arcuate needle storage and guiding portion 350 through incision 500 such that a forwardmost end 502 of arcuate needle storage and guiding portion 350 engages a bone, here shown as a humerus.

Figure 21B:
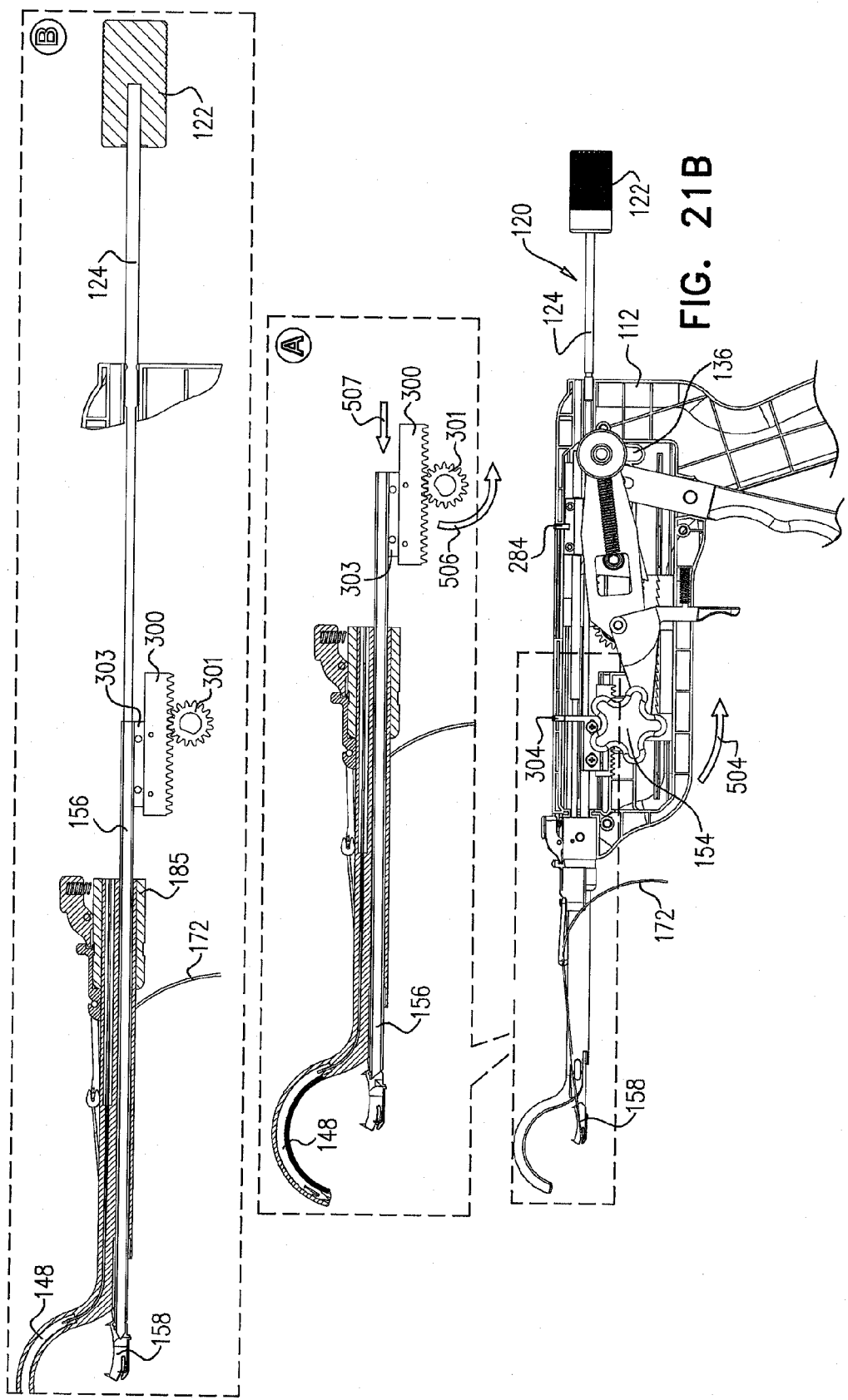
Figure 21D:
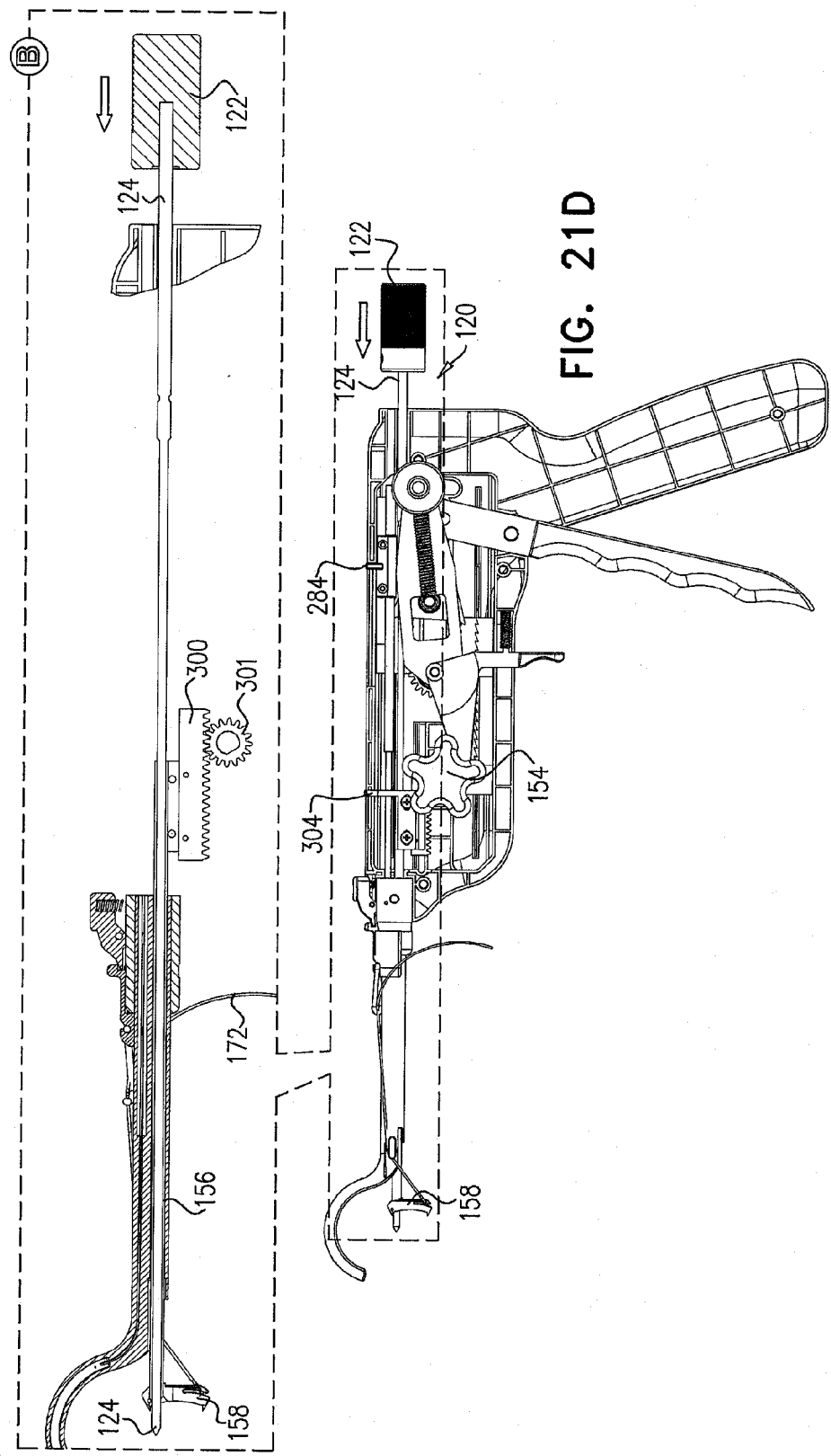
Figure 21E:
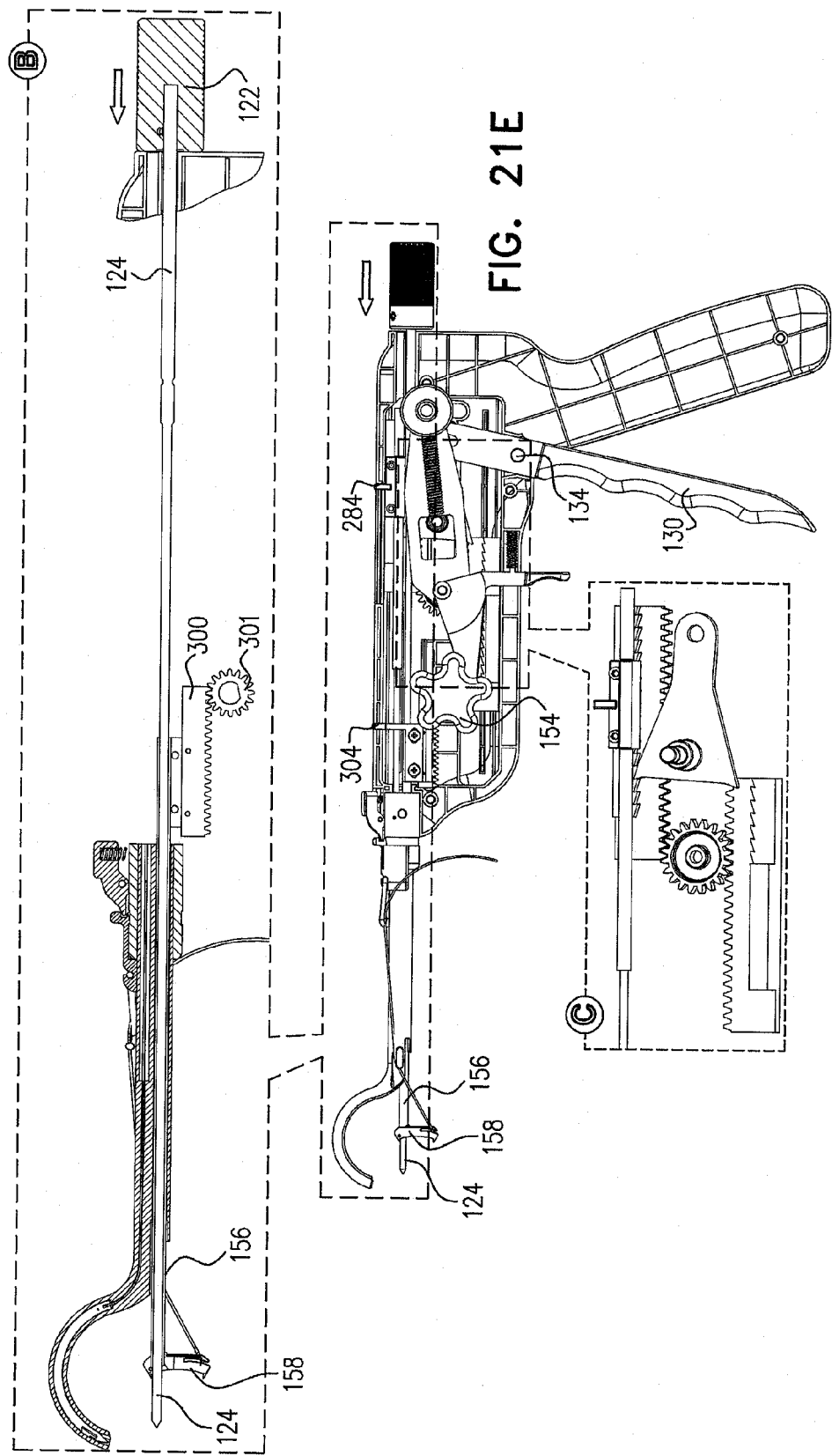

It is seen in FIGS. 21A, 22A & 22B that the bone engagement pin 124 and a hollow bone engagement element driving shaft 156 are in their fully retracted positions and that knobs 146 are in their upward positions in slots 136. As seen in FIG. 22B, indicator 190 shows full retraction of flexible needle driving strip driving shaft 280 and of arcuate tunneling needle 148 and indicator 192 shows full retraction of hollow bone engagement element driving shaft 156 and of bone engagement element 158. As further shown in FIGS. 21A, 21B & 22B, knobs 146 are positioned to their upper operative orientation in slots 136, for forward direction driving of arcuate tunneling needle 148.

Figure 22C:
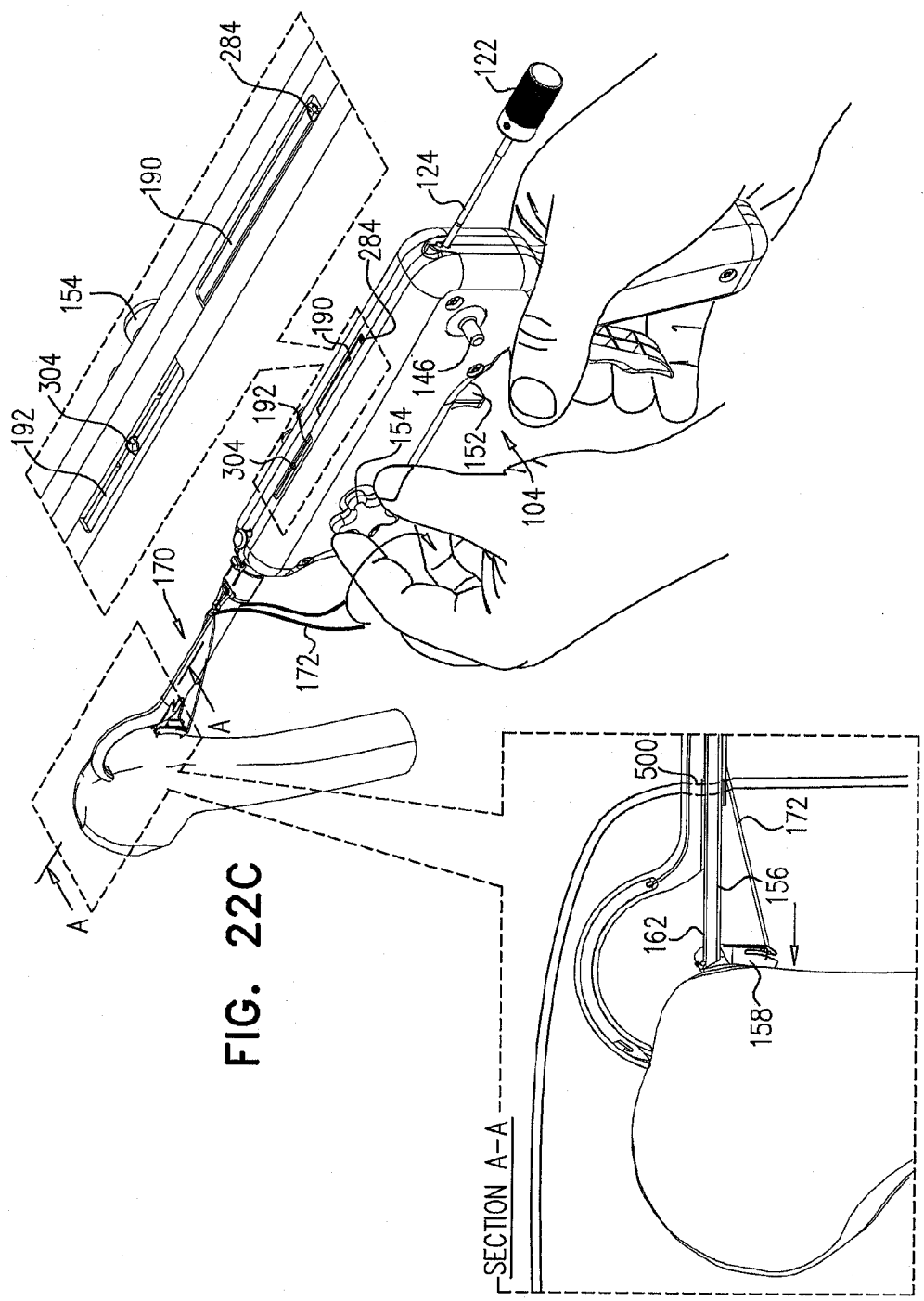

FIGS. 21B and 22C, which correspond generally to FIGS. 2A & 2B, show counterclockwise rotation of knobs 154, in the sense of FIG. 21B, as indicated by an arrow 504 in FIG. 21B. This counterclockwise rotation, as seen particularly in enlargement A in FIG. 21B, produces corresponding counterclockwise rotation of gear 301, as indicated by an arrow 506, in engagement with linear gear rack element 300, driving linear gear rack element 300 forwardly in the sense of FIG. 21B, as indicated by an arrow 507.

As noted above with reference to FIGS. 12-13C, mounting assembly 303 fixes hollow bone engagement element driving shaft 156 onto element 300 for linear movement therewith. Thus, forward motion of linear gear rack element 300 produces corresponding forward extension of hollow bone engagement element driving shaft 156, as can be seen by comparing enlargement A of FIG. 21B with corresponding enlargement A of FIG. 21A.

Enlargements B in FIGS. 21B, 21C, 21D and 21E, which correspond generally to FIGS. 2A-5B, show various stages in rotation of rotatable bone engagement element 158 about axis 164 and forward displacement of knurled knob 122 and elongate bone-engaging pin 124, extending forwardly therefrom.

FIG. 22C, which corresponds generally to FIGS. 4A & 4B, shows extension of hollow bone engagement element driving shaft 156 and rotation of rotatable bone engagement element 158 about axis 164 defined by pin 160 into operative engagement with the bone. Indicator 190 is unchanged from its position shown in FIG. 22B, indicating that the arcuate needle 148 remains in its fully retracted position. Indicator 192 shows the extension of hollow bone engagement element driving shaft 156 as can be seen by comparing the positions of indicator finger 304 in FIGS. 22B and 22C respectively.

Figure 22D:
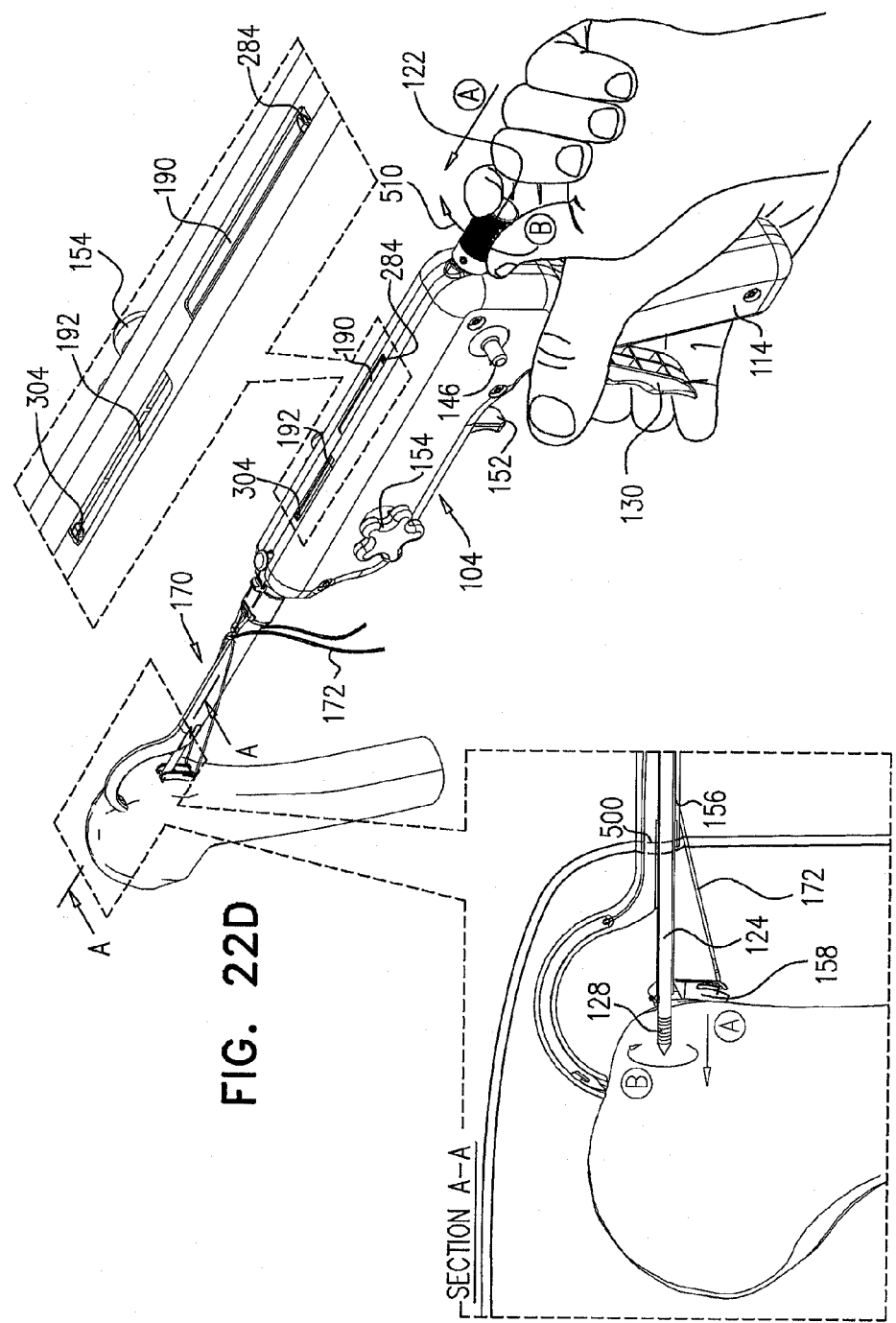

FIG. 22D, which corresponds generally to FIGS. 5A & 5B, shows that the optionally threaded portion 128 at the forward end 126 of bone engagement pin 124 is fully engaged with the bone, preferably as by both linear and rotational movement thereof, as indicated by the position of knob 122 and by an arrow 510 relative to housing portions 102 and 104.

Figure 21F:
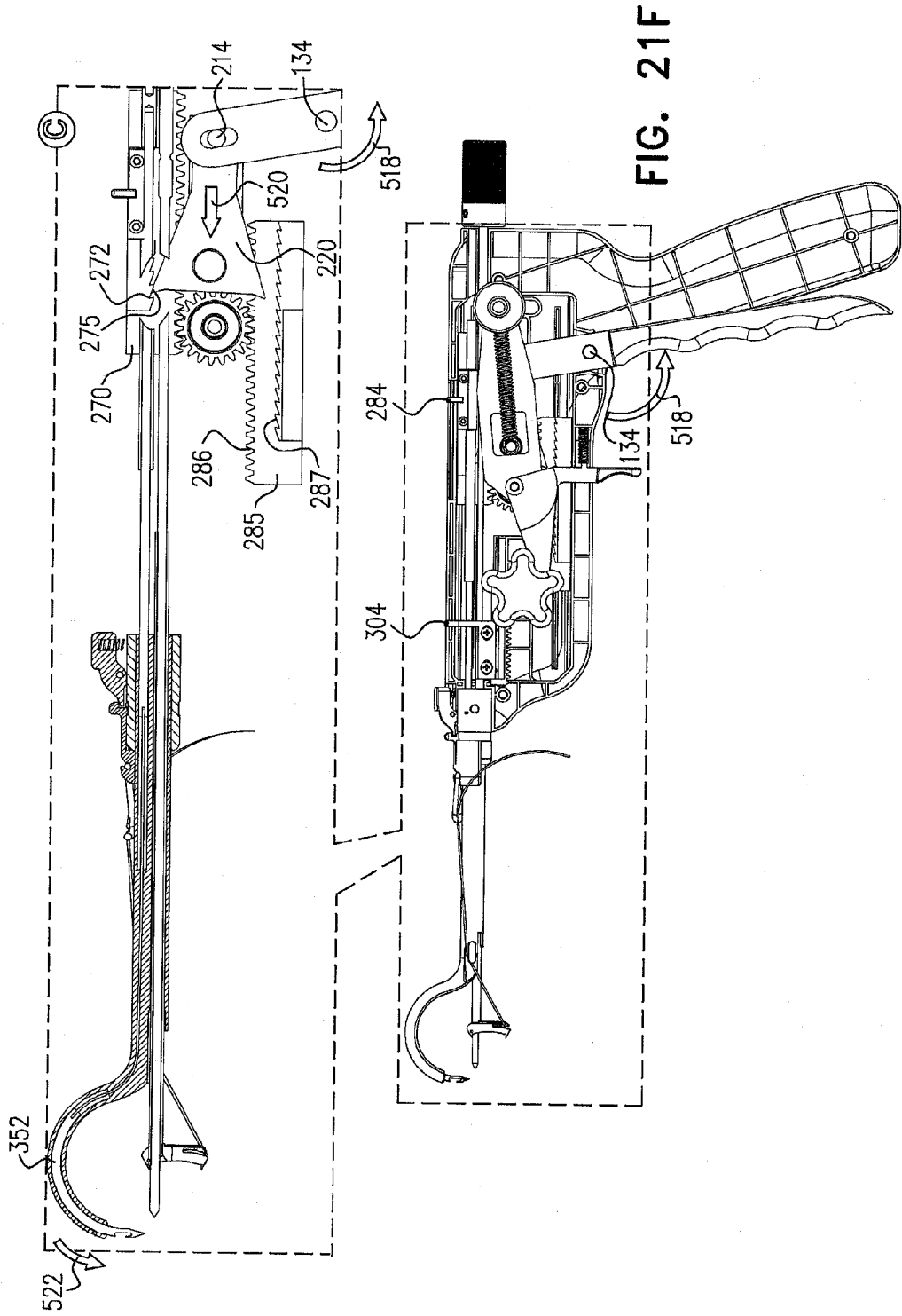
Figure 22E:
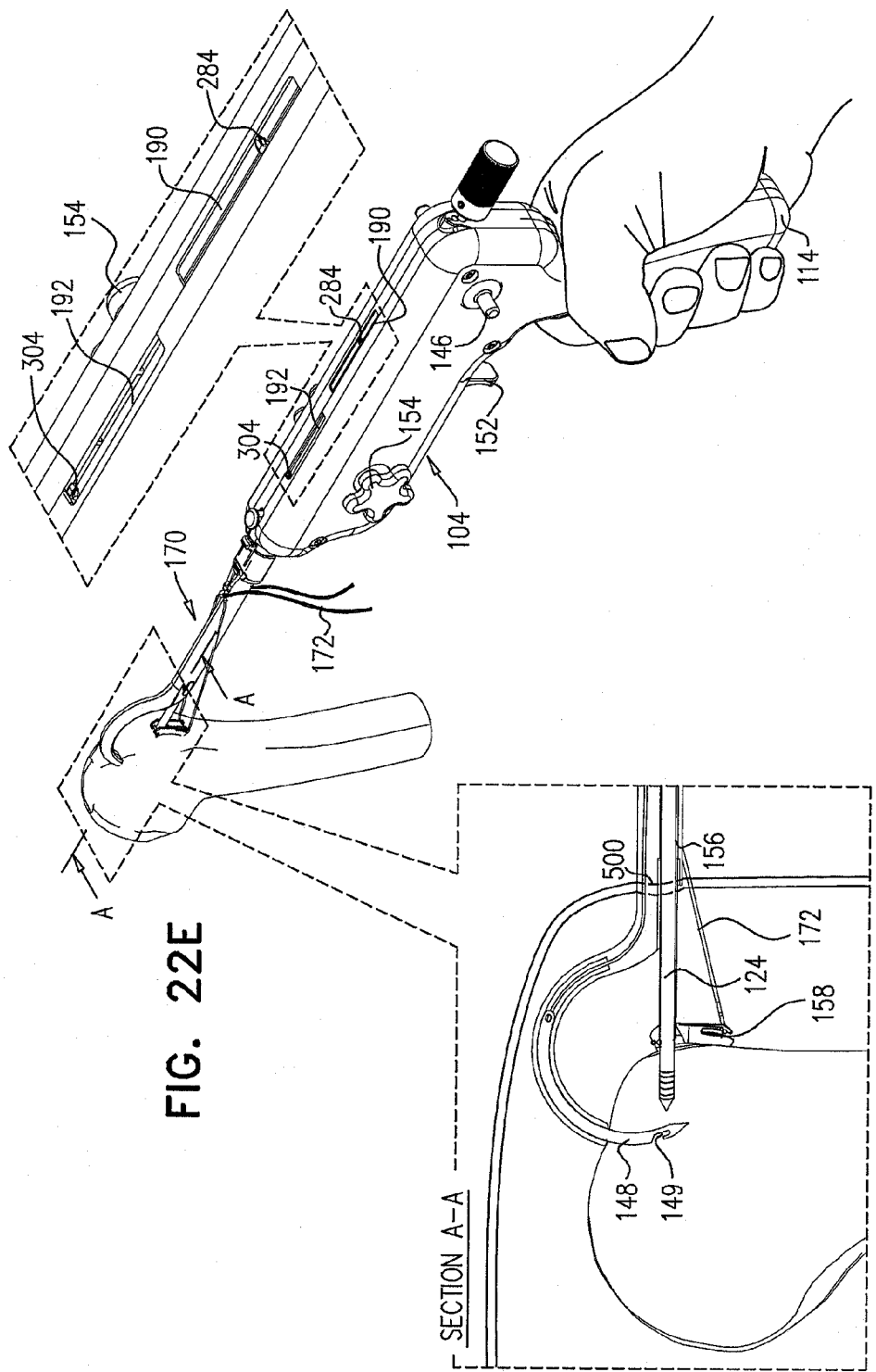

FIGS. 21F and 21G and FIG. 22E, which correspond generally to FIGS. 6A & 6B, show partial extension of arcuate tunneling needle 148 through the bone, as indicated by indicator finger 284 of indicator 190.

FIGS. 21E, 21F, 21G & 21H, particularly at enlargements C thereof, show that squeezing on hand-engageable ratchet handle 130 produces rotation thereof, as indicated by an arrow 518, about a rotational axis defined by shaft 134 and, via pin 214, displaces first reciprocal motion connection element 220 linearly forwardly, as indicated by an arrow 520, with pointed corner 275 of connection element 220 in engagement with upper linear toothed rack 272 of double rack linear toothed element 270, thereby driving element 270 and flexible needle driving strip driving shaft 280 forwardly and causing arcuate needle 148, driven thereby, to travel along an arcuate path through the portion of arcuate bore 352 having a rectangular cross section and to extend outwardly into tunneling engagement with the bone, as indicated by arrow 522.

Figure 21H:
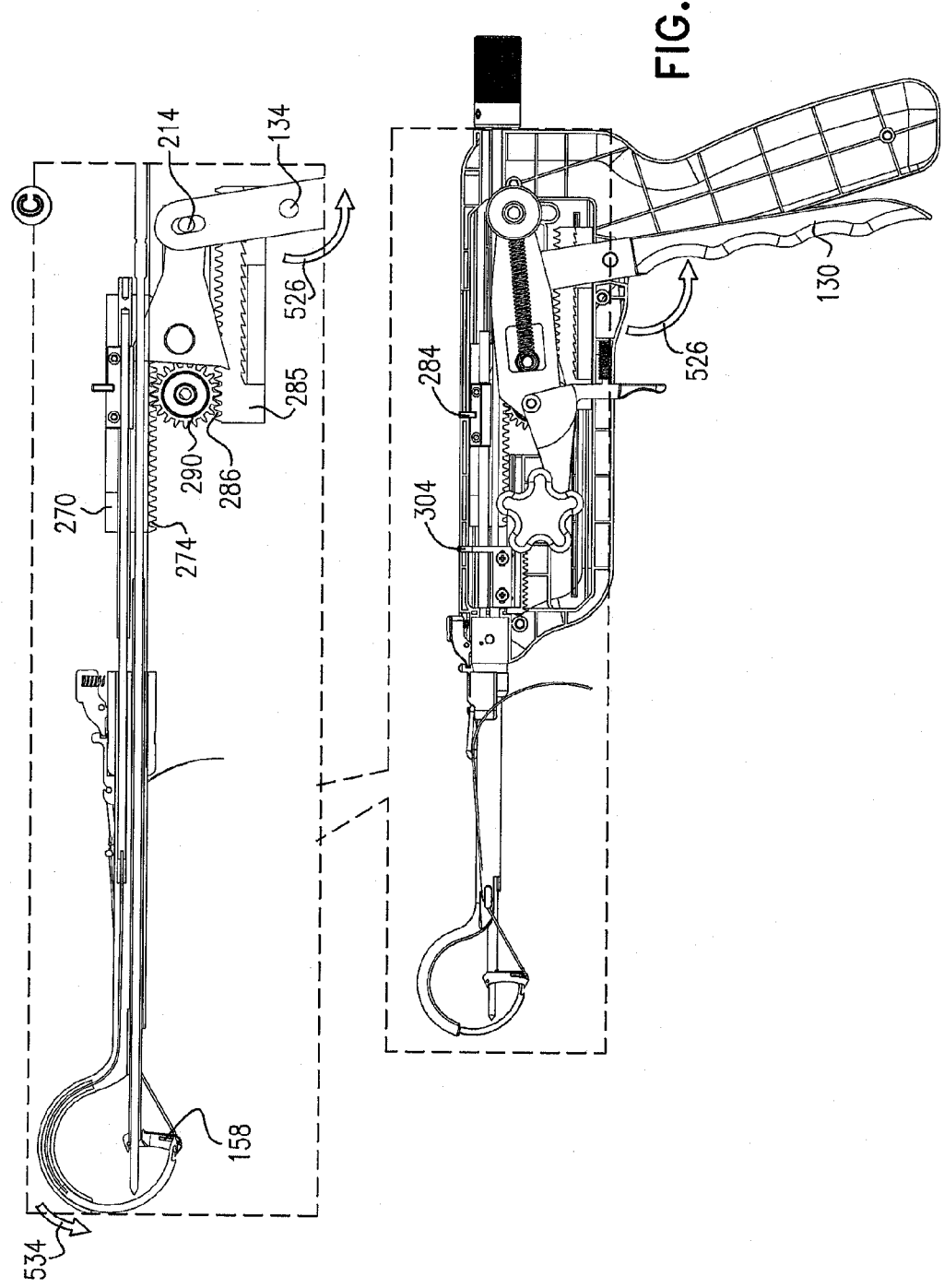

FIG. 21G shows retraction of handle 130, as indicated by an arrow 530, under urging of spring 248 whereby pointed corner 275 is operationally disengaged from rack 272 of double rack linear toothed element 270, such that one or more subsequent squeeze on handle 130, as indicated by an arrow 526, produces further linear forward motion of double rack linear toothed element 270 and consequent further arcuate extension travel of needle 148, as seen in FIG. 21H.

It is appreciated that simultaneous engagement of gear 290 with lower linear toothed gear rack 274 of element 270 and upper linear toothed gear rack 286 of element 285 produces rearward linear motion of element 285 corresponding to forward linear motion of element 270.

Figure 22F:
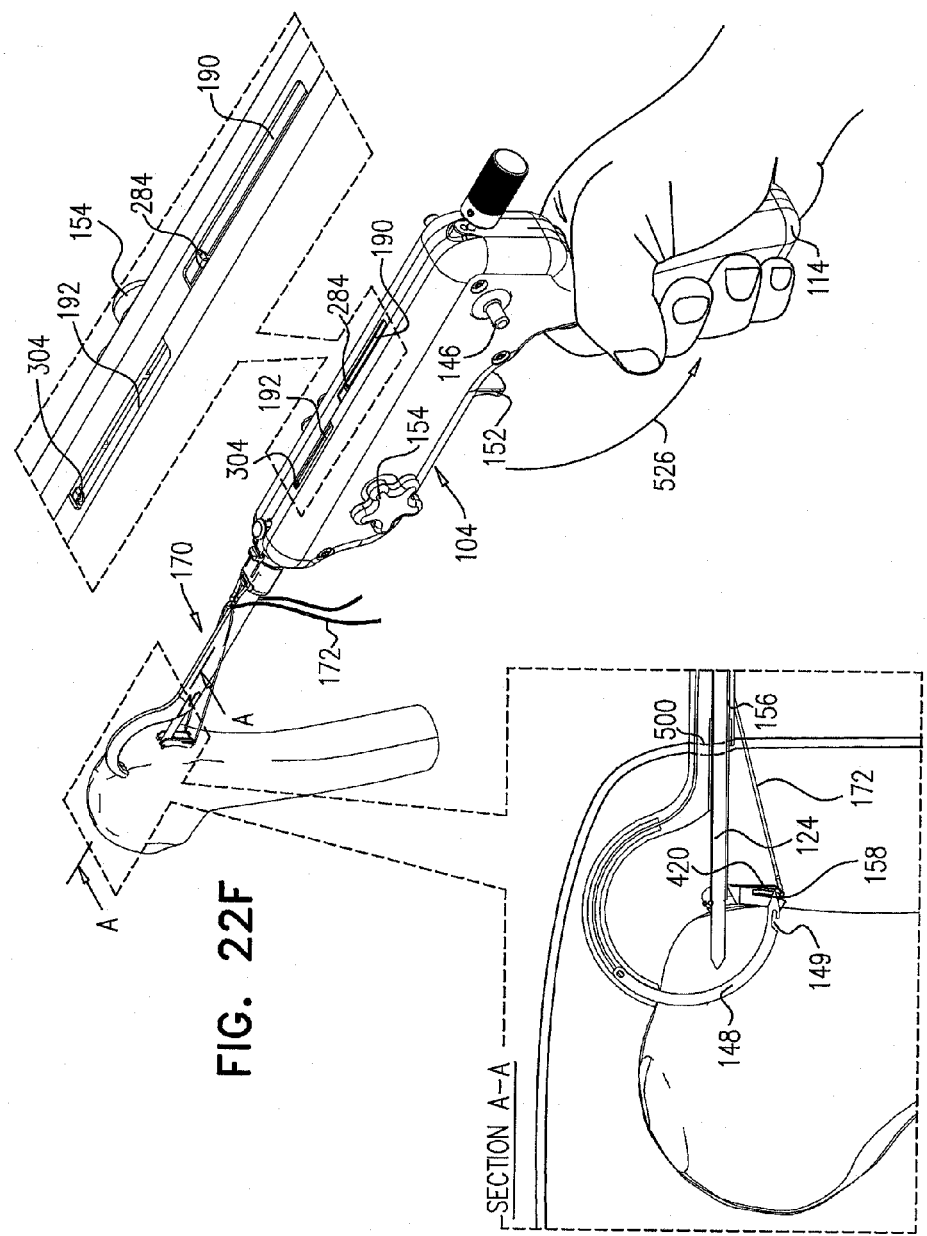

FIGS. 21H and 22F, which correspond generally to FIGS. 7A & 7B, show further arcuate extension of arcuate tunnel needle 148, as indicated by an arrow 534, through the bone, driven by further squeezing of handle 130, as well as initial engagement of a forward end of needle 148 with flexible bent plate 420 of the bone engagement element 158.

Figure 21I:
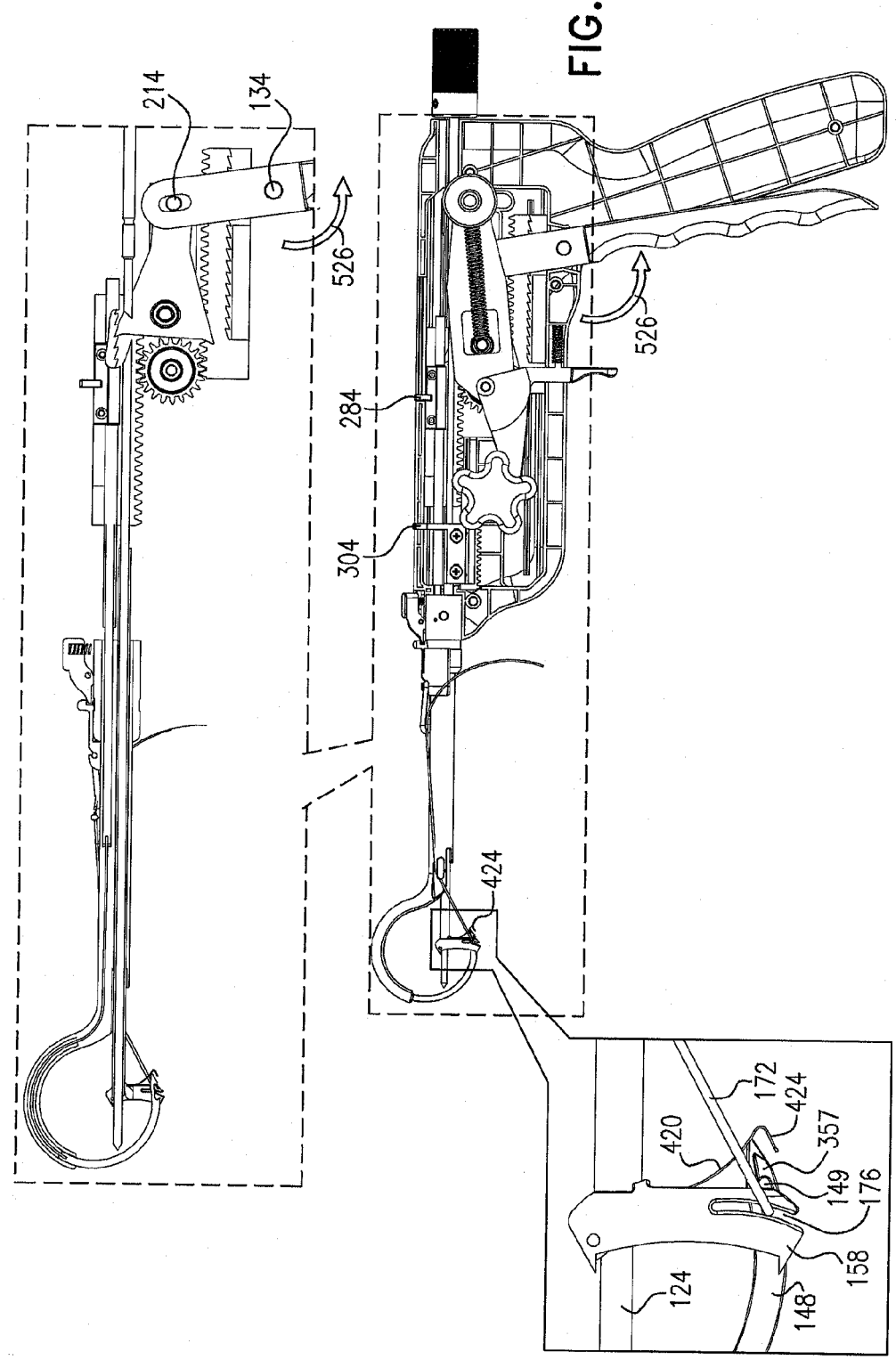

FIGS. 21I & 22G, which correspond generally to FIGS. 8A & 8B, show nearly complete extension of arcuate tunnel needle 148 in engagement with flexible bent plate 420 and bending back of flexible bent plate 420 so as to disengage bottom portion 424 thereof from the forward end 174 of suture 172. It is noted that forward end 174 of suture 172 does not move further into suture engagement groove 149 of needle 148 because it is blocked by a partially overlying portion 357 of needle 148 which partially defines groove 149 of needle 148.

Figure 22H:
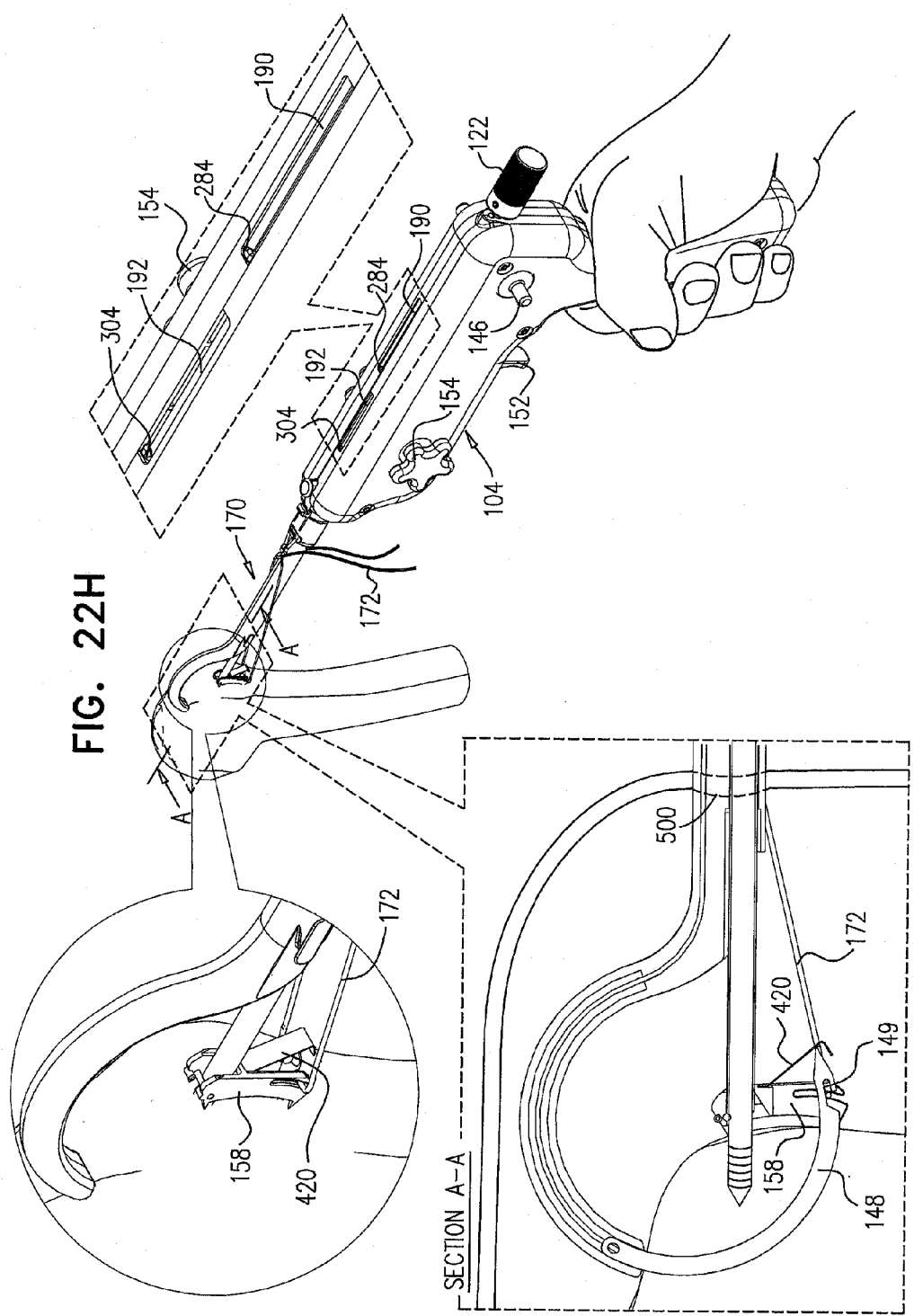

FIG. 22H, which corresponds generally to FIGS. 8A & 8B, shows complete extension of arcuate tunnel needle 148. It is noted that the forward end of suture 172 moves into groove 149 of needle 148, by the resilient action of resilient suture mounting element 182, and is engaged by needle 148. The complete extension of arcuate tunnel needle 148 is indicated by indicator finger 284 of indicator 190.

Figure 21J:
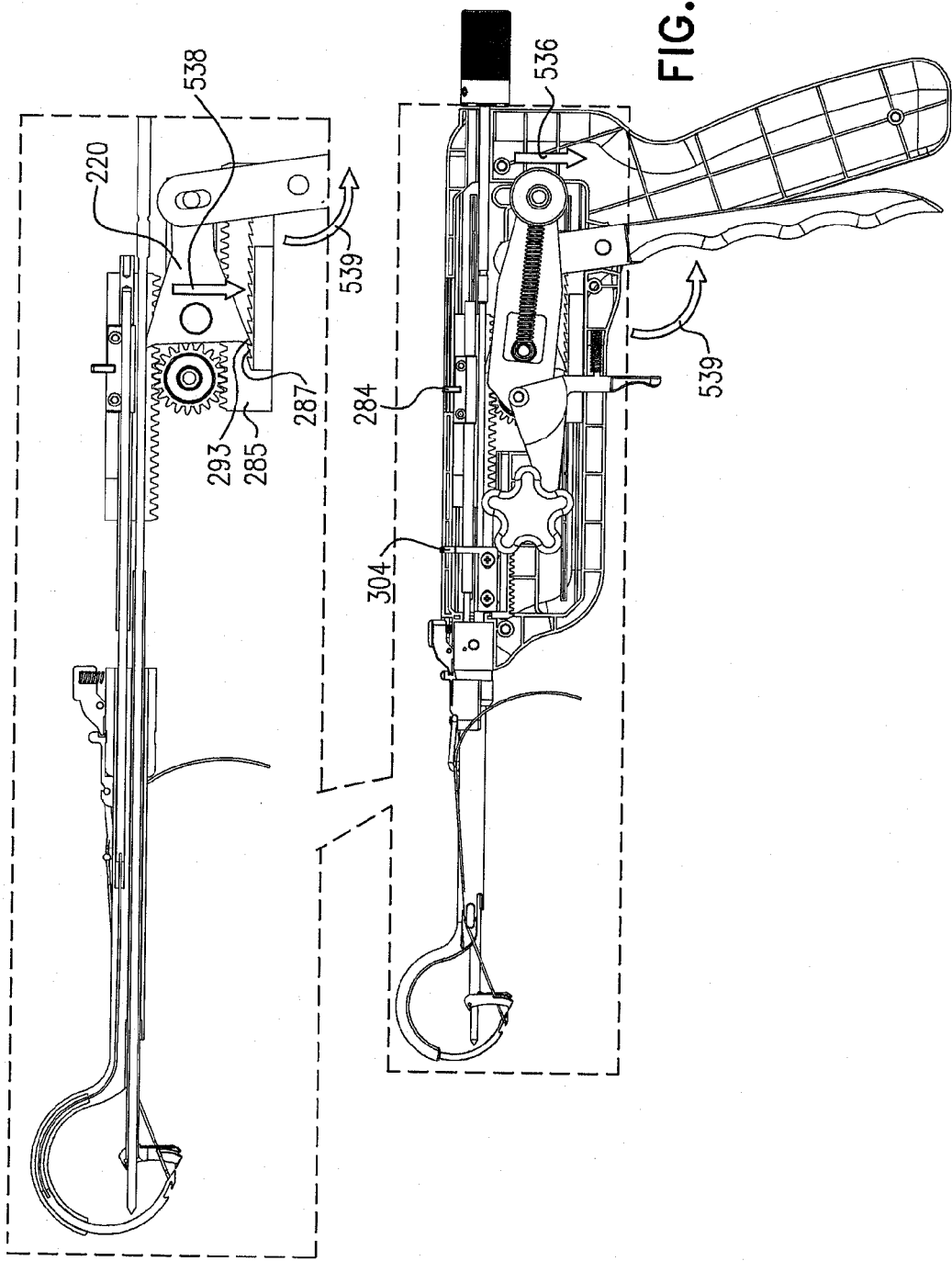

FIGS. 21J, 22I and 22J, which correspond generally to FIGS. 9A & 9B, show initial retraction of arcuate tunnel needle 148, as indicated by arrows 535, following repositioning of knobs 146, as indicated by an arrow 536, which produces reverse driving of the ratchet assembly operated by squeezing handle 130. It is noted that the needle 148 carries with it the suture 172.

Repositioning of knobs 146 causes repositioning of connection element 220, as indicated by an arrow 538, causing pointed corner 293 of connection element 220 to engage lower linear toothed ratchet rack 287 of element 285, as seen in FIG. 21J, such that squeezing of handle 130, as indicated by an arrow 539, causes element 285 to be moved linearly forward. It is appreciated that simultaneous engagement of gear 290 with lower linear toothed gear rack 274 of element 270 and upper linear toothed gear rack 286 of element 285 produces rearward linear motion of element 270 in response to forward linear motion of element 285.

Figure 22K:
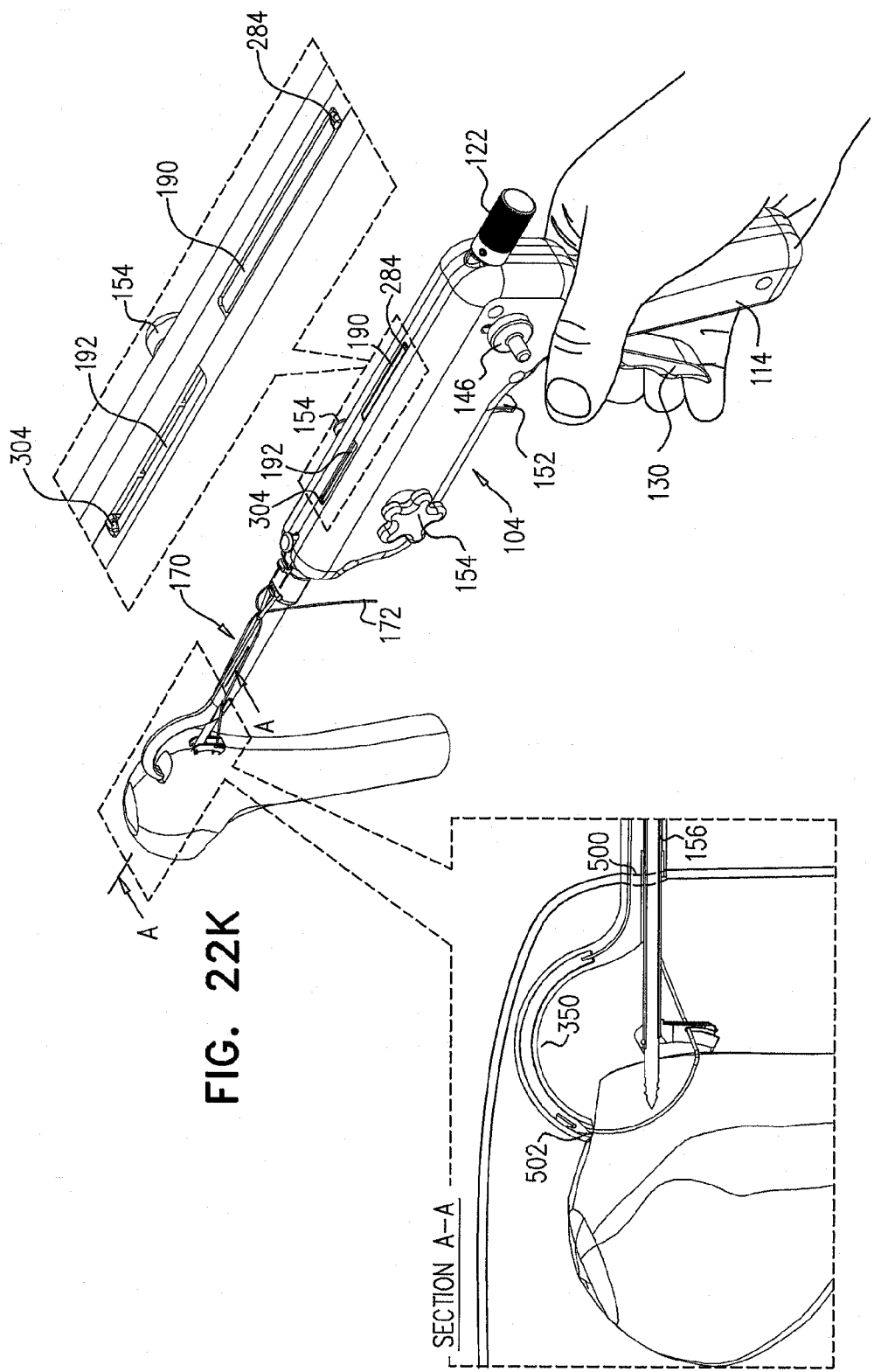

FIG. 22K, which corresponds generally to FIGS. 10A & 10B, shows further retraction of arcuate tunnel needle 148. It is noted that the needle 148 continues to draw the suture 172 with it.

Figure 21K:
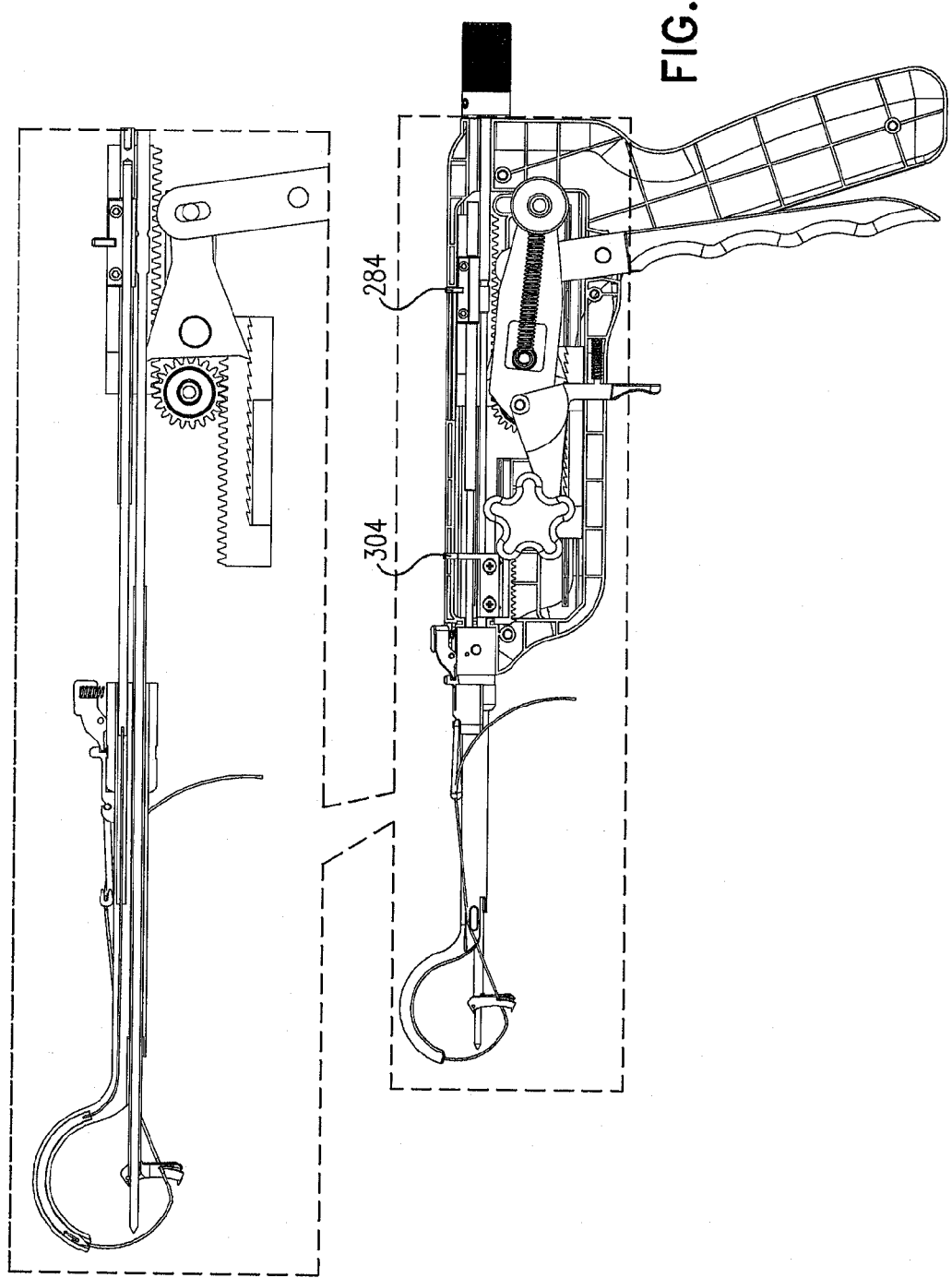
Figure 22L:
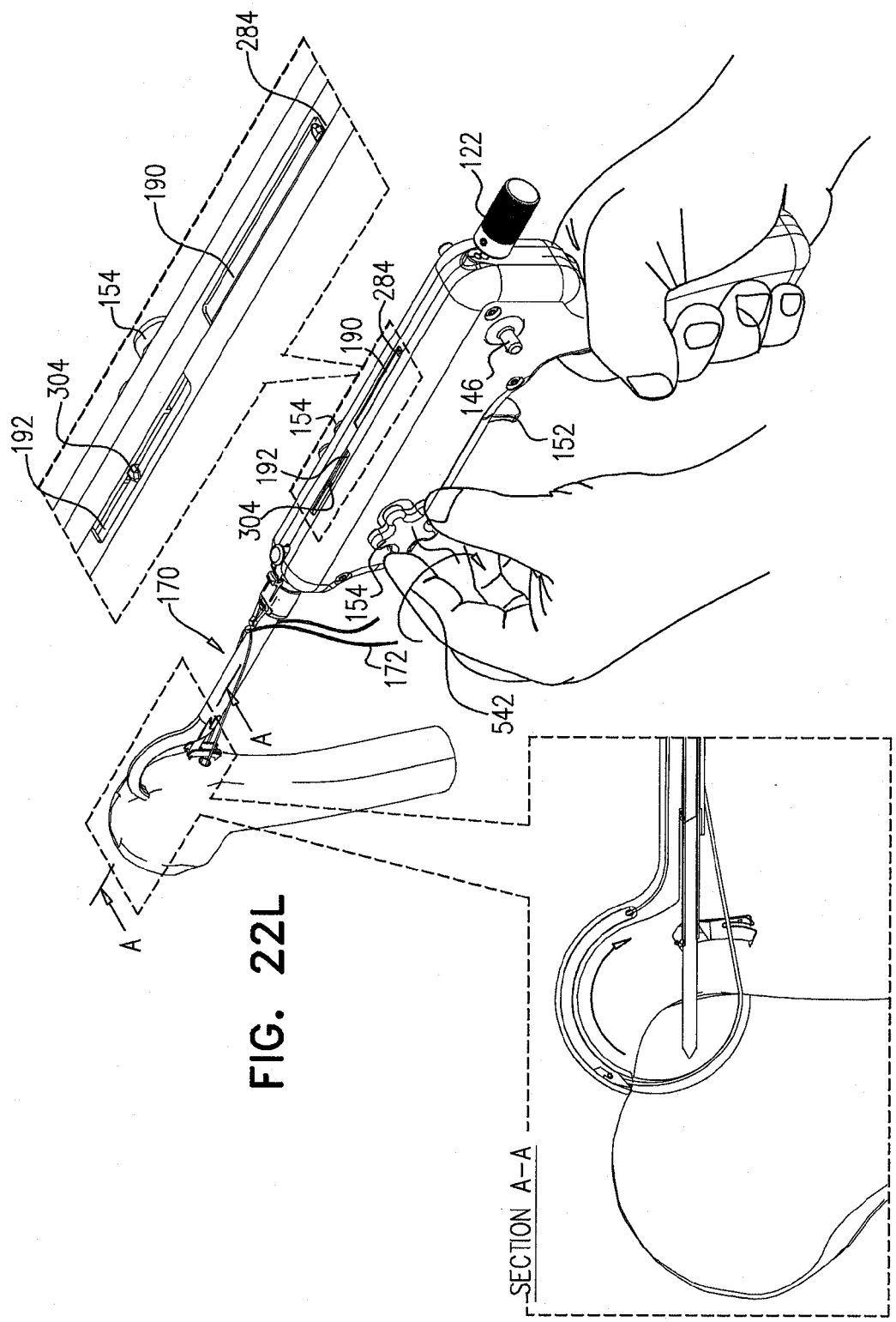

FIGS. 21K and 22L, which correspond generally to FIGS. 11A and 11B, show retraction of arcuate tunnel needle 148 entirely out of the bone. It is noted that the needle 148 continues to draw the suture 172 therewith.

Figure 21L:
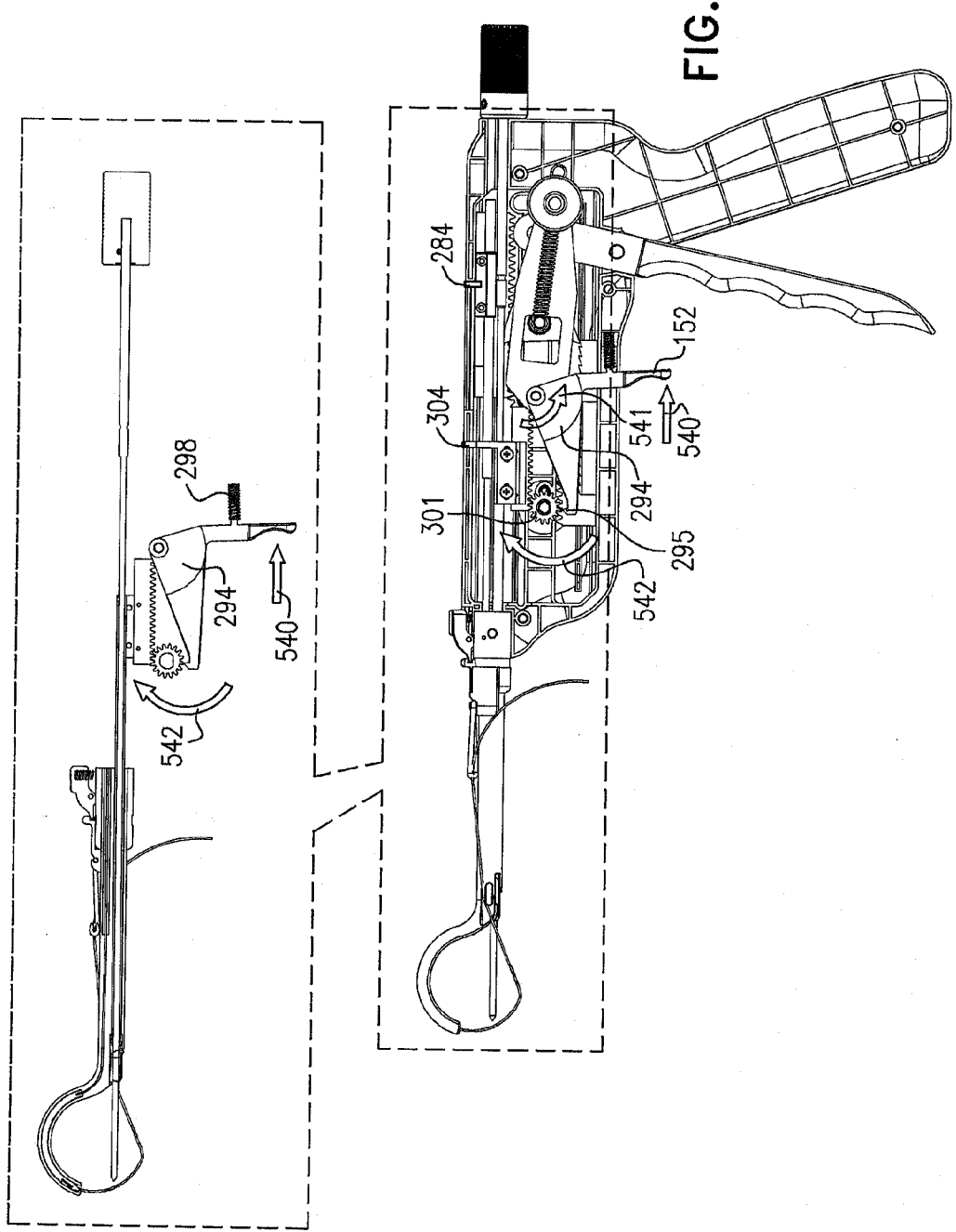

FIG. 21L shows rearward pivot displacement of finger-engageable release trigger 152, as indicated by an arrow 540, against the urging of compression spring 298, and simultaneous clockwise rotation of knob 154. Rearward pivot displacement of release trigger 152 causes selectable release element 294 to rotate counterclockwise, as indicated by arrow 541, about the axis of gear shaft 291, thereby producing disengagement of engagement protrusion 295 of element 294 from gear 301, thus enabling gear 301 to be rotated by knob 154 in a clockwise direction, as indicated by an arrow 542, which in turn produces retraction of hollow bone engagement element driving shaft 156.

Figure 21M:
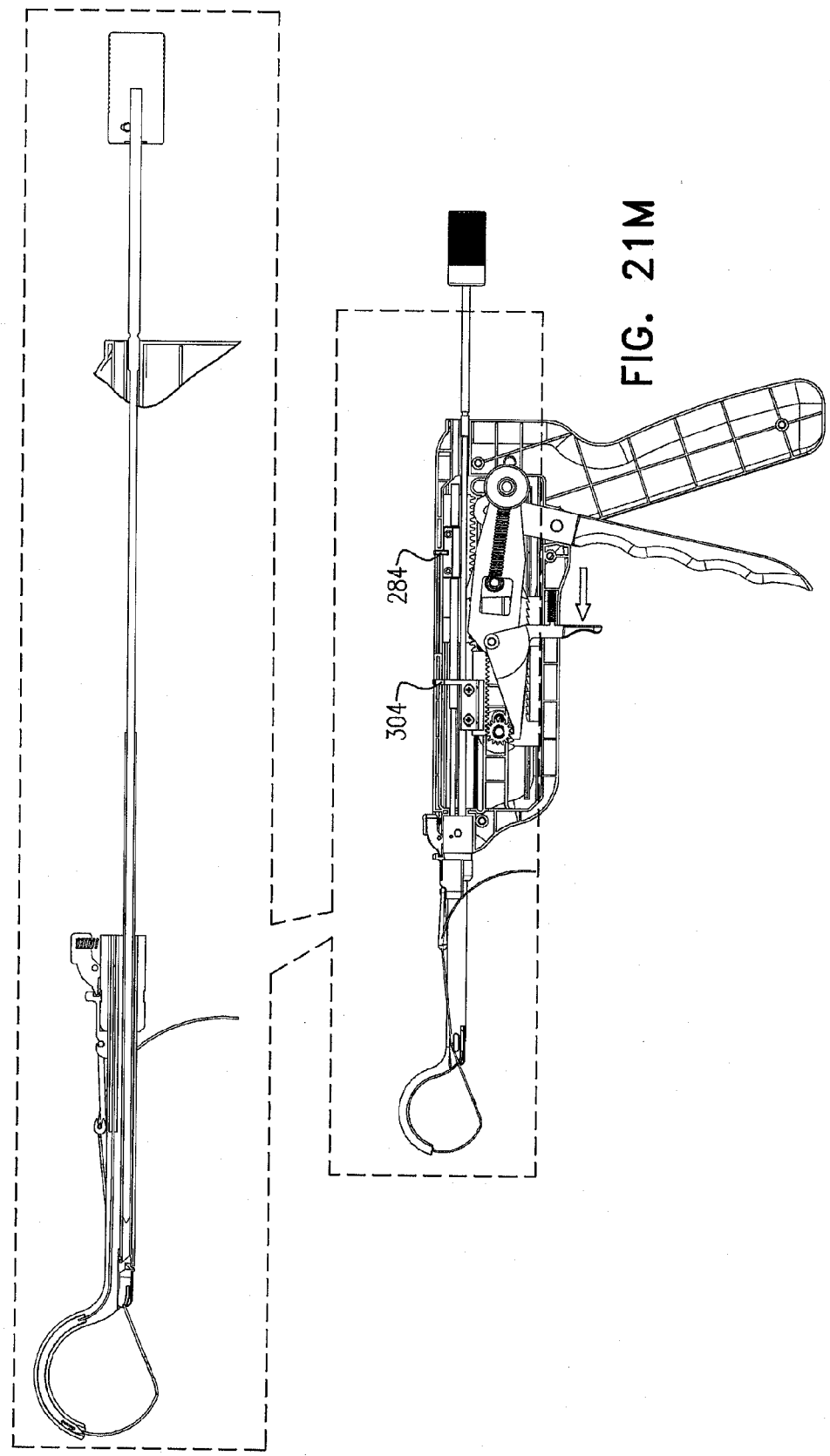

FIG. 21M shows full retraction of bone engagement pin 124.

Figure 22M:
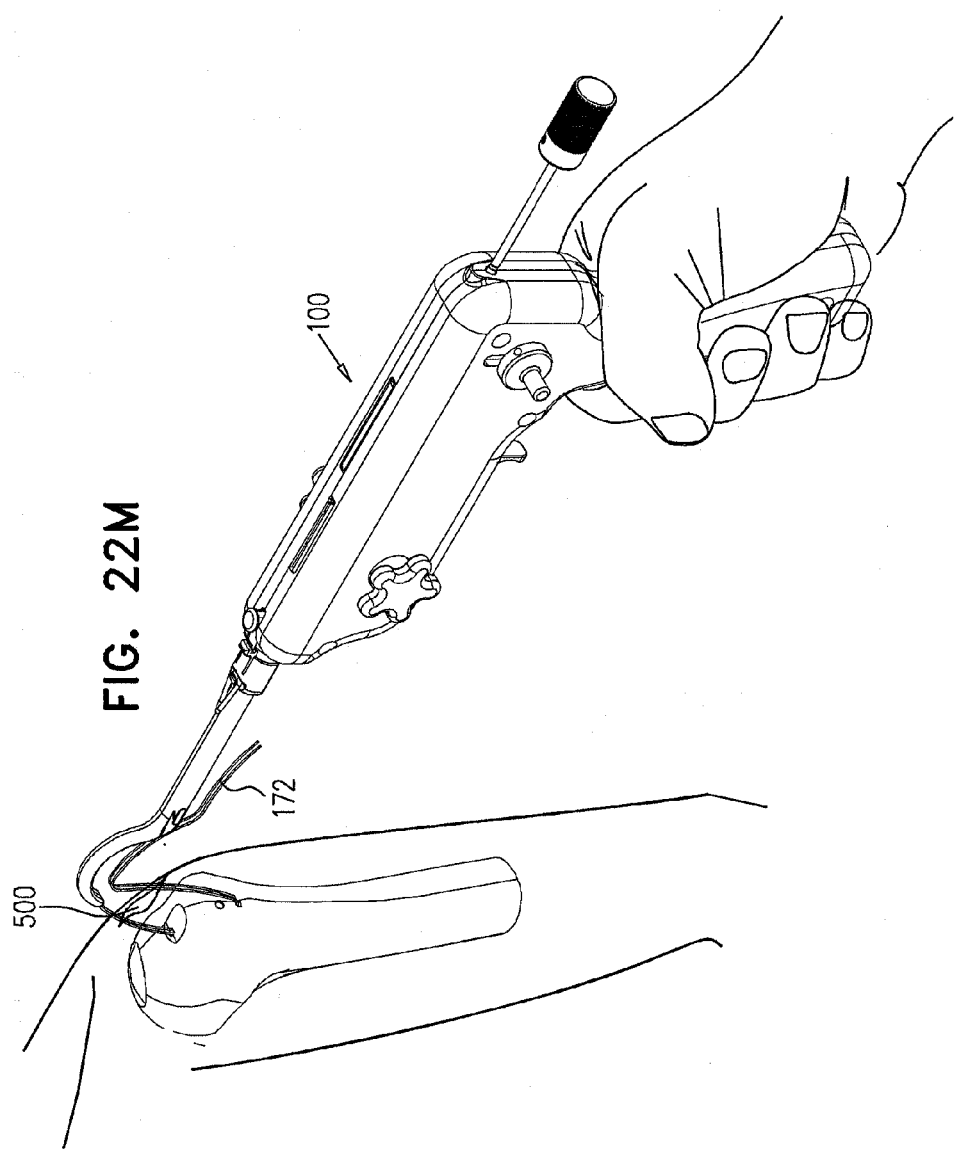

FIG. 22M shows full removal of the arthroscopic surgical device from the patient's body via the arthroscopic incision 500, with the suture 172 extending through the bone.

Figure 21N:
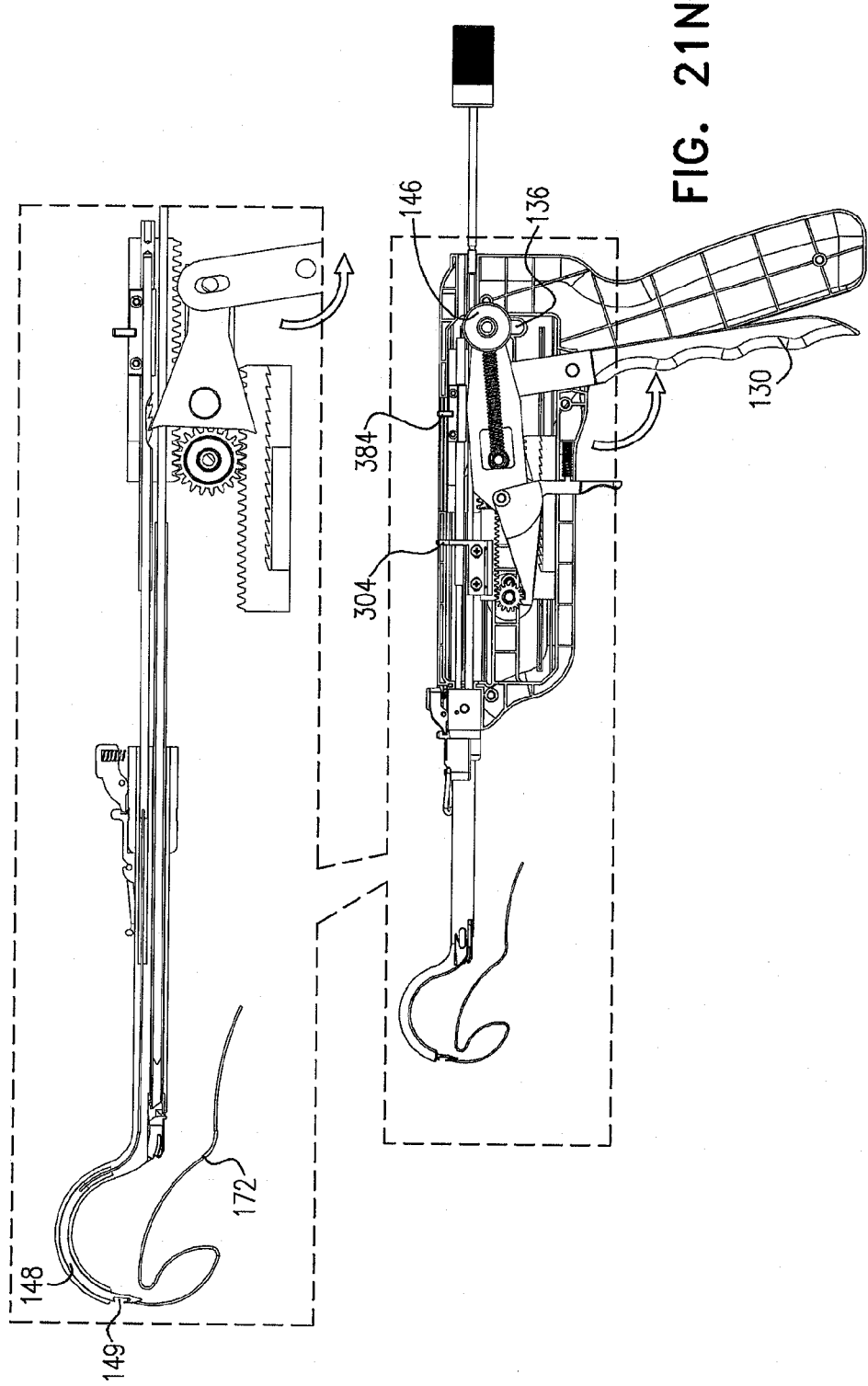

FIG. 21N shows slight extension of the needle 148 to enable manual disengagement of the suture 172 from groove 149 therein. This extension is produced by upward repositioning of knobs 146 in slots 136 and squeezing of handle 130.

FIG. 22N shows manual release of the forward part 174 of suture 172 from suture engagement groove 149 of needle 148.

It will be appreciated by persons skilled in the art that the present invention is not limited by what has been particularly shown and described hereinabove. Rather the scope of the present invention includes both combinations and subcombinations of the various features described hereinabove as well as modifications thereof which would occur to persons skilled in the art upon reading the foregoing description and which are not in the prior art.

The invention claimed is:

1. An arthroscopic surgical device for tunneling through hard tissue comprising:
    a multiple action driving assembly including:
        an at least partially flexible arcuate tunneling needle driver; and
        a linearly displaceable bone engaging pin driving assembly including a linear elongate bone engaging pin, said linear elongate bone engaging pin having an extended orientation in which said linear elongate bone engaging pin engages said hard tissue and a retracted orientation in which said linear elongate bone engaging pin does not engage said hard tissue,
    said at least partially flexible arcuate tunneling needle driver comprising:
        a hand-engageable ratchet handle arranged for reciprocal motion about an axis;
        a selectable direction ratchet gear driven by said ratchet handle; and
        a needle pushing element, driven by said ratchet gear, which is capable of assuming an arcuate orientation during needle driving operation thereof.

2. An arthroscopic surgical device for tunneling through hard tissue according to claim 1 and also comprising a rotatable bone engagement element.

3. An arthroscopic surgical device for tunneling through hard tissue according to claim 1 and wherein said bone engaging pin includes a tapered screw threading.

4. An arthroscopic surgical device for tunneling through hard tissue according to claim 1 and also comprising an arcuate tunneling needle.

5. An arthroscopic surgical device for tunneling through hard tissue according to claim 1 and wherein said arcuate tunneling needle driver includes:
    a flexible needle driving strip; and
    a generally rigid flexible needle driving strip driving shaft, mounted at a rear end of flexible needle driving strip.

6. An arthroscopic surgical device for tunneling through hard tissue according to claim 1 and also comprising an arcuate needle storage and guiding portion, formed with an arcuate bore.

7. An arthroscopic surgical device for tunneling through hard tissue according to claim 2 and also comprising a bone engagement element positioning assembly comprising:
    a finger-engageable release trigger;
    finger engageable bone engagement element advancement knobs; and
    a hollow bone engagement element driving shaft.

8. An arthroscopic surgical device for tunneling through hard tissue according to claim 1 and also comprising a needle and suture mounting assembly.

9. An arthroscopic surgical device for tunneling through hard tissue according to claim 1 and also including a bone suture insertion assembly comprising:
    a looped suture; and
    a tensionable resilient elongate element connected to said looped suture for selectable tensioning of said looped suture.

* * * * *